United States Patent [19]
Arnold, Jr. et al.

[11] Patent Number: 6,060,456
[45] Date of Patent: May 9, 2000

[54] CHIMERIC OLIGONUCLEOSIDE COMPOUNDS

[75] Inventors: Lyle J. Arnold, Jr., Poway; Mark A. Reynolds, San Diego; Cristina Giachetti, Solano Beach; Alexandre V. Lebedev, San Diego, all of Calif.

[73] Assignee: Genta Incorporated, Lexington, Mass.

[21] Appl. No.: 08/960,111

[22] Filed: Oct. 27, 1997

Related U.S. Application Data

[63] Continuation of application No. 08/481,637, Jun. 7, 1995, abandoned, which is a continuation of application No. 08/238,177, May 4, 1994, abandoned, which is a continuation of application No. 08/233,778, Apr. 26, 1994, abandoned, which is a continuation of application No. 08/154,013, Nov. 16, 1993, abandoned, which is a continuation of application No. 08/154,014, Nov. 16, 1993, abandoned.

[51] Int. Cl.[7] ............................. C12Q 1/68; A01N 43/04; C07H 19/00; C07H 21/00
[52] U.S. Cl. ................................ 514/44; 435/6; 435/91.1; 514/1; 536/22.1; 536/23.1; 536/25.3; 536/24.1; 536/24.2; 536/24.3; 536/24.32; 536/24.31; 536/24.33
[58] Field of Search .............. 435/6, 91.1; 514/44.1; 536/22.1, 23.1, 25.3, 24.1, 24.2, 24.3, 24.31, 24.32, 24.33

[56] References Cited

U.S. PATENT DOCUMENTS

| | | | |
|---|---|---|---|
| 5,212,295 | 5/1993 | Cook | 536/26.7 |
| 5,220,007 | 6/1993 | Pederson et al. | 536/23.1 |
| 5,470,967 | 11/1995 | Huie et al. | 536/24.3 |

OTHER PUBLICATIONS

Bower et al. "Oligodeoxyribonucleoside methylphosphonates. NMR and UV spectroscopic studies of Rp—Rp and Sp—Sp methylphosphonate (Me) modified duplexes of {d[GGAATCC]}$_2$ "Nucleic Acids Research, vol. 15, pp. 4915–4930, 1987.

Akhtar et al. "Stability of antisense DNA oligodeoxinucleotide analogs in cellular extracts and sera" Life Science, vol. 49, pp. 1793–1801, 1991.

*Primary Examiner*—Jezia Riley
*Attorney, Agent, or Firm*—Knobbe, Martens, Olson & Bear LLP.

[57] ABSTRACT

Chimeric oligonucleoside compounds, and methods of preparing and formulating the same, are disclosed. The compounds and compositions are useful in activating RNaseH-mediated cleavage of target ribonucleic acid sequences, and in treating disease conditions relating to such sequences.

38 Claims, 12 Drawing Sheets

PHOSPHOTRIESTER

H-PHOSPHONATE

PHOSPHORMONOCHLORIDITE

CHIMERIC OLIGONUCLEOSIDE COMPOUNDS

This application is a continuation of application(s) Ser. No. 08/481,637 filed on Jun. 7, 1995 now abandoned, which is a continuation of Ser. No. 08/238,177 filed on May 4, 1994 now abandoned, which is a continuation of Ser. No. 08/233,778 filed on Apr. 26, 1994 now abandoned, which is a continuation of Ser. No. 08/154,013 filed on Nov. 16, 1993 now abandoned which is a continuation of Ser. No. 08/154,014 filed Nov. 16, 1993, now abandoned.

FIELD OF THE INVENTION

The present invention relates to antisense oligonucleoside compounds containing modified internucleoside linkages, and optionally other structural modifications. The compounds are capable of hybridizing to target nucleic acid sequences and activating RNaseH-mediated cleavage of the target.

RELATED APPLICATIONS

This application is a continuation-in-part of commonly assigned PCT application Ser. No. PCT/US94/13387, filed Nov. 16, 1994, which is a continuation-in-part of commonly-assigned U.S. patent application Ser. No. 08/238,177, filed May 4, 1994, which is a continuation-in-part of commonly-assigned U.S. patent application Ser. No. 08/233,778, filed Apr. 26, 1994, which is a continuation-in-part of commonly-assigned U.S. patent application Ser. Nos. 08/154,013 and 08/154,014, both filed Nov. 16, 1993. The entire disclosures of all of these applications are incorporated herein by reference.

BACKGROUND OF THE INVENTION

Considerable attention has been directed in recent years to the design of antisense nucleic acid oligomers for use in studying, treating and diagnosing conditions attributable to endogenous or foreign nucleic acid sequences in living organisms. For example, it is now well known that a nucleic acid oligomer having suitable antisense complementarity to a target mRNA can hybridize to the target mRNA and, in some cases, disrupt translation of the mRNA. The antisense approach presents great promise for the eventual therapeutic treatment of disease conditions caused by foreign (e.g., viral) genetic material, or by misfunctioning or altered endogenous genetic material (e.g., cancer and genetic disease conditions).

However, despite the great promise of the antisense approach, a number of challenges still remain. First, antisense compounds are generally subject to degradation in the cellular milieu due to endogenous endo- and exonucleases. While a number of modified antisense structures have been described having improved resistance to nuclease degradation, further improvements are desirable in order to increase the potency and half-life of the compounds. Second, it is generally required that an antisense compound have a high specificity toward the intended target nucleic acid so as to avoid disruption of activity of unintended native sequences. Although a number of researchers have described approaches designed to increase the binding affinity of an antisense compound to a target sequence, very few results have been reported with respect to structural refinements which avoid disruption of the activity of unintended genetic sequences while still retaining maximum efficacy against the target sequence.

One approach toward disrupting the expression of undesired target mRNAs involves forming a duplex hybrid between the target mRNA and an antisense strand, followed by cleavage of the target mRNA by an endogenous RNaseH. See Dash, P., et al, Proc. Natl. Acad. Sci. U.S.A. 84:7896–7990 (1987). However, because the mode of action of RNaseH is fairly specific, this approach is subject to a number of constraints. First, RNaseH enzymes act in nature to cleave the oligoribonucleic acid strand of an oligodeoxyribonucleotide-oligoribonucleotide duplex, but do not cleave DNA-DNA or RNA-RNA duplexes. This has been attributed, at least in part, to the polar nature of DNA-RNA hybrids which, in contrast to DNA-DNA and RNA-RNA hybrids, have 2'-OH groups on one (but only one) strand. Crouch, R. J. & Dirksen, M.-L., "Ribonucleases H," in Nucleases (Linn & Roberts, eds.), Cold Spring Harbor Laboratory (1982), at 212. As a result, one putative requirement of the antisense RNaseH cleavage approach is that at least some of the nucleosides of the antisense nucleic acid strand must have characteristics in common with deoxyribonucleotides (as opposed to ribonucleotides), particularly, the absence of a polar group on the 2'-position of the antisense nucleoside sugars. Perhaps related to this is the additional requirement that at least some of the sugar groups in the antisense compound must be in a 2'-endo (β) conformation as found in deoxyribonucleosides, as opposed to the 3'-endo (α) conformation found in ribonucleosides. Cook P. D., PCT Publication No. WO 93/13121 (1993), at 18–19.

It has further been reported that various 2'-position substituents (e.g., 2'-O-alkyl and 2'-fluoro) will render the substituted portion of an antisense strand non-activating to RNaseH, even though binding affinity toward the target nucleic acid is increased. Inoue, H., et al., FEBS Letters 215(2):327–330 (1987); Monia, B. P., et al., J. Biol. Chem. 268(19):14514–14522 (1993). Likewise, the Monia, et al. report indicates that a minimum of five consecutive 2'-deoxy residues is required in order to achieve efficient activation of mammalian (HeLa) RNAseH, and that this 2'-deoxy segment (if accompanied by 2'-substituted residues in the same antisense compound) must be centered in the oligomer sequence in order to achieve efficient RNaseH activation in vitro or expression inhibition in cells.

Another reported requirement of the antisense RNaseH cleavage approach is that, in order to achieve RNaseH activation, at least one portion of the internucleoside "backbone" of the antisense compound must include charged (anionic) phosphorus-containing linkage groups. Cook, P. D., PCT Publication No. WO 93/13121 (1993), at 18. In studies of chimeric antisense compounds including both methylphosphonate (uncharged) and phosphodiester or phosphorothioate (charged) linkages, Agrawal, et al. reported that the minimum number of consecutive charged backbone linkages required for efficient activation of mammalian RNaseH in vitro is five. Phosphodiester linkages positioned in either the terminal or center portion of the oligomers were reportedly more efficient than phosphorothioate linkages in activating RNaseH, whereas oligomers containing only methylphosphonate, phosphoro-N-morpholidate or phosphoro-N-butylamidate linkages were inactive. Agrawal, S., et al., Proc. Natl. Acad. Sci. U.S.A. 87:1401–1405 (1990).

While phosphodiester linkages, being charged, are suitable to allow activation of RNaseH, they suffer from the disadvantage of being subject to degradation by naturally-occurring endo- and/or exonucleases. A variety of alternative linkage groups, some of which are nuclease-resistant, have been developed or proposed for use with antisense compounds. Among these are charged linkage groups such as phosphorothioate, phosphorodithioate, phosphoroselenate and phosphorodiselenate linkers. In general, deoxyribonucleoside antisense oligomers containing these non-natural linkage groups tend to have lower binding affinity toward complementary RNA target strands than the corresponding phosphodiester-linked antisense oligomers, although higher affinity may be achieved where the antisense strand comprises ribonucleosides or 2'-substituted ribonucleosides (rather than deoxyribonucleosides). See Metelev, V. & Agrawal, S., PCT Publication No. WO 94/02498 (1994), at 9. Among the uncharged phosphorus-containing linkage groups that have been reported are the alkylphosphonate (e.g., methylphosphonate), aryl phosphonate, alkyl and aryl phosphoramidate, alkyl and aryl phosphotriester, hydrogen phosphonate, boranophosphate, alkyl and aryl phosphonothioate, phosphoromorpholidate, and phosphoropiperazidate linkers. See Cook, P. D., PCT Publication No. WO 93/13121 (1993), at 7; Pederson, T., et al., U.S. Pat. Nos. 5,149,797 and 5,220,007; Padmapriya, A. & Agrawal S., PCT Publication No. WO 94/02499 (1994). Non-phosphorus-based linkage groups have also been reported, including peptide, morpholino, ethylene glycol, amide, and other linkers. See Reynolds, M. A., et al., PCT Publication No. WO 92/02532 (1992); Cook, P. D., PCT Publication No. WO 93/13121 (1993), at 7. As with the charged phosphorus-containing linkers noted above, many of these other non-natural linkage groups may exhibit lower binding affinity (compared to phosphodiester linkages) toward complementary RNA target strands, at least in the case of linked 2'-unsubstituted antisense nucleotides, and particularly in the presence of salt ions.

Various workers have attempted to identify combinations of linkage groups and/or structural modifications for antisense oligomers that might lead to improved RNaseH activation, binding affinity, nuclease resistance and/or target specificity. Thus, Cohen, et al. have reported improved half-life for antisense and non-antisense oligodeoxyribonucleotides containing at least one phosphorothioate linkage located, for example, at either terminus of the compound, or throughout the compound. Oligomers containing all phosphorothioate linkages were shown to have anti-viral (anti-HIV) activity, whereas phosphodiester- and methylphosphonate-linked compounds were reportedly inactive. Cohen, J. S., et al., U.S. Pat. No. 5,264,423. Walder et al. have proposed the use of a 3'-terminal non-phosphodiester linkage, optionally combined with a 5'-terminal non-phosphodiester linkage or a 5'-terminal "cap" group, to avoid 3'-initiated (and optionally 5'-initiated) exonuclease degradation of oligodeoxyribonucleotides. RNaseH cleavage activation reportedly required retention of at least four, and preferably at least seven, contiguous phosphodiester linkages in the antisense oligomer. The preferred compounds contained at least 10, and preferably at least 15, nucleotides, the majority of which were phosphodiester-linked. Walder, J. A., et al., PCT Publication No. WO 89/05358 (1989). Padmapraya & Agrawal have reported that the incorporation of nonionic alkyl or aryl phosphonothioate linkages, preferably at one or both termini of the oligomer, resulted in improved nuclease resistance, albeit with a reduction in Tm of 1–2° C./phosphonothioate linkage. PCT Publication No. WO 94/02499 (1994).

Pederson, et al. have reported the use of "mixed phosphate backbone" oligomers containing both a phosphodiester- or phosphorothioate-linked segment for RNaseH activation, and one or more non-RNaseH-activating, uncharged linkage group segments. It was found that a segment of five or six consecutive phosphodiester linkages was efficient, in a 15-mer compound, to effect RNaseH cleavage of a target RNA strand, whereas similar compounds with fewer phosphodiester linkages, or with up to six consecutive phosphorothioate linkages in place of the phosphodiester linkages, had low activity. Pederson, T., et al., U.S. Pat. Nos. 5,149,797 and 5,220,007.

Giles & Tidd have reported that the target specificity of an antisense oligomer can be improved by the use of a chimeric structure comprising terminal methylphosphonodiester sections separated by a central RNaseH-activating phosphodiester region having a high A+T to G+C ratio. The observed reductions in non-specific cleavage were attributed to the lower Tm caused by the methylphosphonate segments, the reduced hybridization strength of the small, A/T-rich phosphodiester region, and the reduced prospects for partially-complementary hybridization at the shortened RNaseH activation site. Giles, R. V. & Tidd, D. M., Nucl. Acids Res. 20(4):763–770 (1992).

Ohtsuka, et al. have described the use of partially 2'-substituted (e.g., 2'-lower alkoxy substituted) oligomers for site-specific RNaseH cleavage of RNA targets with or without secondary structure. RNaseH cleavage was reportedly localized to a site (or sites) on the target corresponding to the non-substituted (i.e., deoxyribonucleotide) portion of the antisense compound. Single-site cleavage was reportedly optimized by use of a tetradeoxyribonucleotide segment located centrally in the compound between two 2'-substituted terminal segments. Inoue, H., et al., FEB Letters 215(2):327–330 (1987); Shibahara, S., et al., Nucl. Acids Res. 15(11):4403–4415 (1987); Ohtsuka, E., et al., U.S. Pat. No. 5,013,830. The use of partially 2'-substituted oligomers additionally containing one or more non-phosphodiester linkages has also been reported. See Shibahara, S., et al., European Patent Application Publication No. 0 339 842 A2 (1989) (reporting 3'–5' or 2'–5' linked oligomers having phosphorothioate or other linkages); Cook, P. D., PCT Publication No. WO 93/13121 (1993) (reporting increased binding affinity attributable to 2'-substitutions, and nuclease resistance attributable to, e.g., phosphorothioate and phosphorodithioate linkages); Monia, B. P., et al., J. Biol. Chem. 268(19):14514–14522 (1993) (reporting effects of 2'-substitutions in phosphorothioate-linked oligomers); Metelev, V. & Agrawal, S., PCT Publication No. WO 94/02498 (1994) (reporting use of $2^1$-substitutions in phosphorothioate- or phosphorodithioate-linked oligomers); McGee, D. P., et al., PCT Publication No. WO 94/02501 (1994) (describing preparation of various 2'-substituted nucleosides and phosphoramidites).

SUMMARY OF THE INVENTION

The present invention relates to improved RNaseH-activating antisense oligonucleoside compounds containing selectively modified internucleoside linkages, and optionally other structural modifications. The compounds exhibit improved target specificity and potency compared to other RNaseH-activating antisense compounds. They are useful both in vivo and in vitro in reducing or eliminating the translation of target mRNA sequences, most preferably sequences related to disease conditions.

In one aspect, the present compounds incorporate one or more polynucleoside segments having chirally-pure or chirally-enriched modified (non-phosphodiester) internucleoside linkages. The chirally-selected linkage segments are preferably selected to include linkages having R chirality at the asymmetric phosphorus atom of one or more of the linkage structures ("$R_p$ chirality"). Preferably, at least about 40% of the linkages in a given chirally-selected segment will be $R_p$-chiral. Also included are segments selectively including one or more $S_p$-chiral linkages. In one preferred embodiment, chirally-selected segments are situated at the terminal (3' and 5') portions of the compound, surrounding (flanking) a central RNaseH-activating region. The flanking chirally-selected segments preferably are substantially non-RNaseH-activating. The RNaseH-activating region, if linked with asymmetric (chiral) linkage groups, may alternatively or additionally be chirally selected. In a related embodiment, the RNaseH-activating region is situated at or near one terminus of the compound, and all or a portion of the remainder of the compound is chirally selected and preferably is non-RNaseH-activating.

The chirally-selected $R_p$-enriched segments of the invention serve to increase the binding affinity of the compound as compared to racemic compounds. In addition, because the chirally-selected modified linkage structures are more resistant to degradation by endo- and/or exonucleases than are non-modified phosphodiester linkages, the chirally-selected segments will tend to protect the compound from degradation in the in vivo environment.

In another aspect, the present compounds incorporate one or more polynucleoside segments comprising mixed modified (non-phosphodiester) internucleoside linkages. Two or more different internucleoside linkage structures are included in the mixed linkage segment, and one or more of these may be a modified linkage structure. One or more of the linkage structures in the sequence may be chirally selected. Preferably, the mixed linkage segment includes multiple linkage sequence blocks (synthons) each containing two or more different internucleoside linkage structures, or a single such synthon that is repeated two or more times in the mixed linkage segment. Where the compound contains more than one mixed linkage segment, the linkage sequence blocks may be the same or different in the respective segments. In one preferred embodiment, mixed linkage segments are situated at the terminal (flanking) portions of the compound, surrounding a central RNaseH-activating region. The RNaseH-activating region may alternatively or additionally comprise a mixed linkage segment. The flanking mixed linkage segments are preferably non-RNaseH-activating. In a related embodiment, the RNaseH-activating region is situated at one terminal portion of the compound, and all or a portion of the remainder of the compound contains a mixed linkage segment and preferably is non-RNaseH-activating.

The mixed linkage segments of the invention may be racemic or chirally selected; in either case the identity of the internucleoside structures and/or the linked nucleoside substituents can be selected to afford greater binding affinity to the compound while maintaining target specificity and nuclease resistance and increasing potency. Because the mixed linkage segments of the compound include one or more modified internucleoside linkage structures that are resistant to degradation by endo- and/or exonucleases, the compounds will have higher potency in the in vivo environment.

In another aspect, the present invention includes improved RNaseH-activating segments comprising linked nucleosides having mixed internucleoside linkages. In one preferred embodiment, the RNaseH-activating segment includes at least five consecutive 2'-unsubstituted (i.e. DNA) nucleoside residues linked by two or more different charged (anionic) internucleoside linkage structures in an alternating sequence. Preferably, the RNaseH-activating segment includes at least four such charged internucleoside linkage structures. One or more of the internucleoside linkage structures in the RNaseH-activating segment may be chirally selected if an asymmetric phosphorus atom is present in the linkage structure.

In another aspect, the present invention provides chimeric structures for antisense oligonucleoside compounds that maximize activity while maintaining the ability to effect selective RNaseH-mediated cleavage of the intended target strand. These goals are achieved by structures which provide, on the one hand, controlled binding affinity and, on the other hand, controlled RNaseH-activation characteristics.

Thus, in one embodiment, binding affinity is controlled (selectively increased) through the use of chirally-selected $R_p$-chiral internucleoside linkages in one or more portions of the compound. Alternatively or additionally, one or more $S_p$ linkages may be used to selectively decrease binding affinity. In a related embodiment, binding affinity is controlled (selectively increased) through the use of multiple or repeated linkage sequence blocks (synthons) in one or more mixed linkage segments of the compound; the linkage structures may be racemic or chirally-selected. In another related embodiment, binding affinity is controlled (selectively increased) through the use of 2'-substituents on one or more nucleoside sugars in the compound, preferably in conjunction with alternating linkage segments and/or chirally-selected internucleoside linkages. RNaseH-activating characteristics can simultaneously be controlled (substantially eliminated, or selectively increased) in these segments of the compound by the use of 2'-substituted or unsubstituted nucleoside sugars and/or by the selection of uncharged or charged linkage structures for a given segment of the compound.

Likewise, RNaseH-activation characteristics are controlled (selectively increased or decreased) by the selection of mixed or uniform charged internucleoside linkages in the RNaseH-activating region of the compound. RNaseH-activating characteristics can be selectively decreased, particularly in the RNaseH-activating region of the compound, by the use of linkage structures such as phosphorothioate or especially phosphorodithioate structures that are poorer substrates for RNaseH. RNaseH-activating characteristics are also controlled by the inclusion of non-RNaseH-activating portions in the compound such that only a portion of the compound is effective in activating cleavage of the target genetic sequence, for example by appropriate selection of linkage structures, 2'-substituents and other features as described herein.

Among the highly preferred compounds of the invention are those having substantially non-RNaseH-activating, chirally-selected, mixed linkage segments at the two terminal (flanking) portions of the compound, and an RNaseH-activating region positioned therebetween. Also preferred are compounds having substantially non-RNaseH-activating, racemic mixed linkage segments at the two terminal (flanking) portions of the compound wherein one or more of the linked nucleosides in the mixed linkage segments is 2'-substituted, and an RNaseH-activating region is positioned in the compound between the mixed linkage segments. Especially preferred compounds include those chosen from the following structures:

| 5'-Terminal Portion | RNaseH-Activating Region | 3'-Terminal Portion |
|---|---|---|
| MP(R)/DE | DE | MP(R)/DE |
| 2'OMeMP(R) /2'OMeDE | PS2 | 2'OMeMP(R) /2'OMeDE |
| MP(R)/2'OMeMP | PS | MP(R)/2'OMeMP |
| MP(R) enriched | Ps2/DE | MP(R) enriched |
| 2'OMeMP(R) enriched | PS/DE | 2'OMeMP(R) enriched |
| MP(R)/PS | PS/PS2 | MP(R)/PS |
| 2'OMeMP(R) /2'OMePS | | 2'OMeMP(R)/2'OMePS |
| MP(R)/PS2 | | MP(R)/PS2 |
| 2'OMeMP(R)/2'OMePS2 | | 2'OMeMP(R)/2'OMePS2 |
| 2'OMeMP/2'OMeDE | | 2'OMeMP/2'OMeDE |
| MP/2'OMeDE | | MP/2'OMeDE |
| MP(R)/PAm | | MP(R)/PAm |
| 2'OMeMP(R)/2'OMePAm | | 2'OMeMP(R)/2'OMePAm |
| 2'OMeMP/2'OMePAm | | 2'OMeMP/2'OMePAm |
| MP/2'OMePAm | | MP/2'OMePAm |
| MP(R)/TE | | MP(R)/TE |
| 2'OMeMP(R)/2'OMeTE | | 2'OMeMP(R)/2'OMeTE |
| 2'OMeMP/2'OMeTE | | 2'OMeMP/2'OMeTE |
| MP/2'OMeTE | | MP/2'OMeTE |
| MP(R)/MPS | | MP(R)/MPS |
| 2'OMeMP(R)/2'OMeMPS | | 2'OMeMP(R)/2'OMeMPS |
| 2'OMeMP/2'OMeMPS | | 2'OMeMP/2'OMeMPS |
| MP/2'OMeMPS | | MP/2'OMeMPS |
| MP(R)/PF | | MP(R)/PF |
| 2'OMeMP(R)/2'OMePF | | 2'OMeMP(R)/2'OMePF |
| 2'OMeMP/2'OMePF | | 2'OMeMP/2'OMePF |
| MP/2'OMePF | | MP/2'OMePF |
| MP(R)/PBH$_3$ | | MP(R)/PBH$_3$ |
| 2'OMeMP(R)/2'OMePBH$_3$ | | 2'OMeMP(R)/2'OMePBH$_3$ |
| 2'OMeMP/2'OMePBH$_3$ | | 2'OMeMP/2'OMePBH$_3$ |
| MP/2'OMePBH$_3$ | | MP/2'OMePBH$_3$ |
| MP(R)/RSi | | MP(R)/RSi |
| 2'OMeMP(R)/2'OMeRSi | | 2'OMeMP(R)/2'OMeRSi |
| 2'OMeMP/2'OMeRSi | | 2'OMeMP/2'OMeRSi |
| MP/2'OMeRSi | | MP/2'OMeRSi |
| MP(R)/CH$_2$ | | MP(R)/CH$_2$ |
| 2'OMeMP(R)/2'OMeCH$_2$ | | 2'OMeMP(R)/2'OMeCH$_2$ |
| 2'OMeMP/2'OMeCH$_2$ | | 2'OMeMP/2'OMeCH$_2$ |
| MP/2'OMeCH$_2$ | | MP/2'OMeCH$_2$ |

Key:
MP = racemic methylphosphonate linkage (between linked nucleosides);
MP(R) = chirally-selected $R_p$-methylphosphonate linkage;
DE = phosphodiester linkage;
PS = phosphorothioate linkage;
PS2 = phosphorodithioate linkage;
PAm = phosphoramidate linkage;
TE = phosphotriester linkage;
MPS = alkyl (particularly methyl) phosphorothioate linkage;
PF = phosphorofluoridate linkage;
PBH$_3$ = boranophosphate linkage;
RSi = silyl (especially alkyl-disubstituted silyl) linkage;
CH$_2$ = formacetal linkage;
2'OMe = 2'-methoxy-substituted (or other lower alkoxy, allyloxy or halo suostituted) nucleoside residue, linked using the listed linkage structure; "enriched" refers to a segment of linkages preferably containing at least about 40% (and up to 100%) $R_p$-selected linkages among the linkages in the segment, and thus includes a mixed segeunce of racemic and chirally-selected R internucleoside linkage structures;
linkage structures grouped with slashes denote a mixed linkage segment including the listed linkage structures, optionally in a series of multiple or repeated mixed linkage sequence blocks.

In another aspect, the present invention includes improved antisense oligonucleoside compositions useful in treating or diagnosing diseases or other conditions in living organisms attributable to the expression of endogenous or foreign genetic information. The compounds and compositions are also useful in studying such conditions in vitro or otherwise. In another aspect, the invention provides methods for treating, diagnosing or studying such conditions.

Other aspects and objects of the invention will be apparent from the following detailed description.

DETAILED DESCRIPTION

Figure 1A:
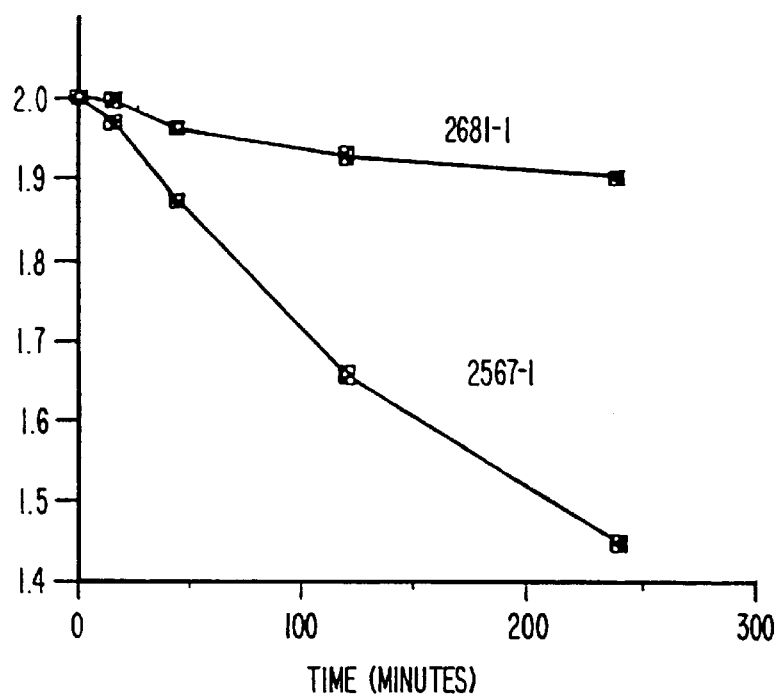
FIGS. 1 and 2 are graphs showing nuclease stability of various compounds and segments of the present invention, compared to other mixed linkage compounds, over time.

A full appreciation of the present invention requires an understanding of the competing parameters underlying the present RNaseH cleavage technique. There are a number of parameters of primary concern, including oligonucleoside-target binding affinity, RNaseH cleavage rate, specificity/mismatch effects, oligonucleoside displacement by processing ribosomes, and nuclease stability. As will be seen from the following discussion, a proper balance of these competing parameters requires that the oligonucleoside compound have a binding affinity (as quantitated for example by the affinity constant $K_A$) that is not too large relative to the RNaseH cleavage rate. The present invention provides structures that satisfy this requirement as well as other requirements outlined below.

The present technique of RNaseH cleavage of a target genetic sequence requires that the oligonucleoside compound hybridize with the target sequence, and that the oligonucleoside have a hybridization occupancy time that is sufficiently long to effect cleavage of the target sequence by the RNaseH enzyme. The initial step of oligonucleoside-target hybridization is governed, from a first-order kinetic standpoint, by the forward and reverse rate constants ($k_1$ and $k_{-1}$) that define $K_A$, where $K_A = k_1/k_{-1}$. The rate of cleavage of the target (which is essentially irreversible) is then governed by the rate constant $k_2$, as follows:

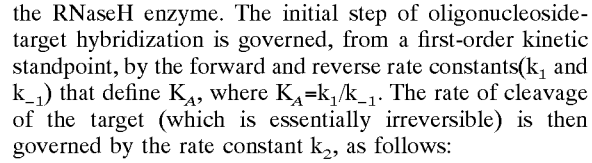

Other considerations aside, it would appear that target cleavage would be optimized by maximizing both $K_A$ and $k_2$. However, this does not take into account the problem of non-specific binding (i.e. mismatches) between the oligonucleoside and unintended nucleic acid sequences that exist in the cleavage (e.g. cellular) medium which could result in undesired cleavage of the unintended sequences. Nor does this simple approach take into account the fact that an oligonucleoside with high binding affinity will typically be displaced from its hybridized state, and thus will be unable to activate RNaseH-mediated cleavage, each time the host ribosome processes along the target mRNA sequence.

Consider first the challenge of achieving high target specificity with an antisense cleavage compound. Mammalian cells typically contain an RNA population comprising about 3×10⁷ ribonucleotides. By assuming a statistically random distribution of the four naturally-occurring nucleotides within this population, the total number of "match" sequences in the population having exact base-by-base complementarity, and the number of "mismatch" sequences having one or more base mismatches, can be approximated for a target sequence of any given length. (Of course, the actual distribution of ribonucleotides in a given mammalian cell population will not be truly random, but nevertheless such statistical analyses can shed light on the probabilities of a mismatch sequence occurring.) The following table lists the number of targets that would exist in such a population as a function of number of mismatches (zero to five) and target sequence length (12, 15 or 18).

| Mismatches/Length | Targets |
|---|---|
| 0/12 | 1.8 |
| 0/15 | $2.8 \times 10^{-2}$ |
| 1/15 | 1.24 |
| 2/15 | 26 |
| 3/15 | 340 |
| 0/18 | $4.4 \times 10^{-4}$ |
| 1/18 | $2.4 \times 10^{-2}$ |
| 2/18 | 0.62 |
| 3/18 | 9.6 |
| 4/18 | 109 |
| 5/18 | 930 |

It will be seen that an appreciable number of potential mismatch sequences may exist even for target sequences as long as 12 nucleosides, particularly as the number of single-base mismatches increases. If the $K_A$ for a given mismatch duplex is sufficiently high as to allow appreciable hybridization of an antisense oligomer to a mismatched target, then unintended and undesirable cleavage of the mismatched target can result.

Take, for example, the case of a one-base mismatch between a 12-to-18 nucleoside antisense oligomer and an unintended mismatch RNA sequence. The present inventors have ascertained that the $K_A$ for the correct "match" hybridization typically does not exceed the $K_A$ for the incorrect "mismatch" hybridization by more than a factor of one hundred. Furthermore, the forward rate constant of hybridization ($k_1$) will be approximately the same for both the match and the mismatch, because the forward hybridization is typically governed in large part by the physics of solution-phase intermolecular exposure which tend to obscure the effect of the single-base mismatch. In this case, the hybridization "off rate" ($k_{-1}$) can be no more than 100 times greater for the mismatch than for the correct match. It will now be seen that, if the cleavage rate constant $k_2$ is not substantially smaller than the reverse rate constant $k_{-1}$ for the mismatch, then unintended mismatched nucleic acid sequences will be cleaved (along with the properly matched target sequence). It will also be seen that specificity for the intended target sequence will be optimized if $k_2$ has a value on the order of $k_{-1}$(match), but much less than $k_{-1}$(mismatch):

$$k_{-1}(\text{match}) \approx k_2 \ll k_{-1}(\text{mismatch})$$

In addition, the present invention takes into account the ribosomal displacement of hybridized oligonucleosides that typically occurs in the coding region of a target mRNA during the process of RNA translation. The ribosomal processional rate varies somewhat from RNA to RNA but in general is calculated to pass any single point on an mRNA every 10–15 seconds. If the $K_A$(match) for a given oligonucleoside is $10^{10}$ M$^{-1}$ and the $K_A$(mismatch) is $10^8$ M$^{-1}$, then the half-life hybridization occupancy times ($t_{1/2}$) will be about 28 minutes and 17 seconds, respectively, for the match and the mismatch. But because the ribosomal processional rate is so fast, the correctly-matched oligonucleoside will be displaced from the target sequence just about as frequently as the mismatched oligomer, and the effective occupancy times will be approximately the same. The result in this case is that, from a specificity standpoint, the high affinity constant for the correctly matched hybridization goes for naught, and nonspecific cleavage will occur at least as frequently as the intended sequence-specific cleavage. In fact, nonspecific cleavage may occur even more frequently if more than one mismatch sequence exists in the "target" RNA population.

Given considerations such as these, the present inventors have discovered that it is beneficial in many cases to limit the binding affinity constant of the subject RNaseH-activating oligonucleoside compounds to values that are typically no greater than $10^{10}$ M$^1$ for targets in the coding region of a target mRNA. (An exception to this exists with respect to certain oligomer constructs of the invention described below, particularly constructs designed to target single base changes in target RNA sequences. As explained below, the exceptionally high cleavage specificity exhibited by such oligomer constructs allows use of structures having higher binding affinity.) Preferred $K_A$ values for the present compounds are in the range $10^7$–$10^{10}$ M$^{-1}$. In such a case, because the "off rate" will be relatively high compared to compounds with higher binding affinities, it is possible and desirable to utilize compounds having a relatively high cleavage rate. Thus, the inventors have discovered that it is beneficial to control the cleavage rate constant of the subject compounds to values in the range of 1 to $10^{-5}$ sec$^{-1}$, preferably $10^{-1}$ to $10^{-4}$ sec$^{-1}$, and most preferably $10^{-2}$ to $10^{-3}$ sec$^{-1}$. The cleavage rate is preferably selected to give at least a 3:1 cleavage rate of a perfect "match" relative to a 2-mismatch target.

In contrast, in the non-coding region of a target mRNA site (e.g., the 5'-cap region, the 5'-untranslated region, the initiation codon region, the 3'-untranslated region, splice acceptor or donor sites, intron branch sites, and polyadenylation sites), inhibition of protein production can be achieved prior to the translation process by suitable hybridization of an antisense oligonucleoside, and ribosomal displacement of the hybridized oligomer generally does not occur. As a result, oligonucleosides having higher binding affinities (and higher half-life occupancy times) can be utilized in the non-coding region without the loss of specificity described above with respect to the coding region. In this case, an upper limit on binding affinity will be imposed by the lifetime of messages in the mRNA pool relative to the lifetime of mismatch hybrids. Thus, the lifetime of a typical mRNA molecular species (taking into account replenishment of the mRNA pool via transcription) is on the order of five hours. If the hybrid lifetime of mismatch sequence approaches an hour or more, then the translation of the mismatched message will be perturbed by steric blocking effects apart from any RNaseH cleavage mechanism. As a result, $K_A$(match) should generally be in the range $10^7$–$10^{13}$ M$^{-1}$. Furthermore, a relatively low concentration of oligonucleoside is preferably used in this case so that the total level of mismatch occupancy over time (in addition to the mismatch hybrid lifetime of a single mismatched oligonucleoside) is low. (Of course, the rate of RNaseH-mediated cleavage, $k_2$, should still be much lower than $k_{-1}$(mismatch) for targets in the non-coding region, just as it is for coding region targets, in order to avoid non-specific mismatch cleavage.)

Values for $K_A$, $k_1$, $k_{-1}$ and $k_2$ can be ascertained using methods known in the art. The determination of $K_A$, the equilibrium binding constant, requires the measurement of the concentrations (absolute or relative) of single and multimeric species, as well as enough time to ensure complete equilibration. The equilibrium hybridization of oligomers can be studied by direct methods which physically separate the single and multi-meric species, such as gel shift (Lima et al., Biochemistry 31, 12055–61 (1992)), strand cleavage (Young, S., Wagner, R. W., Nucleic Acid Research 19, 2463–70 (1991)), filter binding (McGraw, R. A. et al., BioTechniques 8, 674–678), or equilibrium dialysis (Bevilacqua, P. C. & Turner, D. H., Biochemistry 30, 10632–40 (1991)). Indirect methods rely on physico-chemical properties of the multimeric and single-stranded states, and include methods such as optical melting (Albergo, D. D. et al., Biochemistry 20, 1409–13 (1981)), and differential scanning calorimetry (Albergo, D. D. et al., op. cit.). These publications are incorporated by reference herein.

Kinetic measurements of on-rates ($k_1$) and off-rates ($k_{-1}$) use many of the same detection methods as equilibrium binding constant determinations, but rely on accurate correlations of species formation or disappearance with time. Off-rates can be studied by the direct methods described above, as well as indirectly by optical methods, and nuclear magnetic resonance of deuterium exchange of protons (Leroy et al, Journal of Molecular Biology 200, 223–38 (1988)). On-rates can be determined from $K_A$ and $k_{-1}$, using the equation $k_1=K_A \times k_{-1}$. Measurement of oligomer $k_1$ can be measured by specialized kinetic techniques such as temperature jump kinetics (Williams, A. P. et al., Biochemistry 28, 483–4291 (1989), and Turner, D. H. in *Investigations of Rates and Mechanisms of Reactions* 6, 141–189). The foregoing publications are also incorporated by reference herein.

It will be recognized, in light of the present disclosure, that the above preferred values for binding and kinetic constants will vary depending on the biological system in which the present oligonucleosides are being used. The values given above represent preferred values based on hybridization of the oligonucleoside to a single-stranded target sequence that does not have substantial secondary structure. Where the target sequence is located in a region of the mRNA molecule that has substantial secondary structure, the binding affinity of the oligonucleoside with respect to the secondary-structured target region may be much lower than that measured with respect to a non-structured (e.g., synthetic) target sequence having the same nucleoside sequence. In some cases the $K_A$ for the non-structured strand may be as much as $10^7$-fold greater than that of the structured strand. If the resulting $K_A$ with respect to the intended secondary-structured target is too low relative to, for example, a non-structured mismatch sequence, problems of specificity may result.

One preferred approach to this situation is to target a region in the target mRNA for RNaseH-mediated cleavage that does not have sufficient secondary structure to adversely affect the binding affinity of the subject oligonucleoside. The secondary structure of nucleic acids can be determined directly by the use of nucleases, base modification chemicals, or sugar-phosphate backbone modifying reagents, as recently reviewed by Jaeger et al., Annual Reviews in Biochemistry 62, 255–287 (1993). Another approach is to utilize two or more antisense compounds in tandem, at least one of which is a chimeric oligonucleoside of the invention, which antisense compounds have nucleoside base sequences selected to hybridize to adjacent regions in a secondary-structured mRNA target region. It is known that adjacently-hybridizing antisense compounds may be used to disrupt secondary structure of RNA molecules and thus to enhance the effective $K_A$'s of the respective compounds. By using this approach, cleavage of target mRNA regions having secondary structure may be achieved with specificity using oligonucleoside compounds having controlled binding affinity as taught herein.

As discussed above in the background section of this disclosure, a number of workers in the antisense field have reported various and disparate efforts to increase binding affinity of antisense oligonucleosides, to optimize RNaseH activation, to improve nuclease resistance, and to improve target specificity. It will be seen in light of the preceding detailed description that many of these approaches involve competing or conflicting considerations. For example, as just discussed, increased binding affinity is not always desirable in view of the problems it can create for target specificity. Certain structures that provide increased binding affinity, such as 2'-methoxy substitutions, or increased nuclease resistance, such as methylphosphonate internucleoside linkages, are seemingly incapable of activating RNaseH cleavage. Conversely, certain structures that provide high RNaseH activation, such as phosphodiester linkages, are nuclease-unstable while others, such as phosphorothioate linkages (and also phosphodiester linkages), may result in cleavage rates ($k_2$) that approach or exceed the mismatch "off rate" ($k_{-1}$), particularly in longer linkage sequences. The present invention provides improved oligonucleoside structures that address these competing considerations and meet other goals as described herein.

The oligonucleoside compounds of the invention comprise linked nucleosides having a base sequence that is complementary to a target region of the target ribonucleic acid sequence, and include an RNaseH-activating region and at least one non-RNaseH-activating region. When used in conjunction with mammalian RNaseH (e.g., in mammalian cellular systems), the RNaseH-activating region comprises, in the preferred embodiment, a segment of between 5 and about 9 consecutive 2'-unsubstituted nucleosides linked by 4 to about 8 charged (anionic) internucleoside linkage structures. When used in conjunction with bacterial RNaseH (e.g., in bacterial cellular systems or in antibacterial therapy in mammals), the RNaseH-activating region comprises, in the preferred embodiment, between 3 and about 7 consecutive 2'-unsubstituted nucleosides linked by 2 to about 6 charged internucleoside linkage structures.

The non-RNaseH-activating region comprises, in one preferred embodiment, a single segment of at least 3 linked nucleosides, and more preferably at least about 5 linked nucleosides, containing one or more chirally-selected $R_p$-linkages. In a related second preferred embodiment, the non-RNaseH-activating region comprises two separate flanking segments, each segment containing at least about 2 linked nucleosides, and more preferably at least about 4 linked nucleosides (or a total of at least about 8 linked nucleosides in the two separate segments), wherein one or more of the linkages is a chirally-selected $R_p$-linkage. The RNaseH-activating region is preferably flanked in the compound by two such separate non-RNaseH-activating regions. In a third related preferred embodiment, the non-RNaseH-activating region comprises an alternating sequence of racemic (non-chirally-selected) internucleoside linkages comprising (1) a racemic methyl- (or lower alkyl-) phosphonate (MP), methyl- (or lower alkyl-) phosphonothioate (MPS), aminoalkylphosphonate (AAP) or aminoalkylphosphonothioate (AAPS) linkage, alternating with (2) a negatively-charged phosphate, phosphorothioate or phosphorodithioate (e.g., DE, PS, or PS2) linkage. In any of the above embodiments, one or more of the nucleosides in the non-RNaseH-activating region may be 2'-substituted, particularly to increase binding affinity and nuclease resistance while controlling (selectively decreasing or eliminating) RNaseH-activation characteristics. It is particularly preferred that one or more, or all, phosphodiester linkages, if present in the non-RNaseH-activity region, be 2'-substituted, although further 2'-substitutions may also usefully be employed in the non-RNaseH-activity region.

As an example, the phosphonate internucleosidyl linkages used in oligomers of the present invention may contain a lower alkyl group replacing one of the two non-bonding (or non-bridging) oxygens on the phosphorus of a phosphodiester internucleosidyl linkage, wherein the other non-bonding oxygen remains or is alternatively replaced by sulfur. The replacement of oxygen by lower alkyl creates a chiral environment around the phosphorus which can be designated as either $R_p$ or $S_p$, depending on which of the non-bonding oxygens has been replaced with lower alkyl. The $R_p$ and $S_p$ configurations can be depicted as follows:

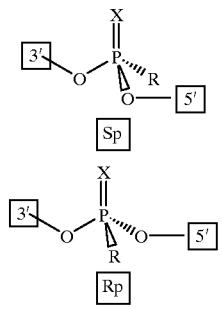

wherein X is oxygen or sulfur and R is lower alkyl.

Applicants have discovered that the binding affinity of the present RNaseH-activating oligonucleoside compounds can usefully be controlled by selectively incorporating into the compounds polynucleoside segments containing chirally-selected internucleoside linkage structures. Such chirally-selected $R_p$-rich segments afford greater binding affinity than the corresponding racemic sequences. Applicants have also discovered that selectively-increased binding affinity and improved nuclease resistance can be achieved in a practical fashion, with or without chiral enrichment, using multiple or repeated blocks or synthons comprising both charged (including phosphodiester) and uncharged (particularly racemic or chirally-selected methylphosphonate) internucleoside linkage structures. Such synthons preferably do not have more than one consecutive charged linkage structure in their sequence, particularly if the charged (anionic) linkage structure is a phosphodiester bond.

These controllable binding affinity polynucleoside segments of the invention provide the benefits of increased nuclease resistance, controllable RNaseH-activation characteristics and ease of synthesis. Thus, for example, the linkage structures can be chosen to include one or more uncharged modified (non-phosphodiester) linkage structures which will be substantially non-activating to RNaseH and also nuclease-resistant. Use of 2'-substituents as described herein also leads to increased nuclease resistance of segments including charged linkage structures, particularly phosphodiester linkages. Furthermore, individual synthons can be preliminarily assembled as synthetic blocks which are then readily combined to provide a controllable binding affinity segment containing two or more different block structures, or a single repeated block structure.

While the described technique of chiral selection can usefully be employed in both the RNaseH-activating and non-RNaseH-activating regions of the present compounds, it is most advantageously used in the latter region. In addition, chiral selection is preferably achieved with multiple or repeated mixed linkage structure blocks as described hereinafter.

A chirally-selected polynucleoside segment of the present invention includes a sequence of internucleoside linkage structures that is enriched or pure with respect to $R_p$ chiral linkages. Such a sequence is considered chirally-enriched if at least about 75% of the chiral (asymmetric) linkage structures in the segment, or alternatively at least about 40% of the total linkage structures in the segment, have $R_p$ chirality. As shown below, chiral enrichment of at least about 75% can be achieved synthetically by coupling a series of dimer nucleoside blocks (synthons) wherein the structure linking the two nucleosides of each synthon is a modified (non-phosphodiester) $R_p$-chiral linking structure, and wherein the linking structure between the respective synthons is asymmetric. The coupling reaction between synthons in the series will, in the simplest case, be carried out racemically, which means that about half of the inter-synthon linkages will be $R_p$-chiral and about 75% of all of the internucleoside linkages in the resulting mixed chiral/racemic segment will be $R_p$-chiral. (It should be noted that the "racemic" reaction may be driven more toward one diastereomer in particular cases; for example, investigations related to the present invention have shown that coupling of 2'-O-methyl-substituted methylphosphonate monomers leads preferentially to $S_p$-chiral internucleoside linkages.)

It will be seen that chiral enrichment in excess of 75% of the asymmetric linkages can be achieved by, for example, conjugating trimer nucleoside synthons wherein both internucleoside linkages within the block are $R_p$-chiral and the respective trimer synthons are conjugated racemically (or achirally). Synthetic schemes are shown below for the preparation of such trimer synthons. Alternatively, conjugation between individual nucleosides or between synthons can be carried out stereospecifically using asymmetric linkage structures, in which case all the linkages in the segment will be $R_p$-chiral. While it is not considered necessary to the preferred practice of the present invention to obtain segments having chiral enrichment in excess of about 75% of the asymmetric linkages (or about 40% of the total linkages), such highly-enriched segments will generally exhibit higher binding affinity characteristics.

As seen above, a mixed chirally-selected segment of the invention may include within it one or more achiral (non-asymmetric) linkage structures. Thus, in one preferred structure of the invention, a mixed chirally-selected segment is composed of alternating phosphodiester (achiral) and $R_p$-methylphosphonate (or other chiral) linkage structures. Such a repeated alternating linkage sequence segment can be prepared using dimer nucleoside blocks wherein the structure linking the two nucleosides of the block is an $R_p$-chiral methylphosphonate linkage structure, and where the blocks are conjugated achirally using a phosphodiester (or other achiral) linkage structure. It will be seen that a polynucleoside segment prepared in this manner will be chirally pure inasmuch as all of the chiral linkages in the segment are of the $R_p$ conformation, whereas substantially 50% of the total linkages will be $R_p$-chiral.

The inventors have ascertained in investigations relating to the invention that enrichment of methylphosphonate $R_p$ linkages gives an increase in melting temperature (Tm) of about 0.9 to 1.5° C. per internucleosidyl linkage that is in the $R_p$ conformation as compared to a random racemic conformation. This translates into an increase in binding affinity $(K_A)$ by a factor of about 1.8 for each additional selected $R_p$ linkage (or a factor of about 2.6 in the case of 2'-O-methyl-substituted residues). It will now be appreciated that, by the judicious use of chirally-selected linkage structure segments in the present compounds, binding affinity can be controlled in a manner consistent with the objectives set forth above in the detailed description. The examples below demonstrate that increased potency can be achieved with such chirally-selected compounds, as compared to racemic compounds, while maintaining specificity against the intended target sequence.

As explained above, another objective of the invention is to provide oligonucleoside structures having controlled RNaseH activation characteristics. This objective is obtained in the present invention by providing in the compound a non-RNaseH-activating polynucleoside region, or regions, having reduced RNaseH-activation capabilities, along with an RNaseH-activating region having sufficient RNaseH-activation capability to effect RNaseH-mediated cleavage of the target nucleic acid strand. Preferably, both of these segments of the compound are constructed to be nuclease resistant.

As is also explained above, one putative requirement of mammalian RNaseH activation is that the antisense compound must have a sequence of at least four or five consecutive charged (anionic) internucleoside linkage structures (or at least two such linkages in the case of bacterial RNaseH), wherein the linked nucleosides are 2'-unsubstituted. Conversely, in the practice of the present invention, the non-RNaseH-activating segment can usefully include uncharged linkage structures and/or 2'-substituents. By making use in the non-RNaseH-activating region of modified (non-phosphodiester) uncharged linkage structures such as those described herein, the present compounds achieve increased nuclease resistance. Moreover, the use of 2'-substituents as described herein leads to selectively controllable increases in binding affinity. Thus, the inventors have ascertained in investigations relating to the present invention that the use of 2'-O-methyl nucleosides in methylphosphonate-linked oligomers results in additional increases in $T_m$ of about 1° C. per substitution of 2'-deoxy with 2'-O-methyl nucleosides. Furthermore, the inventors have ascertained that the use of 2'-substituents on nucleosides linked by phosphodiester bonds also leads to increased nuclease resistance.

Consistent with these objectives, preferred 2'-substituents of the invention include lower (1 to about 3 carbons) alkoxy, allyloxy, and halo (preferably fluoro) substituents. A methoxy group is especially preferred. In general, 2'-substituents that are electron-withdrawing are useful in increasing the binding affinity and nuclease resistance of the present compounds, as such substituents are believed to create a 3'-endo conformation in the substituted sugar group.

It has further been discovered that a limited proportion of charged linkage structures, including phosphodiester linkages, may usefully be incorporated into the non-RNaseH-activating segment, particularly in a linkage sequence containing multiple or repeated blocks of charged and uncharged linkage structures. Such segments lead to controllable increases in binding affinity, nuclease resistance, and controlled RNaseH activation characteristics, and result in compounds having enhanced specificity for the intended target nucleic acid sequence.

Preferred linkage structures and 2'-substituents for the non-RNaseH-activating segments of the invention include the following:

MP(R)/DE
2'OMeMP(R)/2'OMeDE
MP(R)/2'OMeMP
MP(R) enriched
2'OMeMP (R) enriched
MP(R)/PS
2'OMeMP(R)/2'OMePS
MP(R)/PS2
2'OMeMP(R)/2'OMePS2
2'OMeMP/2'OMeDE
MP/2'OMeDE
MP(R)/PAm
2'OMeMP(R)/2'OMePAm
2'OMeMP/2'OMePAm
MP/2'OMePAm
MP(R)/TE
2'OMeMP(R)/2'OMeTE
2'OMeMP/2'OMeTE
MP/2'OMeTE
MP(R)/MPS
2'OMeMP(R)/2'OMeMPS
2'OMeMP/2 OMeMPS
MP/2'OMeMPS
MP(R)/PF
2'OMeMP(R)/2'OMePF
2'OMeMP/2'OMePF
MP/2'OMePF
MP(R)/PBH$_3$
2'OMeMP(R)/2'OMePBH$_3$
2'OMeMP/2'OMePBH$_3$
MP/2'OMePBH$_3$
MP(R)/RSi
2'OMeMP(R)/2'OMeRSi
2'OMeMP/2'OMeRSi
MP/2'OMeRSi
MP(R)/CH$_2$
2'OMeMP(R)/2'OMeCH$_2$
2'OMeMP/2'OMeCH$_2$
MP/2'OMeCH$_2$ Key:
MP = racemic methylphosphonate linkage (between linked nucleosides);
MP(R) = chirally-selected $R_p$-methylphosphonate linkage;
DE = phosphodiester linkage;
PS = phosphorothioate linkage;
PS2 = phosphorodithioate linkage;
PAm = phosphoramidate linkage;
TE = phosphotriester linkage;
MPS = alkyl (particularly methyl) phosphorothioate linkage;
PF = phosphorofluoridate linkage;
PBH$_3$ = boranophosphate linkage;
RSi = silyl (especially alkyl-disubstituted silyl) linkage;
CH$_2$ = formacetal linkage;
2'OMe = 2'-methoxy-substituted (or other lower alkoxy, allyloxy or halo suostituted) nucleoside residue, linked using the listed linkage structure;
"enriched" refers to a segment of linkages preferably containing at least about 40% (and up to 100%) $R_p$-selected linkages among the linkages in the segment, and thus includes a mixed seguence of racemic and chirally-selected R internucleoside linkage structures;
linkage structures grouped with slashes denote a mixed linkage segment including the listed linkage structures, optionally in a series of multiple or repeated mixed linkage sequence blocks.

Also preferred are compounds having a segment chosen from the above listing wherein one or more (or all) of the methylphosphonate (MP or MP(R)) linkages are replaced with lower alkyl-, especially methyl-, phosphonothioate (MPS or MPS(R)) linkages, or with aminoalkylphosphonate (AAP or AAP(R)) or aminoalkylphosphonothioate (AAPS or AAPS(R)) linkages. Such compounds include 2'-substituted residues containing such linkages, as well as compounds "enriched" in these $R_p$-chiral linkages. Examples of the latter include compounds having an alternating sequence of MP (racemic) and AAP(R) linkages, or an alternating sequence of MP(R) and AAP (racemic) linkages, or an alternating sequence of AAP (racemic) and AAP(R) linkages. Also preferred are compounds chosen from the above listing wherein one or more (or all) of the $R_p$-chiral methylphosphonate (MP(R)) linkages are replaced with racemic methylphosphonate (MP) linkages, preferably in an alternating sequence with a second different linkage structure, and most preferably in an alternating or other mixed sequence with phosphodiester, phosphorothioate or phosphorodithioate linkages.

Each of the mixed linkage segments listed above will contain at least one of each of the linkage structures listed. From a synthetic standpoint, it may be convenient to alternate the listed linkage structures or to use a repeated sequence containing both structures, although this is not necessary. Two or more of the mixed linkage segments listed above may be serially combined within a given non-RNaseH-activating region of the compound. In this case, it may be convenient from a synthetic standpoint to select discrete synthons from the respective mixed linkage groups and combine them in the single region.

Thus, it will be seen that the present invention provides synthetic oligomers having one or more segments including mixed internucleosidyl linkages, particularly oligomers having chirally pure or enriched phosphonate internucleosidyl linkages interspersed with single non-phosphonate internucleosidyl linkages and methods for their preparation. Such phosphonate internucleosidyl linkages include lower alkylphosphonate internucleosidyl linkages of 1 to 3 carbon atoms and lower alkylphosphonothioate (alkylthiophosphonate) internucleosidyl linkages of 1 to 3 carbon atoms. These mixed oligomer segments preferably have phosphonate internucleosidyl linkages interspersed between single non-phosphonate internucleosidyl linkages in a ratio of from 1 to about 1 to 1 to about 4 non-phosphonate linkages to phosphonate linkages. According to a preferred aspect, such oligomers have alternating chirally pure phosphonate internucleosidyl linkages which alternate with non-phosphonate internucleosidyl linkages. Oligomers comprising such segments, particularly in one or more non-RHaseH-activating regions, may be used to prevent or interfere with expression or translation of a single-stranded RNA target sequence. The chimeric oligonucleosides have an overall nucleoside base sequence, including the RHaseH-activating and non-RHaseH-activating regions, which is sufficiently complementary to the RNA target sequence to hybridize therewith.

Preferred chirally pure phosphonate linkages include $R_p$ lower alkylphosphonate linkages, and more preferred are $R_p$ methylphosphonate internucleosidyl linkages. Preferred non-phosphonate linkages include phosphodiester, phosphorothioate and phosphorodithioate, while phosphoramidate, phosphorofluoridate, boranophosphate, formacetal and silyl internucleosidyl linkages may also be used. According to an especially preferred aspect, $R_p$-enriched oligomers are provided having chirally pure $R_p$-methyl phosphonate linkages which alternate with phosphodiester linkages in the non-RHaseH-activating region of the compound. These alternating oligomers have been found to exhibit enhanced binding affinity for an RNA target sequence and also increased nuclease resistance and specificity.

The present invention likewise includes chimeric antisense oligomers having enhanced potency as antisense inhibitors of gene expression comprising one or more segments with methylphosphonate internucleosidyl linkages enhanced for the $R_p$ configuration which are interspersed between non-phosphonate internucleosidyl linkages, preferably phosphodiester or alternatively phosphorothioate or phosphorodithioate linkages. We have found that chirally enriched oligomers hybridize more tightly to RNA target sequences and should show enhanced potency inhibiting translation of RNA targets as compared with oligomers having racemic MP internucleosidyl linkages mixed with the same non-phosphonate internucleosidyl linkages.

As explained above, the RNaseH-activating region of the present invention can have varying minimum and optimum lengths depending on the species (mammalian or bacterial) of the RNaseH enzyme that is utilized for cleavage. In either case, the RNaseH-activating region preferably comprises a sequence of consecutive 2'-unsubstituted nucleosides linked by charged internucleoside linkage structures. Preferred linkage structures and mixed linkage structures for the RNaseH-activating region are selected from among the following:

---
DE
PS2
PS
PS2/DE
PS/DE
PS/PS2
---

One especially preferred linkage structure is the phosphorothioate (PS) linkage.

In a related embodiment, two oligonucleosides of the invention having terminally-positioned RNaseH-activating regions may be used in tandem to effect cleavage of a target mRNA site. The nucleoside base sequences of the respective compounds are selected to be complementary to adjacent regions in the target mRNA strand. The RNaseH-activating regions may be used in tandem to effect cleavage of a target mRNA site. The RNaseH-activating regions are situated at the 5'-terminus and the 3'-terminus of the respective compounds such that, upon co-hybridization to the adjacent regions in the target, the two RNaseH-activating regions abut one another and are hybridized to adjacent target subregions in the overall target region of the mRNA strand. The two RNaseH-activating regions act to complement one another with respect to RNaseH-mediated cleavage of the target region. Shorter RNaseH-activating regions may be used in the two compounds than might otherwise be required, and specificity should be increased to the extent that dual hybridization is required to effect cleavage.

Chimeric oligomers of the invention, or segments thereof, having a predetermined base sequence of nucleosidyl units and having chirally pure phosphonate internucleosidyl linkages mixed with non-phosphonate linkages wherein the phosphonate linkages are interspersed between single non-phosphonate linkages may be prepared by coupling to one another individual nucleoside dimers, trimers or tetramers of preselected nucleoside base sequence having chirally pure or racemic phosphonate or other internucleosidyl linkages.

In this regard, chirally pure or racemic synthons of the formula:

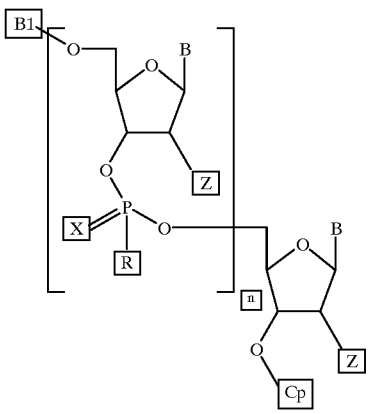

may be utilized wherein X is oxygen or sulfur, R is lower alkyl of 1 to 3 carbon atoms, B1 is a removable blocking group, Z is hydrogen, alkoxy of 1 to 10 carbon atoms, halogen or alkenyloxy of 3 to 6 carbon atoms; B is an optionally protected purine or pyrimidine base; n is 1, 2 or 3 and Cp is a coupling group. The coupling group Cp is conveniently selected so as to give the desired non-phosphonate internucleosidyl linkage when coupled to another synthon.

According to one preferred chirally-selective synthetic method, nucleoside dimers having a phosphonate linkage connecting the two nucleosidyl units of the dimer are prepared and separated into their $R_p$ and $S_p$ isomers. The resulting dimers which have a defined chirality at the phosphonate linkage, are then derivatized so that they may be coupled together using an automated DNA synthesizer. The dimers may have coupling groups which result in any one of a variety of internucleosidyl linkages between dimers. From a stock of 16 dimers, oligomer segments of any nucleoside base sequence may be synthesized by linking together the appropriate dimers. Dimers are added to the growing oligomer chain until an oligomer segment having the desired number of nucleosides is obtained. The resulting oligomer segment has a defined chirality at every other internucleosidyl linkage (i.e., those linkages originally derived from the coupled dimeric units). The remaining internucleosidyl linkages comprise non-phosphonate internucleosidyl linkages, such as phosphodiester, phosphorothioate, phosphorodithioate, morpholino, phosphoramidite, phosphorofluoridate, boranophosphate, formacetal, silyl or other non-phosphonate internucleosidyl linkages.

Alternatively, larger blocks of nucleosides such as trimers and tetramers may be coupled to give a chirally enriched oligomer. Trimers having two chirally pure internucleosidyl linkages may be conveniently prepared by coupling the appropriate chirally pure dimer synthon to another nucleoside and, for example, if $R_p$ chirality is to be selected, then separating the resulting $R_p$-$R_p$ and $R_p$-$S_p$ trimers. The resulting trimer has defined chirality (i.e., is chirally pure) at both inter-nucleosidyl linkages. The trimers are then derivatized to give trimer synthons so that they may be coupled together using an automated DNA synthesizer. The trimer synthons have coupling groups which allow them to be coupled together to give a chirally enriched phosphonate oligomer segment. From a stock of 64 trimers, oligomers of any base sequence may be synthesized by linking together the appropriate trimers. Trimers may be sequentially added to the growing oligomer chain or alternatively coupled with nucleoside monomers, dimers and/or tetramers until an oligomer segment having the desired number of nucleosides is obtained. The resulting chimeric oligomer has a defined chirality at those internucleosidyl linkages in the chirally-selected segment derived from the internucleosidyl linkages of the coupled chirally-selected dimers, trimers or tetramers. Thus, use of these trimers will result in an oligomer segment having phosphonate linkages of defined chirality at about two out of every three internucleosidyl linkages. By following analogous techniques, tetramers having three chirally pure internucleosidyl linkages may be prepared and coupled to each other or to other synthons (including monomers) to give other chirally-selected segments or portions thereof. Alternatively, dimers, trimers and other short oligomers having internucleosidyl linkages of defined chirality (such as pure $R_p$) may be coupled together or to other synthons in appropriate sequence to give an oligomer segment or portion thereof of a particular desired sequence and length. Such a chirally-selected segment can be coupled with additional nucleosides forming a separate segment of the compound, particularly a segment of consecutive 2'-unsubstituted nucleosides linked by charged linkage structures forming an RHaseH-activating region.

According to an alternative synthetic method, coupling conditions for nucleoside synthons (or dimers) are used which direct coupling to give an enhanced yield of the desired chiral-configuration. This method may be used to couple individual nucleoside synthons or alternatively the chirally pure dimers and, thus, obtained are oligomer segments, particularly non-RHaseH-activating segments, enriched for the desired chiral configuration at each of the phosphonate internucleosidyl linkages.

The chirally-selected methylphosphonate and other monomers, dimers, trimers and the like taught in the examples and Detailed Description herein can be coupled together by a variety of different methods leading to the following, non-exclusive, types of internucleosidyl linkages: phosphodiester, phosphotriester phosphorothioate, phosphorodithioate, phosphoramidate, phosphorofluoridates, boranophosphates, formacetal, and silyl.

Internucleosidyl phosphodiester linkages can be obtained by converting the 3'-OH of a chirally-selected or racemic synthetic unit (monomer, dimer, trimer, polynucleoside, etc.) to either a phosphotriester synthon (Reese, C. B. (1978) Tetrahedron 34, 3142–3179), phosphoramidite synthon (Beaucage, S. L. and Lyer, R. P. (1992) Tetrahedron 48, 2223–2311), H-phosphonate synthon (Froehler, B. C. in Agrawal, S., ed. Protocols for Oligonucleotides and Analogs, Synthesis and Properties, Methods in Molecular Biology Vol. 20, Humana Press, Totowa, N.J., 1993, pp. 63–80), or phosphoromonochloridite reagent (Hogrefe, R. I. (1987) dissertation, Northwestern University, Evanston, Ill.).

Internucleosidyl phosphorothioate linkages can be obtained by converting the 3'-OH of a synthetic unit to either a phosphotriester synthon (Stec, W. J., et al. (1991) Nucl. Acids Res. 19, 5883–5888)), phosphoramidite synthon (Lyer, R. P., et al. (1990) JACS 112, 1254–1255), H-phosphonate synthon (Seela, F. and Kretschmer U. (1991) J. Org. Chem. 56, 3861–3869), or phosphoromonochloridite reagent (Hogrefe, R. I. (1987) Dissertation, Northwestern University, Evanston, Ill.).

Internucleosidyl phosphorodithioate linkages can be prepared as by the disclosures herein and by U.S. Pat. No. 5,218,088 to Gorenstein et al. Internucleosidyl phosphotriester linkages can be obtained by converting the 3'-OH of a synthetic unit to either a phosphotriester synthon (Reese, C. B. (1978) Tetrahedron 34, 3143–3179), phosphoramidite synthon (Beaucage, S. L. and Lyer, R. P. (1992) Tetrahedron 48, 2223–2311), H-phosphonate synthon (Froehler, B. C. in Agrawal, S., ed. Protocols for Oligonucleotides and Analogs, Synthesis and Properties, Methods in Molecular Biology Vol. 20, Humana Press, Totowa, N.J., 1993, pp. 63–80), phosphoromonochloridite reagent (Hogrefe, R. I. (1987) Dissertation, Northwestern University, Evanston, Ill.), or post synthetically (see U.S. Pat. No. 5,023,243 to Tullis.

Internucleosidyl phosphoramidate, phosphorofluoridate, boranophosphate, formacetal, and silyl linkages can be obtained by converting the 3'-OH of a synthetic unit to the appropriate synthons. (See Agrawal, S., ed. Protocols for Oligonucleotides and Analogs, Synthesis and Properties, Methods in Molecular Biology Vol. 20, Humana Press, Totowa, N.J., 1993, for synthetic protocols to obtain synthons for each of the above.)

Chemical structures for synthons and reactive intermediates useful in the present invention are depicted in FIGS. 6–10, and are discussed in further detail in U.S. patent application Ser. Nos. 08/154,013 and 08/154,014.

The present invention also includes the discovery that the sequence of nucleoside bases in the present chimeric RNaseH-activating compounds, and also the sequence of bases in RNaseH-activating antisense compounds generally, can be selected in a manner described herein to provide RNaseH-activated cleavage that is highly specific to disease conditions caused by singular (particularly single-base) mutations, allele differences or other anomalies in genetic sequence. In particular, the inventors have discovered antisense oligonucleoside constructions that are capable of discriminating a single base difference in a target RNA sequence occurring at a base position corresponding to that of a non-target RNA sequence, such that RNaseH-mediated cleavage is specific to the target sequence and the non-target sequence is substantially unaffected.

In this regard, antisense oligonucleosides have reportedly been used to target a wide variety of mRNAs associated with cancer and other diseases. See, for example, Stein, C. A. and Cheng, Y. C., Science, 261, 1004–1012 (1993); Uhlmann, E. and Peyman, A., Chemical Reviews, 90, 544–584 (1990). One challenge in the application of antisense oligonucleosides as therapeutic agents is the need to discriminate a single base difference between target and non-target sequences. A number of cancer-causing genes, for example, have been identified which differ from their normal counterparts by only a single base change, including the RAS, p53, src and erbB-2 oncogenes. Single base changes are also associated with some inherited genetic diseases such as Lesch-Nyhan syndrome (Fujimura, S. et. al, Human Genetics, 90, 385–388 (1992)), platelet diseases (Takahashi, H. et. al., Blood, 85, 727–733 (1995)) and diabetes, Repaske, D. R. and Phillips, J. A., Prog. Brain Res., 93, 295–306 (1992) as well as a large number of other genetic diseases.

The ability to discriminate single base differences between two related sequences also makes it possible to selectively target single alleles. It is estimated that single base changes occur every few thousand base pairs within the human genome. These base changes often produce corresponding mRNA sequences that likewise contain different bases a single sites. With knowledge of these base differences, oligonucleotides capable of discriminating such base changes can be employed to selectively block the activity of one allele while having minimal or no effect on related alleles. Depending upon the disease mechanism, single allele targeting can be employed to selectively affect the growth, expression, or survival of cells associated with various diseases including cancer and genetic diseases. This is the case even if the targeted allele is not directly associated with disease causation, as long as it is associated uniquely with the growth, expression, or survival of the disease or cancer cells.

In the past, single base discrimination has been approached by using short oligonucleosides in the range of 10–14 bases which have relatively poor affinity constants for their targets. As a result, the destabilizing effect of a single mismatch causes a proportionally large decrease in the affinity of such oligonucleosides for their complementary sequences. There are two primary problems associated with this approach. First, it leads to poor potency of the therapeutic oligonucleoside and the need to use higher concentration of drug to fully bind the target sequence; and second, it may result in insufficient specificity because of the greater likelihood that other non-targeted sequences may exist that are complementary with oligonucleosides that are this short.

Ideally, and within the constraints described in the specification above, antisense oligonucleosides should have high affinities with their target sequences, so that small amounts of oligonucleoside can be used for treatment. In addition, the oligonucleosides should be sufficiently long so as to minimize the chance that a complementary sequence occurs at sites within the array of expressed mRNA sequences other the intended target site. At the same time, it is advantageous that the oligomer should be able to discriminate between target and non-target sequences that differ at known sites by a single nucleotide. All of these requirements can be achieved by employing the RNaseH active oligonucleosides embodied in this invention. The chimeric oligomers described herein are of sufficient length and composition to have high affinity with their desired targets, which leads to good drug potency. Due to their length, these constructions also describe unique target sequences. Most importantly though, the described chimeric oligomers contain RNaseH active domains in which single mismatched base pairs, when properly positioned, can render the chimera virtually completely inactive. Thus, these chimeric oligomers make possible the construction of higher binding affinity therapeutic agents that can precisely discriminate between target and non-target sequences that differ at known sites by only a single base change, including disease-related target sequences having a single base change such as those noted above.

As further described in Examples 50(a) and 50(b) below, the inventors have discovered that such high-specificity chimeric oligomers can be achieved by carefully defining the position of the RNaseH-activating region within the overall base sequence of the antisense oligomer. Particularly, the oligomer is selected, first, to have a base sequence that is complementary to a target region of the target RNA sequence containing a single base change that distinguishes the target RNA sequence from non-target RNA sequences. The particular base in the target RNA sequence that defines this single base change (as compared to non-target sequences) is referred to herein as the "RNA target base." Likewise, the nucleoside base in the chimeric oligomer that is complementary to the target RNA base is referred to herein as the "targeting oligonucleoside base." It will be seen that the targeting oligonucleoside base introduces a mismatch with respect to the non-target RNA sequences, the mismatch occurring at the position corresponding to the single base change. The particular base in a non-target RNA sequence that defines this mismatch (as compared to the targeting oligonucleoside base) is referred to herein as an "RNA non-target base."

It has been discovered that the high-specificity cleavage effect described herein can be achieved by selectively positioning the targeting oligonucleoside base near the 5'-end of the RNaseH-activating region of the chimeric oligomer. The optimal positioning will generally depend on factors such as the particular RNaseH enzyme present (e.g., mammalian enzyme versus bacterial enzyme) and, perhaps, the particular RNA base sequence in the target (including the identity of the target RNA base and the mismatch base on the non-target RNA). Optimal positioning can be ascertained with routine experimentation using the present teachings.

Where a mammalian RNaseH enzyme (such as HeLa or other endogenous mammalian RNaseH enzyme) is utilized for cleavage, it is presently preferred that the targeting oligonucleoside base be positioned at the first, second or third nucleoside from the 5'-end of the RNaseH-activating region, and often most preferably the second nucleoside. Here, the base numbering of the RNaseH-activating region starts with the 5'-most 2'-unsubstituted nucleoside of the region, which is linked on its 3'-side by a charged internucleoside linkage structure to the remainder of the RNaseH-activating region, and on its 5'-side by another charged linkage structure to the remaining 5'-flanking portion of the oligomer (if present).

Experiments using compounds of the present invention (see Examples 50(a) and 50(b) below) have shown that the most active RNaseH cleavage sites differ between mammalian RNaseH and bacterial RNaseH. Particularly, use of mammalian (HeLa) enzyme causes cleavage most rapidly at RNA phosphodiester linkages directly across from the 5'-most charged linkage structures in the RNaseH-activating region of the duplexed oligomer, while use of bacterial (E. coli) enzyme shifts the preferred RNA cleavage site in the 3'-direction by two linkage positions. Thus, in the case of the bacterial RNaseH enzyme, the preferred RNA cleavage site may fall at a phosphodiester linkage position that is slightly outside the 5'-end of the corresponding RNaseH-activating region of the duplexed oligomer.

In view of this shift in preferred cleavage position occurring with bacterial RNaseH, it is presently preferred in such systems that the targeting oligonucleoside base be positioned at the first nucleoside at the 5'-end of the RNaseH-activating region, or at the first nucleoside outside the 5'-end of that region. However, as noted above, optimal placement of the targeting oligonucleoside base can be readily ascertained and modified for a particular oligomer-target pair given the teachings of the present disclosure.

The high cleavage specificity of such oligomer structures can be achieved using a variety of oligomer constructs within the scope of the invention. Preferably, the non-RNaseH-activating region(s) of the oligomer will incorporate nuclease-resistant linkage structures as described above, including chirally-selected linkages. However, in view of the high specificity of these constructs toward RNA target sequences containing only a single base change from non-target sequences, the use of chiral selection to selectively control binding affinity is not required (although it may be usefully employed to increase binding affinity or potency if desired in a particular case).

It is also advantageous in this context to use a central RNaseH-activating region flanked by two terminal non-RNaseH-activating regions, especially where the latter regions are selected to afford nuclease (particularly exonuclease) resistance. In many in vivo systems of interest, however, it is believed that 3'-exonucleases present greater degradation problems than 5'-exonucleases, and dual flanking regions may not be necessary.

It is desirable that the present RNaseH-activating regions contain fewer than 7 nucleosides, and preferably 3 to 5 nucleosides, so that the region presents but a single, uniquely-defined site for RNaseH cleavage. This minimizes the possibility of RNaseH-mediated cleavage at adjacent sites in non-target RNAs, i.e. sites that are unrelated to the single base change that is being targeted. The size of the non-RNaseH-activating region(s) can readily be selected using the principles described above so as to achieve suitable binding affinity and other desired properties.

The relative positions and sizes of the RNaseH- and non-RNaseH-activating regions within the overall sequence of the oligomer may also be chosen so as to enhance cleavage of RNAs having secondary structure in the region of the RNA target base. For example, if the RNA target base is located in a non-structured sequence closely upstream (5') from a secondary structure in the target RNA, then it may be desirable to utilize an oligomer of the invention having its RNaseH-activating region close to the 5'-end of the oligomer, with no lengthy 5'-terminal flanking region that might interfere with hybridization close to the secondary structure. In this case a relatively lengthy 3'-terminal flanking region may be used to afford suitable binding affinity and binding specificity. Similar design considerations will be recognized where the RNA target base is located closely downstream (3') from a target RNA secondary structure.

The present compounds may be used in the formulation of pharmaceutical compositions for treatment of animal diseases associated with single base changes in RNA sequences, and in related methods of treatment. Such treatment methods include in vivo treatment by administration of the chimeric oligomer to the subject animal, as well as ex vivo methods wherein, for example, cells or tissues are removed from the subject, treated with oligomer, and returned to the patient.

In addition, the compounds may be used in the diagnosis (especially in vitro diagnosis) of such diseases and, more generally, in detecting in an animal test sample the presence of RNA sequences containing a single base change of interest. In this regard, the present compounds are applied to the test sample and the generation of cleavage products is monitored using methods known in the art. Because of the high cleavage specificity of the oligomer compounds, it is possible to confirm, from the presence (or absence) of cleavage products, the presence (or absence) of the target sequence of interest even where similar RNA sequences varying in a single base position coexist in the test sample.

The following examples demonstrate various significant aspects of the present invention, but are examples only, and should not be considered as limiting the scope of the present invention.

EXAMPLES

Example 1

Preparation of MP($R_p$)/DE and MP($R_p$)/MP Dimer Synthons

A. Preparation of a (CT) Dimer Having a Chirally Pure Methylphosphonate Internucleosidyl Linkage Using Solution Phase Chemistry Into a 2 L roto-evaporator flask was placed 10.0 g (28 mM) of 3'-tert-butyldimethylsilyl thymidine and 26.1 g (35 mM) of 5'-dimethoxytrityl-$N^4$-isobutyryl-3'-methyl-N,N-diisopropylaminophosphoramidite-2'-deoxycytidine. The solids were dissolved in 500 ml of acetonitrile and evaporated to dryness under vacuum. This process was repeated with another 500 ml of acetonitrile and then the flask was released under argon and stoppered with a rubber septa.

This dry solid foam was then dissolved in 500 ml of acetonitrile ("ACN"), and with manual stirring, treated all at once with 404 ml tetrazole (180 mM, 0.45 M tetrazole in THF). Manual stirring is continued for 30 seconds and then the flask is allowed to stand for another 2.5 minutes, after which time the reaction mix is treated all at once with 275 ml of an oxidizer solution ($I_2$/$H_2O$/lutidine/THF; 25 g/2.5 ml/100 ml/900 ml). The solution was stirred manually and allowed to stand at room temperature for 15 minutes. The resulting dark amber solution was then treated with bisulfite (2 g/25 ml $H_2O$), which upon addition, turned the solution light amber as it reacted with the excess iodide. The reaction mix was then concentrated to a thick oil and taken up in ethyl acetate ("EtOAc") (500 ml) and washed with saturated sodium bicarbonate (2×250 ml) and $H_2O$ (2×250 ml). The organic phase was dried over $MgSO_4$, filtered and concentrated to a light colored solid foam, which upon further drying yielded 35 grams of crude dimer.

The crude dimer was run on HPLC (reverse phase, Waters C18 bondapak) with a program (ACNMETH) starting with 50% acetonitrile and 0.1 M triethylammonium acetate (TEAA, pH~7.0) which increased to 100% acetonitrile over 20 minutes with a linear gradient. Two major peaks were resolved, one at 4.5 minutes, which is residual lutidine and the other at 14.5 minutes which is the mixture of $R_p$ and $S_p$ diastereomers. The ratio of $R_p$ and $S_p$ was determined quantitatively by taking a 5 mg aliquot of the crude product and dissolving it in 1.5 ml of acetonitrile along with 0.5 ml of tetrabutylammonium fluoride (TBAF, 1 M solution in THF). After standing at room temperature for 10 minutes the sample was run on HPLC. Two new peaks were observed at 6.5 and 7.1 minutes and the later eluting peak was gone. The first new peak, which is believed to be the $S_p$ diastereomer, represented 66% (2/1) of the normalized value for the two peaks. The crude product was also analyzed by the (normal phase silica plate) in 75/25 EtOAc/$CH_2Cl_2$ ("75/25") with 5% methanol added. The TLC showed two spots with Rf's of 0.45 and 0.64, respectively; the faster running product (believed to be the $R_p$ form) was less intense than the slower moving one.

The $R_p$ diastereomer was separated on normal phase silica using a methanol step gradient in 75/25 EtOAc/$CH_2Cl_2$. A 7.5 cm by 60 cm column, was loaded with 700 g of silica (first slurried in 2.5 L of neat 75/25 EtOAc/$CH_2Cl_2$). The crude dimer was then dissolved in 75 ml of 75/25 EtOAc/$CH_2Cl_2$ and loaded onto the column. The column was started with 1% methanol and increased to 2% and finally 3% where the $R_p$ dimer began to elute. The $R_p$ dimer eluted cleanly over several bed volumes while maintaining 3% methanol in the eluent. The $S_p$ dimer was eluted later with 30% methanol. The $R_p$ dimer yield was 11.0 grams, while the $S_p$ yield was 17.8 grams. HPLC analysis (ACNMETH) was performed on the $R_p$ dimer and one peak was observed at 14.5 minutes. The TLC (75/25 EtOAc/$CH_2Cl_2$, 5% methanol) of this product, revealed a single spot product with an Rf of 0.55 which, upon treatment with 10% sulfuric acid in ethanol and heat, was both trityl and sugar positive.

The newly resolved $R_p$ dimer, 11.0 g (0.011 M) was dissolved in 110 ml of ACN and treated all at once at room temperature with 22 ml of TBAF (0.022 M, 1 M in THF). The reaction mixture was allowed to stand overnight at ambient temperature. The next morning the reaction was determined to be complete by TLC (75/25, EtOAc/$CH_2Cl_2$ with 10% methanol); no starting material was detected but a small amount of 5'-DMT-dT was observed, which runs considerably faster on normal phase silica than the 3'-OH of the dimer. The reaction mixture was concentrated on a rotary evaporator to a thick oil which was then dissolved in $CH_2Cl_2$ (200 ml) and washed with saturated sodium bicarbonate (2×100 ml) and $H_2O$ (2×100 ml). The organic phase was dried over $MgSO_4$, filtered, and concentrated to a light yellow solid foam, which was purified on 100 grams of silica (75/25, EtOAc/$CH_2Cl_2$ with 5% methanol). The 5'-DMT-dT was removed but an impurity at 13.5 minutes (HPLC, ACNMETH) was detected which was first believed to be unreacted starting material (t-BDMS on) but after additional treatment with TBAF this was found not to be the case. A second column, using 100 g of silica and the same eluent was run and smaller fractions were taken; the column was able to successfully separate the two spots. The pure CT-$R_p$ dimer fractions were pooled and concentrated to yield 5.5 grams of a nearly white solid foam.

B. Preparation of a Chirally Pure (CT) MP($R_p$)/DE Dimer Synthon

Into a 100 ml round bottom flask was placed 0.5 g (0.55 mMol) CT-3'-OH dimer (product of Example 1A) which was rendered anhydrous by 3×20 ml co-evaporations with pyridine. The flask was released from the vacuum system under argon gas and stoppered with a rubber septa. The compound was redissolved in 10 ml acetonitrile and 200 μl (1.4 mMol, 2.5 eq) TEA were added. To the resulting mixture at room temperature and with manual stirring, was added in one portion 200 μl (0.90 mmol, 1.6 eq.) 2'-cyanoethyl-N,N-diisopropylchlorophosphoramidite. The reaction mixture was allowed to sit at room temperature before being analyzed by reverse phase HPLC. The HPLC (Beckman System Gold, C18 bondapak, ACN method; Solution A was 50/50 ACN/0.1 M TEAA in water, pH 7 and Solution B was ACN; a gradient of 0 to 100% Solution B was run at a rate of 1 ml/minute over 25 minutes) showed complete conversion of starting material and a crude purity of greater than 90 percent. The diastereomers of the phosphoramidite were not resolved. The reaction mixture was concentrated under vacuum to a light yell solid foam. The foam was purified immediately by chromatography on 20 g of normal flash grade silica equilibrated with 5/1/5 ethyl acetate/acetonitrile/methylene chloride with 2% TEA to give 0.5 g (82% yield) of the above-identified product as an off-which solid foam having a purity of 99.3% as determined by HPLC.

C. Preparation of a Chirally Pure (CT) MP($R_p$)/MP Dimer Synthon

The CT-3'-OH dimer, 5.5 g (6 mM), prepared as described in part A above, was rendered anhydrous with two co-evaporations with pyridine. The resulting solid foam was released from the rotary evaporator with argon and stoppered with a rubber septa. The solid foam was dissolved in 100 ml of 9/1, ACN/$CH_2Cl_2$, then treated with 1.7 ml triethylamine (TEA, 12 mM). With magnetic stirring, the reaction mix was treated dropwise at room temperature with 1.5 ml chloromethyl-N,N-diisopropylamino phosphine (Cl-MAP, 8 mM). The reaction was monitored on HPLC (ACNMETH) and after 1.5 hours was complete, showing two main products, one at 3.5 minutes which was pyridine and a second at 14.3 minutes which was the desired amidite.

The reaction mixture was concentrated on a rotary evaporator using a partial vacuum; the flask which contained the resulting light amber sludge was released under argon and capped. The crude product was immediately passed through a flash column containing 60 grams of silica (first equilibrated in 1/1/1 ACN/EtOAc/CH$_2$Cl$_2$ with 3% TEA). The product was eluted quickly with this eluent and all U.V. positive fractions were pooled and concentrated. The resulting solid foam was co-evaporated with ACN to remove any residual TEA, then dried overnight under full vacuum. The final product, an off white solid foam, weight 5.0 grams.

Example 2

Preparation of (CU) 2'-O-Methyl MP(R$_p$)/2'-O-Methyl DE and 2'-O-Methyl MP(R$_p$)/2'-O-Methyl MP Dimer Synthons A. Preparation of 2'-O-Methyl C Monomer A 5.0 g (8 mmol) portion of 2'-O methyl cytidine was rendered anhydrous with pyridine co-evaporations (3×25 ml) and then dissolved in 50 ml acetonitrile. The solution was treated with 1.65 ml triethylamine ("TEA") (12 mmol, 1.5 eq.) and cooled in an ice bath. The solution was then treated with dropwise addition of 1.65 ml chloromethyl-N,N-diisopropylamino phosphine ("Cl-MAP") over two minutes. The ice bath was removed and the reaction mixture stirred for two hours. The reaction mixture (reaction was determined to be complete by HPLC) was concentrated to dryness. The residue was dissolved in 20 ml ethyl acetate/heptane (1:1) with 4% TEA, then loaded onto 40 g silica gel equilibrated with the same solvent system. All UV absorbing eluent from the column was collected and pooled, then concentrated to give 5.5 g of the above-identified product (yield about 90%).

B. Preparation of Silyl-Protected 2'-O-Methyl Uridine

Into a 250 ml round bottom flask was placed 5.0 g (9.0 mmol) 5'-DMT, 2'O-methyl uridine which was rendered anhydrous with dimethylformamide (DMF) co-evaporations (3×25 ml). The resulting dry foam was taken up in 50 ml DMF, then treated all at once with 2.4 g (35 mmol, 3.9 eq.) imidazole, followed by dropwise addition of 3.0 ml (12 mmol, 1.3 eq.) t-butyldiphenylsilyl chloride. The reaction mixture was stirred at room temperature overnight.

The progress of the reaction was checked by HPLC (ACN method (Solution A was 50/50 ACN/0.1 M TEAA in water, pH 7 and Solution B was ACN; a gradient of 0 to 100% Solution B was run at a rate of 1 ml/minute over 25 minutes) and thin layer chromatography ("TLC") using 5% methanol in methylene chloride, and determined to be complete (no starting material was evident). The reaction mixture was then poured into ice water and taken up in methylene chloride, then washed several times with aqueous sodium bicarbonate and water. The organic phase was dried over magnesium sulfate, filtered and then concentrated to give 7.2 g of a solid foam which gave a single spot on TLC. The solid foam was then dissolved in 70 ml methylene chloride and treated (with rapid magnetic stirring) all at once with 70 ml benzene sulfonic acid, 2% by weight in 2:1 methylene chloride/methanol. After stirring for 15 minutes at room temperature, the reaction mixture was quenched with 10 ml TEA. The resulting detritylated compound was stripped down to a thick amber oil which was then loaded onto 150 g. silica gel equilibrated in heat methylene chloride. The product was eluted from the column using 2% methanol (in methylene chloride). After drying, 3.51 g of the above identified product were obtained (yield about 80%).

C. Preparation of (CU) 2'-O-Methyl MP(R$_p$) Dimer

The silyl-protected 2'-O-methyl uridine monomer (product of Example 2B) (3.0 g, 6 mmol) was taken up in 30 ml anhydrous ACN. The 2'-O methyl cytidine amidite monomer (product of Example 2A) (5.5 g, 7 mmol, 1.2 eq.) separately, was taken up in 55 ml ACN. Both solutions were allowed to stand over 3 Å molecular sieves overnight at room temperature.

The two solutions were carefully decanted into a single flask and treated with 94 ml tetrazole (0.45 M in ACN, 42 mmol, 7 eq). The resulting mixture was stirred for 4 minutes and then oxidized by addition of 1.5 ml (1.2 eq.) cumene hydroperoxide. The reaction mixture was concentrated to dryness, then taken up in methylene chloride and washed with aqueous sodium bicarbonate and water. The organic phase was dried over magnesium sulfate, filtered and concentrated to give 7.5 g. of a solid foam. The diastereomeric ratio as determined by HPLC by comparison of areas under peaks was 57/43 S$_p$ to R$_p$.

The R$_p$ diastereomer was isolated by column chromatography using two silica columns (100:1, silica to crude product, equilibrated in 3:1 ethylacetate/methyl chloride with an increasing methanol gradient from 1 to 5%). A total of 1.07 g of pure R$_p$ dimer was isolated.

D. Deprotection of (CU) 2'-O-Methyl Dimer

A 1.07 g (0.90 mmol) portion of the 2'-O methyl CU dimer (product of Example 2C) was dissolved in 10 ml THF and treated all at once with 1.5 ml (1 m in THF, 1.5 eq.) tetrabutylammonium fluoride ("TBAF"). The reaction mixture was stirred at room temperature of r 30 minutes after which time HPLC revealed complete deprotection of the silyl group had been achieved. The reaction mixture was concentrated and the concentrate purified on 10 g silica gel, eluting with 3:1 ethyl acetate/methylene chloride with 5% methanol. The clean fractions were concentrated to give 550 mg of the above-identified pure 5'-OH dimer.

E. Preparation of a Chirally Pure (CU) 2'-O-Methyl (MP/DE) Dimer Synthon

A 230 mg portion of 2'-O-methyl CU 3'-OH dimer (product of Example 2D) was rendered anhydrous by 2×5 ml co-evaporations in ACN. The resulting dry solid foam was dissolved in 2.5 ml ACN and then 73 µl (2.5 eq.) triethylamine ("TEA") and 94 µl (2.0 eq.) 2'-cyanoethyl-N,N-diisopropyl chlorophosphoramidite (ACNE) were added. The reaction mixture was stirred at room temperature for 2 hours at which time HPLC analysis determined the reaction to be complete. The reaction mixture was dissolved in eluent (3/1/1 ethylacetate/acetonitrile/methylene chloride with 4% TEA) and loaded onto 2 g silica gel equilibrated with 3/1/1 ethylacetate/acetonitrile/methylene chloride with 4% TEA. The column was run using 3/1/1 ethylacetate/acetonitrile/methylene chloride with 1% TEA. The clean fractions, 3 to 25, were concentrated, redissolved in acetonitrile and concentrated again to a solid foam. The foam was dried overnight under full vacuum to give 200 mg of the above-identified product.

F. Preparation of Chirally Pure (CU) 2'-O-Methyl MP(R$_p$)/MP Dimer Synthon

Into a 100 ml round bottom flask was placed 400 mg (0.372 mmole) of 2'-O methyl CU dimer (product of Example 2D); it was rendered anhydrous by 1×5 ml co-evaporation with acetonitrile. The dry foam was then released from the vacuum system under argon gas, dissolved in 4 ml ACN and stoppered with a rubber septa. The solution was treated with 2 equivalents TEA (103 µl, 0.744 mmol), followed by 1.75 equivalents chloro-methyl-N,N-diisopropyl phosphine ("Cl-MAP") (118 µl, 0.651 mmol). The reaction mixture was stirred for 1 hour at room temperature, after which time HPLC showed about 50/50 starting material/product. An additional 50 µl TEA and 70 µl Cl-MAP were then added and the mixture stirred for an hour. When HPLC showed only 80% conversion, an additional 30 µl TEA and 30 µl Cl-MAP were added and the resulting mixture stirred another hour. At this time HPLC revealed 6% starting material. The reaction mixture was concentrated to dryness. The residue was dissolved in 500 ml 3/1/3 ethylacetate/acetonitrile/methylene chloride with 4% TEA and loaded onto 5 g silica equilibrated in the same solvent system. Fractions were collected. The early fractions were contaminated with a yellow impurity and, thus, were pooled and concentrated separately. The product from those fractions was then repurified by chromatography using the same conditions and pooled with the clean product isolated from the first column. The combined products were co-evaporated with ACN (3×5 ml) and dried overnight under full vacuum to give 350 mg (77% yield) of the above identified product which HPLC showed to be 95.5% pure.

Example 3

Preparation of 2'-O-Methyl MPS($R_p$)/2'-O-Methyl-DE and 2'-O-Methyl MPS($R_p$)/2'-O-Methyl-MP Dimer Synthons These dimer synthons are prepared by following the procedures described in Example 2, except that in Paragraph C, an equivalent amount of 3H-1,2-benzodithiole-3-one, 1,1-dioxide (Beaucage reagent) is substituted for cumene hydroperoxide. The procedures of Paragraphs 2E and 2F, respectively, lead to the phosphodiester and methylphosphothioate linkage combinations.

Example 4

Preparation of MPS($R_p$)/DE Dimer Synthons

These dimer synthons are prepared by following the procedures of Example 1, except in Paragraph A, an equivalent amount 3-H-1,2-benzodithiole-3-one, 1,1-dioxide (Beaucage reagent) is substituted for the oxidizer solution ($I_2$/$H_2O$/lutidine/THF).

Example 5

Preparation of MP($R_p$)/PS2 Dimer Synthons

The MP($R_p$)/PS2 dimer synthons are prepared as follows. Isometrically pure $R_p$ dinucleosides having a free 3'-OH are prepared according to the methods described in Example 1A. The dinucleoside is converted to the corresponding thiophosphoramidite using procedures such as those of Plotto et al. (Plotto et al, Tetrahedron 47:2449–61 (1991)) or Gorenstein et al., U.S. Pat. No. 5,218,088. The dinucleoside is co-evaporated three times with anhydrous pyridine, followed by three co-evaporations with toluene. A portion of dinucleoside (10 mmoles) is dissolved in 200 ml anhydrous dichloromethane, then three equivalents of anhydrous diisopropylethylamine followed by 1.5 equivalents of chloro-N,N-diisopropylaminothiomethoxyphosphine are added at 0° C. with stirring. The reaction is monitored by TLC until determined to be complete.

The product is worked up and purified using the procedures of Example 1B for isolation of the MP($R_p$)/DE phosphoramidite.

Example 6

Preparation of MPS($R_p$)/PS2 Dimer Synthons

The MPS($R_p$)/PS2 dimer synthons are prepared as follows. The isometrically pure $R_p$ dinucleoside with a free 3'-OH is prepared according to the methods of Example 4. Using the dinucleoside, the dimer synthon is prepared by the methods of Example 5.

Example 7

Preparation of MPS($R_p$)/2'-O Methyl DE Dimer Synthons

The MPS($R_p$)/2'-O-methyl DE dimer synthons are prepared using procedures analogous to those of Examples 1 and 3 but using the appropriate protected 2'-deoxynucleoside and protected 2'-O-methyl nucleosides.

Example 8

Preparation of a Poly-CT Oligomer Having Alternating MP($R_p$)/DE Internucleosidyl Linkages An oligomer having the sequence 5'-(C*T)-(C*T)-(C*T)-(C*T)-(C*T)-(C*T)-(C*T)-A-3' SEQ ID NO:1 was prepared using * a CT MP($R_p$)/DE dimer synthon prepared according to Example 1. The grouped dinucleosides indicate where the stereochemistry is fixed as the fast eluting isomer on silica gel (putative $R_p$) and the asterisks indicate the chirally pure linkages.

Manual couplings were used to synthesize the oligomer to conserve reagent, although the process can be done on an automated DNA synthesizer. The sequence was synthesized from the 3'-terminus starting with methacrylate support bound deoxyadenosine.

The protected dinucleoside methylphosphonamidite (22 mg each per required coupling) freshly co-evaporated with pyridine and toluene to ensure dryness were placed into dried 1 ml glass autosampler vials and dissolved in anhydrous acetonitrile to a concentration of 0.1 M (200 µl per coupling). The vessels were purged with argon and tightly sealed with screw caps with teflon septa.

A 1 µmole scale DNA synthesis column (Milligen) was filled with 1 µmole of methacrylate support bound deoxyadenosine. The column was attached to a ring stand in a vertical orientation. A male-male luer fitting was attached to the bottom along with an 18 gauge needle to control the effluent. The column was washed with 10 ml acetonitrile using a syringe. The support bound nucleoside was detritylated by passing 3 ml of 2% dichloroacetic acid in dichloromethane through the column over 1.5 minutes. The orange, dimethoxytrityl cation bearing solution was reserved. The column was washed twice with 10 ml each of anhydrous acetonitrile.

The first coupling was accomplished as follows: 10 ml more anhydrous acetonitrile was passed through the column. Then, 200 µl of the CT methylphosphonamidite was drawn into a 1 ml syringe. Next, 200 µl of 0.45 M tetrazole in anhydrous acetonitrile was likewise drawn into the syringe containing the methylphosphonamidite. The reagents were rapidly mixed in the syringe, then slowly passed through the column dropwise over three minutes, being sure to lightly draw the plunger up and down to ensure adequate mixing with the support. After 3 minutes, 1 ml of the oxidizing reagent (0.1 M $I_2$ in 73% tetrahydrofuran, 25% 2,6-lutidine and 2% water) was passed through the column over one minute. The column was washed with 20 ml acetonitrile and then treated with 600 µl of a solution containing 20% (v/v) acetic anhydride, 30% (v/v) acetonitrile, 50% (v/v) pyridine and 0.312% (w/v) dimethylaminopyridine. The column was then washed with 20 ml acetonitrile.

The above-described synthetic cycle was repeated until the synthesis was completed. The overall coupling efficiency based on dimethoxytrityl absorbance was 95.7%, for an average of 99.3% per coupling.

The oligomer was then cleaved from the support and deprotected. The support bound oligomer was removed from the synthesis cartridge and placed in a glass 1 dram vial with a screw top. The support was treated for 30 minutes at room temperature with 1 ml of a solution of acetonitrile/ethanol/ $NH_4OH$ (9/9/1). Then, 1 ml of ethylenediamine was added to the reaction vessel and the reaction allowed to sit for 6 hours at ambient temperature in order to go to completion. The supernatant containing the oligomer was then removed from the support and the support was rinsed twice with 2 ml of 1/1 acetonitrile/water; the washings were combined with the supernatant. The combined solution was diluted to 30 ml total volume with water and neutralized with approximately 4 ml of 6 N HCL. The neutralized solution was desalted using a Waters C-18 Sep-Pak cartridge which was pre-equilibrated with 10 ml acetonitrile, 10 ml of 50% acetonitrile/100 mM triethylammonium bicarbonate, and 10 ml of 25 mM triethylammonium bicarbonate, sequentially. After the reaction solution was passed through the column, it was washed with 30 ml of water. The product was then eluted with 5 ml of 1/1 acetonitrile/water.

The oligomer was purified on HPLC using a Beckman Ultrasphere-reverse phase 4.5×250 mm column with an increasing gradient of acetonitrile in 0.5 M triethylammonium acetate (0% to 40% over 40 minutes). The isolated yield was 41 $OD_{260}$ units (35%). The compound was characterized by electron spray mass spectrometry (calc. 4391/found 4391).

Alternatively, the above-identified oligomer can be synthesized on an automated DNA synthesizer. In this case the appropriate dimer synthons (as used above in the manual synthesis) are dissolved in acetonitrile to a concentration of 0.1 M as described above. The amidite solutions are placed in conical vessels on a Millipore Expedite DNA Synthesizer. All other reagents (oxidizer, deblock, capping reagents and activator) are prepared as described above for the manual synthesis, and applied to the appropriate positions on the instrument as instructed in the manual. Programming parameters for one synthesis cycle are as given in Table I in U.S. patent application Ser. No. 08/158,014. The deprotection and purification of the oligomer is carried out as described above for the manually synthesized oligomer.

Example 9

Preparation of a Poly-CU Oliaomer Having Alternating 2'-O-Methyl $MP(R_p)$/2'-O-Methyl DE and 2'-O-Methyl $MP(R_p)$/2'-O-Methyl MP Internucleosidyl Linkages An oligomer having the sequence 5'(C*U)-(C*U)-(C*U)-(C*U)-(C*U)-(C*U)-(C*U)-A-3' SEQ ID NO:2 was prepared using 2-0-methyl $MP(R_p)$/2'-O-methyl DE dimer synthons prepared according to Example 2 hereinabove.

The appropriate dimer synthons were dissolved in acetonitrile to a concentration of 0.1 M. All other reagents used were as described in Example 8.

A 1 μmole scale DNA synthesis column (Millipore) was filled with 1 μmole of methacrylate support bound deoxyadenosine. The dimer synthons were coupled sequentially from the 3'-terminus as described in Example 8 except that the coupling time was extended to two minutes. The overall coupling efficiency based on dimethoxytrityl absorbance was 50%, for an average of 91% per coupling. The dimethoxytrityl group was removed from the oligomer at the end of the synthesis.

The deprotection was carried out as described in Example 8. The crude yield was 103 $OD_{260}$ units. The oligomer was purified on HPLC with a Beckman Ultrasphere-$R_p$ using an increasing gradient of acetonitrile in 0.5 M triethylammonium acetate (10% to 30% over 30 minutes). The isolated yield was 39 $OD_{260}$ units (38%). The compound was characterized by electron spray mass spectrometry (calc. 4713/found 4712).

This oligomer can also be synthesized on an automated DNA synthesizer as follows. The appropriate dimer synthons (as used above in the manual synthesis are dissolved in acetonitrile as described in Example 8. The amidite solutions are placed in conical vessels on the Millipore Expedite DNA synthesizer. All other reagents (oxidizer, deblock, capping reagents and activator) are prepared as described in Example 8, and are applied to the appropriate positions on the instrument as instructed by the manual. The same coupling program as described in Example 8 is used except that the coupling time is extended to 2 minutes.

The deprotection is carried out as described in Example 8. The oligomer can be purified on HPLC using as described above for the manual synthesis.

Using similar procedures as described in detail in Example 8 of U.S. patent application Ser. No. 08/154,013, the oligomer 5'-(C*U)-(C*U)-(C*U)-(C*U)-(C*U)-(C*U)-(C*U)-A-3' SEQ ID NO:2 having 2'-O-methyl $MP(R_p)$/2'-O-methyl MP (racemic) mixed linkages was prepared. The product was also characterized by electron spray mass spectroscopy (calc. 4699.5/found 4701). Automated synthesis may also be employed as explained above.

Example 10

Preparation of 5'-(T*A)-(G*C)-(T*T)-(C*C)-(T*T)-(A*G)-(C*T)-(C*C)-(T*G)-C-3' SEQ ID NO:3 Having Repeated $MP(R_p)$/MP Linkage Structures The grouped dinucleosides indicate coupled dimers and the asterisk indicates where the stereochemistry is fixed (chirally defined or chirally pure) as the fast eluting isomer on silica gel (identified as $R_p$).

An oligomer having this sequence was synthesized using the appropriate protected dinucleotide methylphosphonamidites prepared using methods such as those described in Examples 1A and 1C above. Manual couplings were used to synthesize the oligomer to conserve reagent, although the process can be done on an automated DNA synthesizer from the 3' terminus starting with support-bound cytidine.

Each of the desired protected dinucleotide methylphosphonamidites (22 mg each per required coupling), T*A, G*C, T*T (2x), C*C (2x), A*G, C*T, and T*G, freshly co-evaporated with pyridine and toluene to ensure dryness, was placed into a dried 1 ml glass autosampler vial and dissolved with anhydrous acetonitrile to give a concentration of 0.1 M (200 μl were used per coupling). The vials were purged with argon and tightly sealed with screw caps with teflon septa.

A 1 μmole scale Milligen DNA synthesis column was filled with 1 μmole of support bound cytidine. The column was attached to a ring stand in a vertical orientation. A male-male leur fitting was attached to the bottom along with an 18 gauge needle to control the effluent. The column was washed with 10 ml of ACN using a syringe. The support bound nucleoside was then detritylated by passing 3 ml of 2% dichloroacetic acid in dichloromethane through the column over 1.5 minutes. The orange, dimethoxytrityl cation bearing solution was reserved. The column was washed twice with 10 ml each of ACN (anhydrous).

The first coupling was accomplished by passing 10 ml more ACN (anhydrous) through the column. Then, 200 μl of the TG methylphosphonamidite was drawn into a 1 ml syringe. Next, 200 μL of 0.45 M tetrazole in anhydrous ACN was likewise drawn into the syringe containing the methylphosphonamidite. The reagents were rapidly mixed in the syringe, then slowly passed through the column dropwise over 3 minutes, being sure to lightly draw the plunger up and down to ensure adequate mixing with the support. After 3 minutes, 1 ml of the oxidizing reagent (0.1 M $I_2$ in 74.25% THF, 25% 2,6-lutidine, and 0.25% water) as passed through the column over 1 minute. The column was then washed with 20 ml of ACN. The column was then treated for 1 minute with 600 µl of a solution containing 20% (v/v) acetic anhydride, 30% (v/v) ACN, 50% (v/v) pyridine, and 0.312% (w/v) dimethyaminopyridine. The column was washed with 20 ml of ACN.

The synthetic cycle was then repeated with each dinucleotide methylphosphonamidite until the synthesis was completed. The order of addition of dimers after the initial T*G coupling was C*C, C*T, A*G, T*T, C*C, T*T, G*C, and T*A.

The dimethoxytrityl group was removed from the oligomer at the end of the synthesis.

The oligomer was then cleaved from the support and deprotected. The support bound oligomer was removed from the synthesis cartridge and placed in a glass 1 dram vial with a screw top. The support was treated for 30 minutes at room temperature with 1 ml of a solution of acetonitrile/ethanol/ $NH_4OH$ (9/9/1). Then, 1 ml of ethylenediamine was added to the reaction vessel and the reaction mixture allowed to sit for 6 hours at ambient temperature in order to go to completion. The supernatant containing the oligomer was then removed from the support and the support was rinsed twice with 1 ml of 1/1 acetonitrile/water; the washings were combined with the supernatant. The combined solution was diluted to 50 ml total volume with water and neutralized with approximately 1.7 ml of glacial acetic acid. The neutralized solution was desalted using a Waters C-18 Sep-Pak cartridge which was pre-equilibrated with 5 ml acetonitrile, 5 ml of 50% acetonitrile/water, and 5 ml of water, sequentially. After the reaction solution was passed through the column, it was washed with 50 ml of water. The product was then eluted with 2 ml of 1/1 acetonitrile/water.

The oligomer was purified by HPLC on a reverse phase column (Poros II R/H 4.6×100 mm) using a gradient of acetonitrile in water.

Coupling efficiencies are set forth in the table below.

| Coupling Efficiencies of Dinucleotide Methylphosphonamidites | |
|---|---|
| Dinucleotide | Coupling Efficiency |
| T*G | 99.7% |
| C*C | 90.2% |
| C*T | 91.8% |
| A*G | 85.5% |
| T*T | 97.8% |
| C*C | 83.6% |
| T*T | 100% |
| G*C | 86.2% |
| T*A | 92.4% |

Example 11

Preparation of 5'-(G*T)-(C*T)-(T*C)-(C*A)-(T*G)-(C*A)-(T*G)-(T*T)-(G*T)-C-3' SEQ ID NO:4 Having Repeated MP($R_p$)/MP Linkage Structures The grouped dinucleotides indicate coupled dimers and the asterisk indicates where the stereochemistry is fixed.

This sequence was synthesized using the appropriate protected $R_p$ dinucleotide methylphosphonamidites pre-pared and isolated using procedures such as those described in Examples 1A and 1C above. Manual couplings were used to synthesize the oligomer in order to conserve reagent. However, if desired, the process can be done on an automated DNA synthesizer from the 3' terminus starting with methacrylate support bound 2'-deoxycytidine.

Each of the desired protected dinucleotide methylphosphonamidites (100 mg), G*T, T*T, T*G, C*A, T*G, C*A, T*C, C*T, and C*T was placed into a dried 3 ml glass conical vial and dissolved with anhydrous acetonitrile to a concentration of 0.1 M. Molecular sieves (3 Å) (0.5 ml volume) were added to each vessel, the vessels purged with argon, and tightly sealed with screw caps with teflon septa. The reagents were allowed to stand overnight prior to use.

A 1 µmole scale Milligen DNA synthesis column was filled with 1 µmole of methacrylate support bound 2'-deoxycytidine. The column was attached to a ring stand in a vertical orientation. A male-male luer fitting was attached to the bottom along with an 18 gauge needle to control the effluent. The column was washed with 10 ml of ACN using a syringe. The support bound nucleoside was then detritylated by passing 3 ml of 2.5% dichloroacetic acid in dichloromethane through the column over 3.0 minutes. The orange, dimethoxytrityl cation bearing solution was reserved. The column was washed twice with 10 ml each of ACN (anhydrous).

The first coupling was accomplished by passing 10 ml more ACN (anhydrous) through the column. Then 200 µl of the G*T methylphosphoramidite was drawn into a 1 ml syringe. Next, 200 µl of 0.45 M tetrazole in anhydrous ACN was likewise drawn into the syringe containing the methylphosphonamidite. The reagents were rapidly mixed in the syringe, then slowly passed through the column drop-wise over 1 minute, being sure to lightly draw the plunger up and down to ensure adequate mixing with the support. After 3 minutes, 1 ml of the oxidizing reagent (0.1 M $I_2$ in 74.25% THF, 25% 2,6-lutidine, and 0.25% water) was passed through the column over 1 minute. The column was then washed with 20 ml of ACN. The column was then treated for 1 minute with 600 µl of a solution containing 20% (v/v) acetic anhydride, 30% (v/v) ACN, 50% (v/v) pyridine, and 0.312% (w/v) dimethyaminopyridine. The column was washed with 20 ml of ACN.

The synthetic cycle was then repeated with each dinucleotide methylphosphonamidite until the synthesis was completed. The order of addition of dimers after the initial G*T coupling was T*T, T*G, C*A, T*G, C*A, T*C, C*T and G*T.

The dimethoxytrityl group was removed from the oligomer at the end of the synthesis.

The oligomer was then cleaved from the support and deprotected. The support bound oligomer was removed from the synthesis cartridge and placed in a glass 1 dram vial with a screw top. The support was treated for 30 minutes at room temperature with 1 ml of a solution of acetonitrile/ethanol/ $NH_4OH$ (9/9/1). Then, 1 ml of ethylenediamine was added to the reaction vessel and the reaction allowed 6 hours to go to completion. The supernatant containing the oligomer was then removed from the support and the support was rinsed twice with 1 ml of 1/1 acetonitrile/water; the washings were combined with the supernatant. The combined solution was diluted to 30 ml total volume with water and neutralized with approximately 1.7 ml of glacial acetic acid. The neutralized solution was desalted using a Waters C-18 Sep-Pak cartridge which was pre-equilibrated with 5 ml acetonitrile, 5 ml of 50% acetonitrile/water, and 5 ml of water, sequentially. After the reaction solution was passed through the column it was washed with 5 ml of water. The product was then eluted with 2 ml of 1/1 acetonitrile/water.

The oligomer was purified by HPLC on a reverse phase column (Poros II R/H 4.6×100 mm) using a gradient of acetonitrile in water.

Example 12

Preparation of 5'-(G*A)-(G*G)-(A*G)-(G*A)-(G*G)-(A*G)-(G*A)-(A*G)-G-3' SEQ ID NO:5 Having Repeated MP($R_p$)/MP Linkage Structures The grouped dinucleosides indicate the coupled dimers and the asterisks indicates where the stereochemistry is fixed (chirally defined or chirally pure) as the fast eluting dimer isomer on silica gel (identified as $R_p$).

This oligomer was prepared using automated synthesis coupling G*A, G*G and A*G MP($R_p$)/MP dimer synthons prepared according to the procedures of Examples 1A and 1C.

An amount of G*A, G*G and A*G dimer synthons was dissolved in acetonitrile to give a concentration of 0.1 M and stored over 3 Å molecular sieves (Millipore, Milford, Mass.) overnight.

The dissolved dimers, with molecular sieves, were placed in conical vessels on a Millipore Expedite DNA Synthesizer which as equipped with end-line filters to remove particulates. All other reagents (oxidizer, deblock, capping reagents and activator) were prepared and applied to the appropriate positions on the instrument as instructed in the manual. The coupling program was modified to place the oxidizing step immediately subsequent to the coupling step in order to reduce backbone cleavage prior to oxidation. (See Hogrefe, R. I., et al. "An Improved Method for the Synthesis and Deprotection of Methylphosphonate Oligonucleotides" in *Methods in Molecular Biology*, vol. 20: *Protocols for Oligonucleotides and Analogs* (ed. Agrawal, S.) pages 143–164, Humana Press, Totowa N.Y. (1983). The programming parameters for one synthesis cycle ("Syn4all-1 µmol") are set forth in Table II of U.S. patent application Ser. No. 08/154,013.

A 1 µmole scale DNA synthesis column (Millipore) was filled with 1 µmol of methacrylate support-bound deoxyguanosine and was placed on the DNA synthesizer. The dimers were coupled sequentially from the 3' terminus. The dimethoxytrityl protecting group was removed from the oligomer at the end of the synthesis.

The oligomer was then cleaved from the support and deprotected. The support bound oligomer was removed from the synthesis cartridge and placed in a glass 1 dram vial with a screw top. The support was treated for 30 minutes at room temperature with 1 ml of a solution of acetonitrile/ethanol/$NH_4OH$ (9/9/1). Then, 1 ml of ethylenediamine was added to the reaction vessel and the reaction allowed 6 hours to go to completion. The supernatant containing the oligomer was then removed from the support and the support rinsed twice with 1 ml of 1/1 acetonitrile/water, when combined with the supernatant. The combined solution was diluted to 50 ml total volume with water and neutralized with approximately 1.7 ml of glacial acetic acid. The neutralized solution was desalted using a Waters C-18 Sep-Pak cartridge which was pre-equilibrated with 5 ml acetonitrile, 5 ml of 50% acetonitrile/water, and 5 ml of water, sequentially. After the reaction solution was passed through the column, it was washed with 5 ml of water. The product was then eluted with 1.8 ml of 1/1 acetonitrile/water.

The crude yield was 87 $OD_{260}$ units. The Oligomers was purified on HPLC using a β-cyclobond standard phase 4.5×250 mm column (Azetec, Inc. Whippany, N.J.) with a decreasing gradient (80% to 40%) of acetonitrile in 0.05 M triethylammonium acetate (pH 7). The isolated yield was 22 $OD_{260}$ units (25%). The product was characterized by electron spray mass spectrometry (calc. 5407/found 5401).

Example 13

Preparation of an Oligomer Having Alternating MP ($R_p$)/PS Internucleosidyl Linkages An oligomer having alternating MP($R_p$)/PS internucleosidyl linkages is prepared using dimer synthons. All the parameters of the synthesis, deprotection and purification are as described in Example 8, except that the oxidizing reagent is replaced by a 0.1 M solution of 3 H-1,2-benzodithiole-3-one, 1,1-dioxide or a 0.1 M solution of sulfur in 1/1 carbon disulfide/diisopropylethylamine.

Example 14

Preparation of an Oligomer Having Alternating MPS($R_p$)/DE Internucleosidyl Linkages An oligomer having alternating MPS($R_p$)/DE internucleosidyl linkages is prepared using the dimer synthons of Example 4. All other parameters of synthesis, deprotection and purification are as described in Example 8.

Example 15

Preparation of an Oligomer Having Alternating MPS($R_p$)/PS Internucleosidyl Linkages An oligomer having alternating MPS($R_p$)/PS internucleosidyl linkages is prepared using the dimer synthons of Example 4. All of the parameters of synthesis, deprotection and purification are as described in Example 8, except that the oxidizing reagent is replaced by a 0.1 M solution of 3 H-1,2-benzodithiole-3-one, 1,1-dioxide or a 0.1 M solution of sulfur in 1/1 carbon disulfide/diisopropylethylamine.

Example 16

Preparation of an Oligomer Having Alternating MP ($R_p$)/PS2 Internucleosidyl Linkages An oligomer having alternating MP($R_p$)/PS2 internucleosidyl linkages is prepared using the dimer synthons of Example 5. All of the parameters of synthesis, deprotection and purification are as described in Example 15.

Example 17

Preparation of an Oligomer Having Alternating MPS($R_p$)/PS2 Internucleosidyl Linkages An oligomer having alternating MPS($R_p$)/PS2 internucleosidyl linkages is prepared using the dimer synthons of Example 6. All of the parameters of synthesis, deprotection and purification are as described in Example 16.

Example 17A

Preparation of an Oligomer Having Alternating MP ($R_p$)/2'-O-Methyl DE Internucleosidyl Linkages An oligomer having alternating MP($R_p$)/2'-O-Methyl DE internucleosidyl linkages is prepared using dimer synthons similar to those of Example 7. All other parameters of synthesis, deprotection and purification are as described in Example 9.

Example 18

Preparation of an Oligomer Having Alternating MP (R$_p$)/MPS Internucleosidyl Linkages The preparation of an oligomer having alternating MP(R$_p$)/MPS internucleosidyl linkages is accomplished using dimer synthons prepared according to Examples 1A and 1C and dissolved and stored over molecular sieves. The oxidizing reagent is a 0.1 M solution of 3H-1,2-benzodithiole-3-one, 1,1-dioxide ("Beaucage Reagent", see Iyer, R. P. et al., JACS 112:1254–1255 (1990)) or a 0.1 M solution of sulfur in 1/1 carbon disulfide/diisopropylethylamine, with synthesis proceeding generally as described in Example 12.

Example 19

Preparation of an Oligomer Having 2'-O-Methyl Nucleosidyl Units and Alternating MP(R$_p$)/MPS Internucleosidyl Linkages This oligomer is prepared using the dimer synthons as described in Examples 2A–2D and 2F and following the general synthetic procedures of Example 8 of U.S. patent application Ser. No. 08/154,013, except that the oxidizing reagent described therein is a 0.1M solution of 3H-1,2-benzodithiole-3-one, 1,1-dioxide or a 0.1 M solution on 1/1 carbon disulfide/diisopropylamine.

Example 20

Preparation of an Oligomer Having 2'-O-Methyl Nucleosidyl Units and Alternating MPS(R$_p$)/MP Internucleosidyl Linkages This oligomer is prepared using dimer synthons as described in Example 3 above and by following the parameters of synthesis, deprotection and purification of Example 19.

Example 21

Preparation of an Oligomer Having Alternating MPS(R$_p$)/MP Internucleosidyl Linkages This oligomer is prepared using dimer synthons prepared according to Examples 1A and 1C, substituting Beaucage reagent for the oxidizer in Example 1A, and by following the parameters of synthesis, deprotection and purification as described above in Example 12.

Example 22

Preparation of an Oligomer Having Alternating MPS(R$_p$)/MPS Internucleosidyl Linkages This oligomer is prepared using dimer synthons as referred to in Example 21 and by following the parameters of synthesis, deprotection and purification as described above in Example 12, except that the oxidizing reagent used therein is replaced by a 0.1 M solution of 3H- 1,2-benzodithiole, 1,1-dioxide or a 0.1 M solution of sulfur in 1/1 carbon disulfide/diisopropylethylamine.

Example 23

Preparation of 2'-F Dimer Synthons

Dimer synthons useful in the preparation of the oligomers of the present invention may be prepared using 2'-fluoronucleosides. Methods for preparation of 2'-fluoronucleosides have been reported and are known to those skilled in the art. (See, e.g.: Codington, JOC Vol. 29 (1964) (2'-F U); Mangel, Angew. Chem. 96:557–558 (1978) and Doen, JOC 32:1462–1471 (1967) (2'-F C); Ikehara, Chem. Pharm. Bull. 29:1034–1038 (1981) (2'-F G); Ikehara, J. Carbohydrates, Nucleosides, Nucleotides 7:131–140 (1980) (2'-F A), and also Krug, A, Nucleosides & Nucleotides 8:1473–1483 (1989).)

The preparation of dimer synthons using 2'-fluoronucleosides may be accomplishing using the procedures analogous to those described for the 2'-O-methyl dimer synthons (See, e.g., Examples 2, 3, and 7). The resulting dimer synthons may be used to prepare oligomers using methods analogous to the methods used for the 2'-O-methyl dimer synthons such as in Example 9.

Example 24

Preparation of MP(R$_p$)/MP(R$_p$)/DE and MP(R$_p$)/MP (R$_p$)/MP Trimer Synthons The above-identified trimer synthons are prepared using the MP(R$_p$)/MP dimer synthons of Example 1C. The dimer synthon is coupled to a 5'-hydroxy, 3'-silylated nucleoside according to the methods of Example 1A for the coupling of the 3'-nucleoside to the monomer phosphoramidite.

The selected 5'-hydroxy, 3'-silylated nucleoside (1 equivalent) and isomerically pure R$_p$ dimer methylphosphonamide (1.25 equivalents) are weighed into a round bottom flask and dried by co-evaporation with acetonitrile. The resulting foam is dissolved in acetonitrile and treated with a solution of 0.45 M tetrazole in acetonitrile (4.5 equivalents). After 3 minutes, the reaction mixture is oxidized and the reaction product is worked up as described in Example 1A. The diastereoisomers of the 3'-silylated trimer are resolved on a silica gel column as described in Example 1A for resolution of the dimer isomers. The configuration of the separated diastereoisomers is determined using 2-D nmr (ROSEY). The trimer having the desired chiral configuration (R$_p$/R$_p$) of the two internucleosidyl linkages is converted to a trimer synthon by reaction with chloro-β-cyanoethoxy-N,N-diisopropylaminophosphoramidite using methods as described in Example 1B. The trimer synthon is worked up and purified using methods as described in Example 1B to achieve the MP(R$_p$)/MP(R$_p$)/DE trimer.

Using similar procedures, an MP(R$_p$)/MP(R$_p$)/MP phosphoramidite synthon may be obtained by using chloromethyl-N,N-diisopropylaminophosphine in the final reaction as described in Example 1C for the corresponding dimer synthon. Workup and purification are as described in Example 1C.

Example 25

Preparation of 2'-O-Allyl Dimer and Trimer Synthons and Their Use in Oligomer Synthesis The dimer and trimer synthons described, for example, in Examples 1 and 24 can be prepared using 2'-O-allyl nucleosides. The preparation of 2'-O-allyl nucleosides and their use in the preparation of oligomers has been reported (see e.g. Iribarren, et al. (1990) *Proc. Natl. Acad. Sci.* (*USA*) 87:7747–51; and Lesnik et al. (1983), Biochemistry 32:7832–8), and such substituted nucleosides are commercially available. The nucleosides are used to prepare dimer and trimer synthons using procedures described hereinabove. The synthons are used to prepare oligomers using methods such as those described in Examples 10, 11, 12, 13 and others above.

Example 26

Preparation of an Oligomer Having MP($R_p$)/MP/DE Internucleosidyl Linkages

The above-identified oligomer is prepared using the trimer synthons of Example 24, or by those in Example 20 of U.S. patent application Ser. No. 08/154,014, and by following the methods described in Example 8, substituting the trimer synthons for dimer synthons. All other parameters of synthesis, deprotection and purification are as described in Example 8.

Example 27

Preparation of an Oligomer Having MP($R_p$)/MP ($R_p$)/MP Internucleosidyl Linkages The above-identified oligomer is prepared using the procedures described in Example 14 of U.S. patent application Ser. No. 08/154,013.

Example 28

Preparation of Oligoribonucleosides

Oligoribonucleotides used in the present examples may be synthesized using general procedures such as described below.

The appropriate 5'-O-dimethoxytrityl-2'-O-tert-butyldimethylsilyl-3'-O-N,N-diisopropyl-β-cyanoethylphosphoramidite nucleosides (Millipore, Hilford, Mass.) were used for synthesis. Syntheses were done on a 1 µmole scale with a Milligen 8750 automated DNA synthesizer using standard Milligen phosphoramidite procedures with the exception that the coupling times were extended to 12 minutes to allow adequate time for the more sterically hindered 2'-O-tert-butyldimethylsilyl RNA monomers to react. The syntheses were begun on control-pore glass bound 2'-O-tert-butyldimethylsilyl ribonucleosides purchased from Millipore. All other oligonucleotide synthesis reagents were as described in Millipore's standard protocols.

After synthesis, the oligonucleotides were handled under sterile, RNase-free conditions. Water was sterilized by overnight treatment with 0.5% diethylpyrocarbonate followed by autoclaving. All glassware was baked for at least 4 hours at 300° C.

The oligonucleotides were deprotected and cleaved from the support by first treating the support bound oligomer with 3/1 ammonium hydroxide/ethanol for 15 hours at 55° C. The supernatant, which contained the oligonucleotide, was then decanted and evaporated to dryness. The resultant residue was then treated with 0.6 mL of 1 M tetrabutylammonium fluoride in tetrahydrofuran (which contained 5% or less water) for 24 hours at room temperature. The reaction was quenched by the addition of 0.6 mL of aqueous 2 M triethylammonium acetate, pH 7. Desalting of the reaction mixture was accomplished by passing the solution through a Bio-Rad 10DG column using sterile water. The desalted oligonucleotide was then dried.

Purification of the oligoribonucleotides was carried out by polyacrylamide gel electrophoresis (PAGE) containing 15% 19/1 polyacrylamide/bis-acrylamide and 7 M urea using standard procedures (See Maniatis, T. et al., *Molecular Cloning: A Laboratory Manual*, pages 184–185 (Cold Spring Harbor 1982)). The gels were 20 cm wide by 40 cm long and 6 mm in width. The oligoribonucleotides (60 OD Units) were dissolved in 200 µL of water containing 1.25% bromophenol blue and loaded onto the gel. The gels were run overnight at 300 V. The product bands were visualized by UV backshadowing and excised, and the product eluted with 0.5 M sodium acetate overnight. The product was desalted with a Waters C18 Sep-Pak cartridge using the manufacturer supplied protocol. The product was then $^{32}P$ labelled by kinasing and analyzed by PAGE.

Example 29

Preparation of Racemic Methylphosphonate Oligonucleotides

Various racemic oligomers were synthesized using 5'-(dimethoxytrityl) deoxynucleoside-3'-[(N,N-diisopropylamino)methyl]-phosphonoamidite monomers. Solid-phase synthesis was performed on methacrylate polymer supports with a Biosearch Model 8750 DNA synthesizer according to the manufacturer's recommendations except for the following modifications: the monomers were dissolved in acetonitrile at a concentrations of 100 mM, except dG, which was dissolved in 1/1 acetonitrile/dichloromethane at 100 mM. DEBLOCK reagent=2.5% dichloroacetic acid in dichloromethane. OXIDIZER reagent=25 g/L iodine in 0.25% water, 25% 2,6-lutidine, 72.5% tetrahydrofuran. CAP A=10% acetic anhydride in acetonitrile. CAP B=0.625% N,N-dimethylaminopyridine in pyridine.

The dimethoxytrityl group was removed from the oligonucleotide at the end of the synthesis.

The oligonucleotide was then cleaved from the support and deprotected. The support bound oligonucleotide was removed from the synthesis cartridge and placed in a glass 1 dram vial with a screw top. The support was treated for 30 minutes at room temperature with 1 ml of a solution of acetonitrile/ethanol/NH$_4$OH (9/9/1). Then, 1 ml of ethylenediamine was added to the reaction vessel and the reaction allowed 6 hours to go to completion. The supernatant containing the oligonucleotide was then removed from the support and the support rinsed twice with 2 ml of 1/1 acetonitrile/water, when combined with the supernatant. The combined solution was diluted to 30 ml total volume with water and neutralized with approximately 4 ml of 6 N HCl. The neutralized solution was desalted using a Waters C-18 Sep-Pak cartridge which was pre-equilibrated with 10 ml acetonitrile, 10 ml of 50% acetonitrile/100 mM triethylammonium bicarbonate, and 10 ml of 25 mM triethylammonium bicarbonate, sequentially. After the reaction solution was passed through the column it was washed with 30 ml of water. The product was then eluted with 5 ml of 1/1 acetonitrile/water.

The oligonucleotide was purified by HPLC on a reverse phase column (Whatman RAC II) using a gradient of acetonitrile in 50 mM triethylammonium acetate.

Example 30

Chimeric Oligonucleotide Assembly From MP($R_p$)/ MP and MP($R_p$)/DE Dimer Synthons and Phosphoramidite and Methylphosphonamidite Monomer Synthons MP($R_p$)/MP dimer synthons contained a methylphosphoramidite coupling group at the 3' end. When coupled together to make an oligomer, these synthons give racemic methylphosphonate linkages at every other position.

MP($R_p$)/DE dimer synthons contained a β-cyanoethyl phosphoramidite coupling group at the 3'-end. Both types of dimer synthons were synthesized as described in Example 1. Methylphosphonamidite monomer synthons were synthesized at JBL Scientific (San Luis Obispo, Calif.). Betacyanoethyl phosphoramidite monomer synthons were purchased from Milligen/Biosearch.

All synthons were coupled using a Milligen Expedite™ automated DNA synthesizer. The coupling programs for each synthon were as tabulated below. To generate a phosphorothioate bond during a coupling step, the program "Thioate-5 $\mu$M" was used with either a dimer or monomer synthon containing a β-cyanoethyl phosphoramidite coupling group.

| Function | Mode | Amount /Arg1 | Time (sec) /Arg2 | Description |
|---|---|---|---|---|
| DIESTER - 5 $\mu$M | | | | |
| $Deblocking | | | | |
| 144 /* Advance Frac | */ NA | 1 | 0 | "Event out ON" |
| 0 /* Default | */ WAIT | 0 | 1.5 | "Wait" |
| 141 /* Photometer S | */ NA | 1 | 1 | "START data collection" |
| 16 /* Dblk | */ PULSE | 10 | 0 | "Dblk to column" |
| 16 /* Dblk | */ PULSE | 200 | 49 | "Deblock" |
| 38 /* Wsh A to C1 | */ PULSE | 80 | 0 | "Flush system with Wsh A" |
| 141 /* Photometer S | */ NA | 0 | 1 | "STOP data collection" |
| 39 /* Gas A to C1 | */ PULSE | 10 | 0 | "Gas A to C1 waste" |
| 144 /* Advance Frac | */ NA | 2 | 0 | "Event Out OFF" |
| 12 /* Wsh A | */ PULSE | 200 | 0 | "Wsh A" |
| $Coupling | | | | |
| 1 /* Wsh | */ PULSE | 10 | 0 | "Flush system with Wsh" |
| 2 /* Act | */ PULSE | 10 | 0 | "Flush system with Act" |
| 18 /* A + Act | */ PULSE | 5 | 0 | "Monomer + Act to column" |
| 18 /* A + Act | */ PULSE | 18 | 60 | "Couple monomer" |
| 2 /* Act | */ PULSE | 3 | 10 | "Couple monomer" |
| 1 /* Wsh | */ PULSE | 7 | 56.1 | "Couple monomer" |
| 1 /* Wsh | */ PULSE | 50 | 0 | "Flush system with Wsh" |
| $Capping | | | | |
| 13 /* Caps | */ PULSE | 25 | 0 | "Caps to column" |
| 12 /* Wsh A | */ PULSE | 50 | 0 | "Wsh A" |
| 12 /* Wsh A | */ PULSE | 150 | 0 | "End of cycle wash" |
| $Oxidizing | | | | |
| 13 /* Ox | */ PULSE | 50 | 30 | "Ox" |
| 12 /* Wsh A | */ PULSE | 50 | 0 | "Flush system with Wsh A" |
| $Capping | | | | |
| 13 /* Caps | */ PULSE | 25 | 0 | "Caps to column" |
| 12 /* Wsh A | */ PULSE | 50 | 0 | "Wsh A" |
| 12 /* Wsh A | */ PULSE | 150 | 0 | "End of cycle wash" |
| THIOATE - 5 $\mu$M | | | | |
| $Deblocking | | | | |
| 144 /* Advance Frac | */ NA | 1 | 0 | "Event out ON" |
| 0 /* Default | */ WAIT | 0 | 1.5 | "Wait" |
| 141 /* Photometer S | */ NA | 1 | 1 | "START data collection" |
| 16 /* Dblk | */ PULSE | 10 | 0 | "Dblk to column" |
| 16 /* Dblk | */ PULSE | 200 | 49 | "Deblock" |
| 38 /* Wsh A to C1 | */ PULSE | 80 | 0 | "Flush systemwith Wsh A" |
| 141 /* Photometer S | */ NA | 0 | 1 | "STOP data collection" |
| 39 /* Gas A to C1 | */ PULSE | 10 | 0 | "Gas A to C1 waste" |
| 144 /* Advance Frac | */ NA | 2 | 0 | "Event Out OFF" |
| 12 /* Wsh A | */ PULSE | 200 | 0 | "Wsh A" |
| $Coupling | | | | |
| /* Wsh | */ PULSE | 10 | 0 | "Flush system with Wsh" |
| 2 /* Act | */ PULSE | 10 | 0 | "Flush system with Act" |
| 23 /* 6 + Act | */ PULSE | 6 | 0 | "Monomer + Act to column" |
| 23 /* 6 + Act | */ PULSE | 17 | 60 | "Couple monomer" |
| 2 /* Act | */ PULSE | 4 | 10 | "Couple monomer" |
| 1 /* Wsh | */ PULSE | 7 | 55.9 | "Couple monomer" |
| 1 /* Wsh | */ PULSE | 50 | 0 | "Flush system with Wsh" |
| $Capping | | | | |
| 13 /* Caps | */ PULSE | 25 | 0 | "Caps to column" |
| 12 /* Wsh A | */ PULSE | 50 | 0 | "Wsh A" |
| 12 /* Wsh A | */ PULSE | 150 | 0 | "End of cycle wash" |
| $Oxidizing | | | | |

-continued

| Function | Mode | Amount /Arg1 | Time (sec) /Arg2 | Description |
|---|---|---|---|---|
| 17 /* Aux | */ PULSE | 5 | 0 | "SOx" |
| 17 /* Aux | */ PULSE | 45 | 60 | "SOx" |
| 12 /* Wsh A | */ PULSE | 50 | 0 | "Flush system with Wsh A" |
| $Capping | | | | |
| 13 /* Caps | */ PULSE | 25 | 0 | "Caps to column" |
| 12 /* Wsh A | */ PULSE | 50 | 0 | "Wsh A" |
| 12 /* Wsh A | */ PULSE | 150 | 0 | "End of cycle wash" |
| METHYLPHOSPHONATE - 5 µM | | | | |
| $Deblocking | | | | |
| 144 /* Advance Frac | */ NA | 1 | 0 | "Event out ON" |
| 0 /* Default | */ WAIT | 0 | 1.5 | "Wait" |
| 141 /* Photometer S | */ NA | 1 | 1 | "START data collection" |
| 16 /* Dblk | */ PULSE | 10 | 0 | "Dblk to column" |
| 16 /* Dblk | */ PULSE | 200 | 49 | "Deblock" |
| 38 /* Wsh A to C1 | */ PULSE | 80 | 0 | "Flush system with Wsh A" |
| 141 /* Photometer S | */ NA | 0 | 1 | "STOP data collection" |
| 39 /* Gas A to C1 | */ PULSE | 10 | 0 | "Gas A to C1 waste" |
| 144 /* Advance Frac | */ NA | 2 | 0 | "Event Out OFF" |
| 12 /* Wsh A | */ PULSE | 200 | 0 | "Wsh A" |
| $Coupling | | | | |
| 1 /* Wsh | */ PULSE | 10 | 0 | "Flush system with Wsh" |
| 2 /* Act | */ PULSE | 10 | 0 | "Flush system with Act" |
| 18 /* A + Act | */ PULSE | 5 | 0 | "Monomer + Act to column" |
| 18 /* A + Act | */ PULSE | 18 | 60 | "Couple monomer" |
| 2 /* Act | */ PULSE | 3 | 10 | "Couple monomer" |
| 1 /* Wsh | */ PULSE | 7 | 56.1 | "Couple monomer" |
| 1 /* Wsh | */ PULSE | 50 | 0 | "Flush system with Wsh" |
| $Oxidizing | | | | |
| 15 /* Ox | */ PULSE | 50 | 30 | "Ox" |
| 12 /* Wsh A | */ PULSE | 50 | 0 | "Flush system with Wsh A" |
| $Capping | | | | |
| 13 /* Caps | */ PULSE | 25 | 0 | "Caps to column" |
| 12 /* Wsh A | */ PULSE | 0 | "Wsh A" | |
| 12 /* Wsh A | */ PULSE | 150 | 0 | "End of cycle wash" |
| MP($R_p$)/MP - 5 µM | | | | |
| $Deblocking | | | | |
| 144 /* Advance Frac | */ NA | 1 | 0 | "Event out ON" |
| 0 /* Default | */ WAIT | 0 | 1.5 | "Wait" |
| 141 /* Photometer S | */ NA | 1 | 1 | "START data collection" |
| 16 /* Dblk | */ PULSE | 10 | 0 | "Dblk to column" |
| 16 /* Dblk | */ PULSE | 200 | 49 | "Deblock" |
| 38 /* Wsh A to C1 | */ PULSE | 80 | 0 | "Flush systemwith Wsh A" |
| 141 /* Photometer S | */ NA | 0 | 1 | "STOP data collection" |
| 39 /* Gas A to C1 | */ PULSE | 10 | 0 | "Gas A to C1 waste" |
| 144 /* Advance Frac | */ NA | 2 | 0 | "Event Out OFF" |
| 12 /* Wsh A | */ PULSE | 200 | 0 | "Wsh A" |
| $Coupling | | | | |
| 1 /* Wsh | */ PULSE | 10 | 0 | "Flush system with Wsh" |
| 2 /* Act | */ PULSE | 10 | 0 | "Flush system with Act" |
| 18 /* A + Act | */ PULSE | 5 | 0 | "Monomer + Act to column" |
| 18 /* A + Act | */ PULSE | 18 | 60 | "Couple monomer" |
| 2 /* Act | */ PULSE | 3 | 10 | "Couple monomer" |
| 1 /* Wsh | */ PULSE | 7 | 56.1 | "Couple monomer" |
| 1 /* Wsh | */ PULSE | 50 | 0 | "Flush system with Wsh" |
| $Oxidizing | | | | |
| 15 /* Ox | */ PULSE | 50 | 30 | "Ox" |
| 12 /* Wsh A | */ PULSE | 50 | 0 | "Flush system with Wsh A" |
| $Capping | | | | |
| 13 /* Caps | */ PULSE | 25 | 0 | "Caps to column" |
| 12 /* Wsh A | */ PULSE | 50 | 0 | "Wsh A" |
| 12 /* Wsh A | */ PULSE | 150 | 0 | "End of cycle wash" |

-continued

| Function | Mode | Amount /Arg1 | Time (sec) /Arg2 | Description |
|---|---|---|---|---|
| MP(R$_p$)/DE - 5 μM | | | | |
| $Deblocking | | | | |
| 144 /* Advance Frac | */ NA | 1 | 0 | "Event out ON" |
| 0 /* Default | */ WAIT | 0 | 1.5 | "wait" |
| 141 /* Photometer S | */ NA | 1 | 1 | "START data collection" |
| 16 /* Dblk | */ PULSE | 10 | 0 | "Dblk to column" |
| 16 /* Dblk | */ PULSE | 200 | 49 | "Deblock" |
| 38 /* Wsh A to C1 | */ PULSE | 80 | 0 | "Flush system with Wsh A" |
| 141 /* Photometer S | */ NA | 0 | 1 | "STOP data collection" |
| 39 /* Gas A to C1 | */ PULSE | 10 | 0 | "Gas A to C1 waste" |
| 144 /* Advance Frac | */ NA | 2 | 0 | "Event Out OFF" |
| 12 /* Wsh A | */ PULSE | 200 | 0 | "Wsh A" |
| $Coupling | | | | |
| 1 /* Wsh | */ PULSE | 10 | 0 | "Flush system with Wsh" |
| 2 /* Act | */ PULSE | 10 | 0 | "Flush system with Act" |
| 18 /* A + Act | */ PULSE | 5 | 0 | "Monomer + Act to column" |
| 18 /* A + Act | */ PULSE | 18 | 60 | "Couple monomer" |
| 2 /* Act | */ PULSE | 3 | 10 | "Couple monomer" |
| 1 /* Wsh | */ PULSE | 7 | 56.1 | "Couple monomer" |
| 1 /* Wsh | */ PULSE | 50 | 0 | "Flush system with Wsh" |
| $Oxidizing | | | | |
| 17 /* Aux | */ PULSE | 50 | 30 | "Aux" |
| 12 /* Wsh A | */ PULSE | 50 | 0 | "Flush systetn with Wsh A" |
| $Capping | | | | |
| 13 /* Caps | */ PULSE | 25 | 0 | "Caps to column" |
| 12 /* Wsh A | */ PULSE | 50 | 0 | "Wsh A" |
| 12 /* Wsh A | */ PULSE | 150 | 0 | "End of cycle wash" |

Applying one or more of these coupling routines with the appropriate dimer or monomer synthons, one skilled in the art can recognize that each of the chimeric oligomers described in subsequent examples can be synthesized.

Deprotection and purification of each chimeric oligomer was done essentially as described in Examples 8 through 12.

The identities of certain chimeric oligomers made according to this Example, as well as other compounds, were confirmed by electrospray mass spectrometry as shown in the following table:

| Seq. # | Sequence | Backbone | MW Predicted | MW Found |
|---|---|---|---|---|
| 2624-1 | 3'-CTGTTG TACGT ACCTTCTG-5' SEQ ID NO:4 | Racemic MP | 5725 | 5726 |
| 2571-1 | 3'-CTGTTG TACGT ACCTTCTG-5' SEQ ID NO:4 | 75% MP(R$_p$) | 5725 | 5725 |
| 3130-3 | 3'-CCTGTTG TACGT ACCTTCTG-5' SEQ ID NO:6 | MP(R$_p$)/DE | 6028 | 6029 |
| 2566-1 | 3'-CCTGTTG TACGT ACCTTCTG-5' SEQ ID NO:6 | PS | 6354 | 6357.9 |
| 2567-1 | 3'-CCTGTTG(TACGT)ACCTTCTG-5' SEQ ID NO:6 | [MP][DE][MP] | 6022 | 6018 |
| 2687-1 | 3'-CCTGTT(GTACG)TACCTTCTG-5' SEQ ID NO:6 | [75% R$_p$MP][DE][75% MP] | 6022 | 6022 |
| 3169-1 | 3'-CCTGTTG(TACGT)ACCTTCTG-5' SEQ ID NO:6 | [MP(R$_p$)/DE][DE][MP(R$_p$)/DE] | 6033 | 6034 |
| 3214-1 | 3'-CCTGTTG(TACGT)ACCTTCTG-5' SEQ ID NO:6 | [MP(R$_p$)/DE][PS/DE][MP(R$_p$)/DE] | 6082 | 6081 |
| 3257-1 | 3'-CCTGTTG(TACGTAC)CTTCTG-5' SEQ ID NO:6 | [MP(R$_p$)/DE][PS/DE][MP(R$_p$)/DE] | 6100 | 6100 |
| 3256-1 | 3'-CCTGTTG(TACGT)ACCTTCTG-5' SEQ ID NO:6 | [MP(R$_p$)/DE][PS][MP(R$_p$)/DE] | 6113 | 6114 |
| 3258-1 | 3'-CGTCCTCGATT(CCTTC)GATGGTAC-5' SEQ ID NO:7 | [MP(R$_p$)/DE][PS/DE][MP(R$_p$)/DE] | 7300 | 7299 |
| 3260-1 | 3'-CGTCCTCGATT(CCTTC)GATGGTAC-5' SEQ ID NO:7 | [MP(R$_p$)/DE][PS][MP(R$_p$)/DE] | 7331 | 7331 |
| 3261-1 | 3'-CTCTTCTTCTA(GTGAC)CTATATGG-5' SEQ ID NO:8 | [MP(R$_p$)/DE][PS/DE][MP(R$_p$)/DE] | 7313 | 7310 |

-continued

| Seq. # | Sequence | Backbone | MW Predicted | MW Found |
|---|---|---|---|---|
| 3262-1 | 3'-CTCTTCTTCTA(GTGAC)CTATATGG-5' SEQ ID NO:8 | [MP(R$_p$)/DE][PS][MP(R$_p$)/DE] | 7345 | 7346 |
| 3269-1 | 3'-ACGTCTGATCA(GTAAC)TAACTCAC-5' SEQ ID NO:9 | [MP(R$_p$)/DE[[PS/DE][MP(R$_p$)/DE]) | 7309 | 7308 |
| 3270-1 | 3'-ACGTCTGATCA(GTAAC)TAACTCAC-5' SEQ ID NO:9 | [MP(R$_p$)/DE][PS][MP(R$_p$)/DE] | 7341 | 7340 |

1. (Parenthesis) refers to the portion that activates RNAseH; the linkage on the 5'-side of the indicated nucleoside is charged.

Example 31

Nuclease Stability Studies of Various Backbone Modified (Non-Chimeric) Oligomers In each of the experiments described in this example, various backbone modified oligomers were evaluated having the following sequence: 5'-CTCTCTCTCTCTCTA-3' SEQ ID NO:1 (for 2'-deoxy sugars); or 5'-CUCUCUCUCUCUCUA-3' SEQ ID NO:2 (for 2'-O-methyl sugars). The all-diester (DE) backbone oligomer was purchased from Oligos Etc. The other backbone oligomers were synthesized as described in the preceding examples.

(a) Stability studies in the presence of purified snake venom phosphodiesterase. Snake venom phosphodiesterase I (PDE-I) from *crotalus adamanteus* was purchased from US Biochemicals, Inc. Aliquots of each oligomer (0.075 A$_{260}$ units) were pipetted into polypropylene microcentrifuge tubes and dried in a Speed-Vac™ vacuum centrifuge (Savant, Inc.). Next, the tubes were placed on ice and aliquots of PDE-I were added to each tube (0.1 unit/mL in 95 μL of 10 mM Tris-HCl, pH 8.8, 2 mM MgCl$_2$, 0.4% glycerol). The zero time point samples were diluted immediately with acetonitrile (35 μL), frozen in a dry ice/isopropanol bath, and stored at −20° C. for analysis at a later time. The remaining samples were then placed in a water bath at 37° C. Samples for each specified time point were then removed from the water bath, diluted with acetonitrile and frozen as described for the zero time point samples.

At the conclusion of the nuclease degradation experiment, the samples were individually thawed and analyzed immediately by reversed phase HPLC using a Beckman System Gold apparatus with a Model 126 binary gradient pump module and a Model 168 Diode Array Detector. The samples were injected onto the column using a manual injector with a 2000 μL sample loop. A Vydac C4 Protein column was used for these experiments (Vydac cat. no. 901019, 4.6 mm i.d.×250 mm long). Elution was done with a dual solvent system: Buffer A=1% acetonitrile in 50 mM triethyl ammonium acetate (TEAA, pH 7.0); Buffer B=50% acetonitrile in 50 mM TEAA (pH 7.0). Solvent flow rates were increased from 0.05 to 1.0 mL/min. over the first minute of the run and then held at 1.0 mL/min. for the remainder of the run. Gradient conditions for each backbone were as follows: All-DE backbone-5–25% Buffer B (2.5–9 min.), 25–45% Buffer B (9.0–22.5 min.) 45–100% Buffer B (22.5–28.0 min.); 2'-deoxy MP(R$_p$)/DE backbone-5–35% Buffer B (2.5–12.5 min.), 35–50% Buffer B (12.5–22.5 min.), 50–100% Buffer B (22.5–27.5 min.); 2'-O-methyl MP(R$_p$)/DE backbone-5–50% Buffer B (2.5–17.5 min.), 50–65% Buffer B (17.5–27.5 min), 65–100% Buffer B (27.5–31.0 min.). Average retention times for each backbone oligomer (undegraded) were as follows:

All-DE:
2'-deoxy MP(R$_p$)/DE:
2'-O-methyl MP(R$_p$)/2'-O-methyl DE: 18.6 min.
Degradation was determined by the appearance of earlier eluting peaks and a decrease in area (or complete loss) of the peak corresponding to the full-length oligomer.

(b) Stability studies in HeLa cell lysates. HeLa cell cytoplasmic lysate was purchased from Endotronics, Inc. (Minneapolis, Minn.). This preparation is a hypotonic dounce lysis in 5× the packed cell volume. It was buffered to pH 6.0 by adding 0.4 mL of 2-(N-morpholino) ethanesulfonate (MES, 0.5 M solution, pH 6.0) to 3.6 mL of cell lysate on ice and mixing with mild agitation. Aliquots of oligomer were dried and then diluted with HeLa cell lysate (95 μL) as described in the preceding example. Samples were then incubated at 37° C. and analyzed by reversed-phase HPLC exactly as described in the preceding example.

(c) Stability studies in cell lysate from African Green Monkey Kidney COS-7 cells. COS-7 cell lysate for these experiments was prepared as follows. COS-7 cells were grown to 90% confluency and then harvested in the presence of 0.25% trypsin. The cell pellets were washed twice with phosphate buffered saline and then frozen overnight at −20° C. Next, the pellets were resuspended in approximately an equal volume of lysis buffer (2.5 mM HEPES, pH 7.2, 2.0 mM MgCl$_2$, 0.1% NP-40), drawn up and down ten times through a sterile 1 mL polypropylene pipette, and then centrifuged at 10,000×G for 5 minutes. Approximately 40% of the resulting supernatant was then used to lyse the cell pellet in a dounce homogenizer (Type A pestle) with twenty strokes. This suspension was then centrifuged as above and the supernatant was combined with the rest of the supernatant from the first resuspension. The resulting solution represents predominantly cytosolic lysate without any nuclear debris and is approximately 1–1.5 times the volume of the original packed cell pellet. Aliquots from the resulting cell lysate were buffered with either 25 mM Tris-acetate (final pH 7.4) or 25 mM MES (final pH 6.0) prior to incubation with oligomer. Aliquots of each oligomer (0.075 A$_{260}$ unit) were dried in sterile polypropylene microcentrifuge tubes and then resuspended in 10 μL of COS-7 cell lysate on ice. Water (90 μL) and acetonitrile (35 μL) were added immediately to the zero time samples and they were frozen in a dry ice/ethanol bath and stored at −20° C. for later analysis. The remaining samples were then incubated in a water bath at 37° C. At specified time points, samples were removed from the water bath, diluted with water and acetonitrile, and frozen exactly as described for the zero time point controls. Following the incubations with cell lysate, the samples were individually thawed, diluted with water (535 μL) and analyzed immediately by reversed phase HPLC as described above.

(d) Stability studies in cell lysate from *Escherichia coli*. *E. coli* cell lysate was prepared as follows. Approximately 2×10[11] cells were pelleted by centrifugation, resuspended in 10 mL of Tris-HCl (50 mM, pH 7.5) and incubated at room temperature for five minutes. Next, dithiothreitol and lysozyme were added to final concentrations of 2 mM and 1 mg/mL, respectively, and the resulting suspension was incubated at 37° C. for 30 min. The mixture was then sonicated briefly ten times on ice and centrifuged at 7,000 rpm for 20 min. Based on visual inspection, it was estimated that this procedure had not sufficiently lysed the cells, so the supernatant (vol.=5 mL) was collected and stored at 4° C. and the cell pellet was resuspended in in 1 mL of Tris-HCl (50 mM, pH 7.5). The resuspended cell pellet was exposed to five rounds of freeze/thaw, sonicated briefly to break up the chromosomal DNA, and then centrifuged at 8,000 rpm for 5 min. The resulting supernatant (approx. 700 µL) was then combined with the supernatant from the previous step (approx. 5 mL) and centrifuged at 6,000×G for 5 min. to pellet any residual debris. The final supernatant was estimated to contain approximately 50% lysed cells in approximately 57 times the original cell pellet volume (100 µL). Aliquots of the oligomers (0.050 $A_{260}$ units) were dried in sterile polypropylene microcentrifuge tubes and resuspended in 95 µL of cell lysate on ice. Incubations at 37° C., HPLC analysis, and quantitation of oligomer degradation were done exactly as described above.

(e) Stability studies in cell lysate from *Staphylococcal aureus*. *S. aureus* cell lysate was prepared as described above for *E. coli* except with the following modifications: (i) the lysis was conducted with a cell pellet containing approximately 4×10[10] cells; (ii) lysostaphin was used instead of lysozyme (500 units, Sigma, Inc.); and (iii) a total of 10 freeze/thaw cycles were used instead of five. Incubation with oligomers at 37° C., HPLC analysis and determination of oligomer degradation from the chromatograms were conducted exactly as described for the experiment with *E. coli* in the example above.

Results. Percent degradation was determined by comparing the peak heights and peak areas for each time point in each experiment to the zero time point controls. The half-lives for each oligomer in the presence of PDE-I were then determined by plotting log(% full-length) versus time and finding the value corresponding to log(50%)=1.699. The following table summarizes the results from these experiments:

Metabolic Degradation Rates of Backbone Analogs in Biological Systems.

| Half-life of Analog | Normal Phosphodiester | 2'-O-Methyl RNA | MP($R_p$)/DE Alternating | Alternating 2'-O-Methyl MP($R_p$)/ 2'-O-methyl DE |
|---|---|---|---|---|
| 10% Fetal Calf Serum, pH 8 | 12 min. | 40 min. | 5 Hrs. | >300 Hrs. |
| Green Monkey Kidney Cell Lysate, pH 6.0 | <10 min. | ~5 Hrs. | ~25 Hrs. | Stable* |
| Green Monkey Kidney Cell Lysate, pH 7.4 | <5 min. | ~5 Hrs. | ~20 Hrs. | Stable* |
| *E. coli* Cell Lysate | 1–3 min. | 1.2 Hrs. | ~65 Hrs. | Stable* |
| *S. Aureus* Cell Lysate | 13 min. | ~20 Hrs. | ~75 Hrs. | Stable* |

Metabolic Degradation Rates of Backbone Analogs in Biological Systems.

| Half-life of Analog | Normal Phosphodiester | 2'-O-Methyl RNA | MP($R_p$)/DE Alternating | Alternating 2'-O-Methyl MP($R_p$)/ 2'-O-methyl DE |
|---|---|---|---|---|
| Snake Venom Phosphodiesterasease | 15 min. | 2.5 min. | 167 min. | Stable* |

*No detectable degradation after 24 hour incubation.

Example 32

Hybridization of Chirally Enriched and Non-Chiral Oligomers to RNA Targets

Chirally enriched all-pyrimidine (C*T)$_7$A and all-purine (A*G)$_7$T MP-oligomers were prepared using either $R_p$- or $S_p$-dimeric units. Control oligomers were also prepared using the individual monomeric units. The asterisks indicate the positions of defined chirality.

Each oligomer was annealed to a complementary synthetic RNA target and then monitored by absorbance at 260 nm as a function of temperature. Sigmoidal transitions were observed corresponding to thermal denaturation of the hybridization complexes. The Tm values were determined at the midpoint of each sigmoidal transition. Previously, we have shown that (CT)$_8$ Oligomer forms a double-stranded complex with RNA at neutral pH, whereas (AG)$_8$ Oligomer forms a triple-stranded complex. Thus, we anticipated that the data for each chirally enriched series would be applicable to double-stranded and triple-stranded MP/RNA helices, respectively. The Tm data is summarized below:

Alternating (CT)$_7$
(A)

| Oligomer No. | Sequence | Configuration* |
|---|---|---|
| 2286-1 SEQ ID NO:1 | 5'-c*t-c*t-c*t-c*t-c*t-c*t-c*t-a-3' | ($R_p$) |
| 2288-1 SEQ ID NO:1 | 5'ctctctctctctct-a-3' | (R,S) |
| 2287-1 SEQ ID NO:1 | 5'-c*t-c*t-c*t-c*t-c*t-c*t-c*t-a-3' | ($S_p$) |

(B)

| Oligo | Tm (1:1,RNA) | ΔTm(RNA) |
|---|---|---|
| 2286-1 | 45.5° C. | +10.4° C. |
| 2288-1 | 35.1° C. | — |
| 2287-1 | 25.4° C. | −9.7° C. |

Alternating (AG)$_7$
(A)

| Oligomer No. | Sequence | Configuration* |
|---|---|---|
| 2323-1 SEQ ID NO:10 | 5'-a*g-a*g-a*g-a*g-a*g-a*g-a*g-t-3' | ($R_p$) |
| 2253-1 SEQ ID NO:10 | 5'-agagagagagagag-t-3' | (R,S) |
| 2252-1 SEQ ID NO:10 | 5'-a*g-a*g-a*g-a*g-a*g-a*g-a*g-t-3' | ($S_p$) |

-continued

| | (B) | |
|---|---|---|
| Oligo | Tm (1:1,RNA) | ΔTm(RNA) |
| 2323-1 | 55.2° C. | +7.2° C. |
| 2253-1 | 48.0° C. | — |
| 2252-1 | 40.0° C. | −8.0° C. |

As shown in the tables above, the $R_p$-enriched preparations have higher Tms with RNA targets. On the other hand, $S_p$-enriched preparations have lower Tms with RNA targets.

In separate experiments, we confirmed that the chirally-enriched (C*T)$_7$A and (A*G)$_7$T MP-oligomers form double- and triple-stranded complexes with RNA at neutral pH, respectively.

These experiments demonstrate that chiral enrichment can dramatically effect the binding affinities of MP-oligomers in both a duplex and triplex motif.

Annealing reaction mixtures contained equimolar amounts of methylphosphonate oligomer and RNA target oligomer (2.4 μM total strand concentration), 20 mM potassium phosphate (pH 7.2), 100 mM sodium chloride, 0.1 mM EDTA and 0.03% potassium sarkosylate. The reaction mixtures were heated to 80° C. and then slowly cooled to 4° C. over approximately 4 to 6 hours. The annealed samples were then transferred to 1 cm quartz cuvettes and absorbance at 260 nm as a function of temperature was monitored using a Varian Cary Model 3E Spectrophotometer containing a 6×6 temperature controlled sample holder and which interfaced with an IBM compatible PC computer. The temperature was varied from 5° C. to 80° C. at a ramp rate of 1° C./minute. The Tm for each melt profile is defined at the point corresponding to the first derivative (of the $A_{260}$-temperature function). The following table summarizes data obtained for a number of pairs of racemic versus $R_p$-enriched methylphosphonate oligomers. Based on the observed increases in Tm, $R_p$-enrichment using the MP($R_p$)/MP dimer coupling method described herein leads to significant enhancement in the binding energy between a methylphosphonate oligomer and its RNA target.

Comparison of Tm's for MP($R_p$)/MP Enriched and Racemic Methylphoshonate Oligomers

| Sequence number | Sequence | Tm | ΔTm |
|---|---|---|---|
| 2288-1 SEQ ID NO:1 | 5'-CT-CT-CT-CT-CT-CT-CT-A-3' | 34.4° C. | |
| 2286-1 SEQ ID NO:1 | 5'-(C*T)(C*T)(C*T)(C*T)(C*T)(C*T)(C*T)-A-3' | 44.0° C. | 9.6° C. |
| 2253-1 SEQ ID NO:10 | 5'-AGA-GAG-AGA-GAG-AG-T-3' | 48.9° C. | |
| 2323-1 SEQ ID NO:10 | 5'-(A*G)(A*G)(A*G)(A*G)(A*G)(A*G)(A*G)-T-3' | 56.3° C. | 7.4° C. |
| 2517-1 SEQ ID NO:11 | 5'-GTG-TGT-GTG-TGT-GTG-TA-3'-3' | 41.0° C. | |
| 2516-1 SEQ ID NO:11 | 5'-(G*T)(G*T)(G*T)(G*T)(G*T)(G*T)(G*T)(G*T)-A-3' | 48.8° C. | 7.8° C. |
| 1634-1 SEQ ID NO:3 | 5'-TAG-CTT-CCT-TAG-CTC-CTG-3' | 38.2° C. | |
| 2570-1 SEQ ID NO:3 | 5'-(T*A)(G*C)(T*T)(C*C)(T*T)(A*G)(C*T)(C*C)(T*G)-C-3' | 46.9° C. | 8.7° C. |
| 2688-1 SEQ ID NO:12 | 5'-ATG-GTG-TCT-GTT-TGA-GGT-T-3' | 40.0° C. | |
| 2662-2 SEQ ID NO:12 | 5'-(A*T)(G*G)(T*G)(T*C)(T*G)(T*T)(T*G)(A*G)(G*T)-T-3' | 47.5° C. | 7.5° C. |
| 2624-1 SEQ ID NO:4 | 5'-GTC-TTC-CAT-GCA-TGT-TGT-C-3' | 38.6° C. | |
| 2571-1 SEQ ID NO:4 | 5'-(G*T)(C*T)(T*C)(C*A)(T*G)(C*A)(T*G)(T*T)(G*T)-C-3' | 46.3° C. | 8.2° C. |
| 2625-1 SEQ ID NO:13 | 5'-GCT-TCC-ATC-TTC-CTC-GTC-C-3' | 42.9° C. | |
| 2574-1 SEQ ID NO:13 | 5'-(G*C)(T*T)(C*C)(A*T)(C*T)(T*C)(C*T)(C*G)(T*C)-C-3' | 51.8° C. | 8.9° C. |

Example 33

Tm Comparisons for Methylphosphonate Oligomers Containing Either $R_p$-Enriched or Racemic Backbones Racemic methylphosphonate oligomers and complementary RNA targets were synthesized according to the methods described in Examples 28 and 29. The MP($R_p$)/MP oligomers were synthesized according to the methods described herein by coupling MP($R_p$)/MP dimers. Each coupled MP($R_p$)/MP dimer is indicated by parentheses in the table below, wherein asterisks indicate chirally pure linkages.

Example 34

Binding Stability of Various Backbone Modified Oligomers Having a (CT)$_7$A Model Sequence to Complementary Synthetic RNA Targets Racemic methylphosphonate oligomers and complementary RNA target oligomers were synthesized as described in previous applications. A series of oligomers having the same sequence but with different backbones was prepared as described elsewhere in this application. $R_p$-(CT) dimers were used to make the 75% $R_p$-enriched all-methylphosphonate and the 2'-deoxy MP($R_p$)/2'-deoxy DE oligomers. $_rR$-(CU) dimers were used to make the 2'-O-methyl MP($R_p$)/2'-O-methyl DE oligomer. Oligomers containing phosphorothioate linkages mixed with other linkages were synthesized according to the general procedures described in Example 30 and other examples above. Control oligomers containing either a normal phosphodiester (2'-deoxy all-DE) backbone or a 2'-O-methyl phosphodiester backbone (2'-O-methyl DE), and all-phosphorothioate oligomers, were purchased from Oligos Etc. Where 2'-deoxy or 2'-O-methyl substitutions are indicated below, these structures occur on all of the residues in the alternating or repeated sequence.

Annealing reactions contained equimolar amounts of backbone-modified oligomer and RNA target oligomer (2.4 $\mu$M total strand concentration), 20 mM potassium phosphate (pH 7.2), 100 mM sodium chloride, 0.1 mM EDTA and 0.03% potassium sarkosylate. These reactions were heated to 80° C. and then slowly cooled to 40° C. over a time period of approximately 4–6 hours. Next, the annealed samples were transferred to 1 cm quartz cuvettes and monitored by absorbance at 260 nm as a function of temperature in a Varian Cary Model 3E Spectrophotometer containing a temperature controlled 6×6 sample holder and interfaced to an IBM compatible PC computer. The temperature was varied from 5° C. to 80° C. at a ramp rate of 1° C./min. The Tm is defined as the point corresponding to the maximum of the first derivative of the thermal dissociation profile. The binding constants at 37° C. ($K_A$(37° C.)) were determined by a non-linear least squares fit of the thermal dissociation data assuming a two-state model for the melting process. The following table summarizes the results:

Sequence = 5'-CTCTCTCTCTCTCTA-3'

| Sequence number | Backbone type | Tm (° C.) | $K_A$ (37° C.) |
|---|---|---|---|
| 2288-1 | Racemic all-MP | 34.0 | $8.3 \times 10^5$ |
| 2781-1 | 2'-O-Methyl racemic all-MP | 37.1 | $2.1 \times 10^6$ |
| 2782-1 | Alternating racemic MP/DE | 40.6 | $6.3 \times 10^8$ |
| 2286-1 | 75% $R_p$-enriched all-MP | 44.0 | $2.6 \times 10^7$ |
| 3253-1 | Alternating 2'-deoxy MP($R_p$)/PS | 47.3 | $1.8 \times 10^8$ |
| 2768-1 | 2'-O-Methyl 75% $R_p$-enriched all-MP | 47.4 | $3.9 \times 10^7$ |
| 2793-1 | All-PS | 50.4 | $4.3 \times 10^8$ |
| 2760-1 | Alternating 2'-deoxy MP($R_p$)/DE | 53.8 | $7.9 \times 10^8$ |
| 2784-1 | Alternating 2'-O-Methyl racemic-MP/2'-O-methyl DE | 59.0 | $3.3 \times 10^9$ |
| 2795-1 | 2'-Deoxy all-DE | 60.8 | $7.1 \times 10^{11}$ |
| 2765-1 | Alternating 2'-O-Methyl MP($R_p$)/2'-O-methyl DE | 67.9 | $5.2 \times 10^{12}$ |

-continued

Sequence = 5'-CTCTCTCTCTCTCTA-3'

| Sequence number | Backbone type | Tm (° C.) | $K_A$ (37° C.) |
|---|---|---|---|
| 2792-1 | 2'-O-Methyl all-DE | 75.0 | $5.3 \times 10^{14}$ |

According to this data, a dramatic improvement in binding stability for an RNA target is achieved with the various backbone modifications to the original racemic all-MP oligomer.

Example 35

Binding Affinities of Various Chimeric Backbone Oligomers to Complementary RNA Targets The following oligonucleotides were tested for their ability to hybridize to a complementary synthetic RNA target.

| I.D. # | Sequence | Description |
|---|---|---|
| 2567-1 | SEQ ID NO:6 5'-GTCTTCCA(TGCAT)GTTGTCC-3' | [MP][DE][MP] |
| 2681-1 | SEQ ID NO:6 5'-GTCTTCCA(TGCAT)GTTGTCC-3' | [MP][PS/DE][MP] |
| 2687-1 | SEQ ID NO:6 5'-GTCTTCCAT(GCATG)TTGTCC-3' | [75% MP($R_p$)][DE][75% MP($R_p$)] |
| 3169-1 | SEQ ID NO:6 5'-GTCTTCCA(TGCAT)GTTGTCC-3' | [MP($R_p$)/DE][DE][MP($R_p$)/DE] |
| 3214-1 | SEQ ID NO:6 5'-GTCTTCCA(TGCAT)GTTGTCC-3' | [MP($R_p$)/DE][PS/DE][MP($R_p$)/DE] |
| 3257-1 | SEQ ID NO:6 5'-GTCTTC(CATGCAT)GTTGTCC-3' | [MP($R_p$)/DE][PS/DE][MP($R_p$)/DE] |
| 3256-1 | SEQ ID NO:6 5'-GTCTTCCA(TGCAT)GTTGTCC-3' | [MP($R_p$)/DE][PS][MP($R_p$)/DE] |

The bases shown in parentheses contain the backbone modification indicated in the middle set of brackets for each description, and likewise the terminal portions of the oligomers contain linkage structures as shown in the terminal sets of brackets. The PS/DE notation indicates an alternating array of bases beginning with a phosphorothioate linkage. For example, if there are five bases in a sequence denoted as PS/DE, they include three phosphorothioate (PS) bonds and two phosphodiester (DE) bonds.

Each oligomer was mixed with its complementary synthetic RNA target in a 1:1 molar ratio in a buffer system consisting of 20 mM sodium phosphate buffer (pH 7.2), 100 mM NaCl, 0.03% potassium sarkosylate and 0.1 mM EDTA; total strand concentration=2.4 micromolar. The resulting solutions were heated to 70° C. and slowly cooled to 4° C. over a time period of approximately 4–6 hours. Next, the annealed oligomers were monitored at 260 nm over an increasing temperature gradient of 1° C./minute using a Varian Cary Model 3E UV/Visible Spectrophotometer equipped with a thermostat multicell holder, temperature controller and temperature probe accessories. Data was recorded and processed using a PC computer interface. The Tm values were determined from the first derivative of the sigmoidal melt transition. The binding constants at 37° C. ($K_A$(37° C.)) were determined by applying a non-linear least squares fit to the data and assuming a two-state model for the denaturation process. These values are shown in the table below:

| I.D. # | Tm (° C.) | $K_A$ (37° C.) |
|---|---|---|
| 2567-1 | 45.6 | $2.9 \times 10^7$ |
| 2681-1 | 44.1 | $2.1 \times 10^7$ |
| 2687-1 | 52.8 | $2.6 \times 10^9$ |
| 3169-1 | 62.6 | $6.0 \times 10^{14}$ |
| 3214-1 | 61.0 | $2.3 \times 10^{14}$ |
| 3257-1 | 60.9 | $2.1 \times 10^{14}$ |
| 3256-1 | 60.1 | $5.5 \times 10^{13}$ |

Studies with other chimeric backbone oligomers further demonstrated that compounds containing $R_p$-chiral methylphosphonate bonds have higher net binding stabilities with RNA targets compared to oligomers having the same compositions but with racemic methylphosphonate bonds. Determination of Tm values was done generally as described above. Data for a variety of sequences, some having varying sizes in their RNaseH-activating regions as well as selected 2'-sugar substitutions, were obtained as follows. (Linkage structures separated by slashes indicate an alternating sequence of the listed linkages; thus, in the case of the 5-base PS/DE core of compound 2681-1, a linkage sequence -PS-DE-PS-DE-PS- appears. Uridine residues were substituted for thymidine residues in the bracketed portions of the compounds below having 2'-O-methyl substitutions. 2'-O-methyl sugar substituents were incorporated on each of the methylphosphonate- and phosphodiester-linked nucleoside sugars of the terminal non-RNaseH-activating regions of these compounds (numbers 3341, 3336, 3339, 3337, 3382 and 3386), except for the 3'-terminal residues that were separately bound to the solid support prior to dimer synthon addition (cf. Example 44 below).)

The data showed that a significant enhancement in binding affinity results when racemic methylphosphonate linkages are replaced with $R_p$-chiral methylphosphonates. This observation applies to nucleosides containing 2'-deoxy ribofuranose sugars as well as to bases containing 2'-O-methyl ribofuranose sugars. Oligomers containing regions of alternating $MP(R_p)$/DE linkages have higher binding affinities than oligomers having alternating $MP(R_p)$/MP(racemic) linkages. A further binding enhancement results when 2'-O-methyl ribofuranose sugars are substituted for 2'-deoxy sugars. Based on the data presented above, it is estimated that the Tm increases by about 0.5–0.6° C. per substitution.

Example 36

Demonstration of the Ability of Various Chimeric Oligomers to Activate RNaseH from HeLa Cell Nuclear Extract The following oligomers were tested for their ability to activate endogenous eukaryotic RNaseH derived from HeLa cell nuclear extracts.

| Compound | Backbone Linkage Structure | Tm (° C., RNA) |
|---|---|---|
| | Sequence Type 1 | |
| 5-base core: 5'[GTCTTCCA][TGCAT][GTTGTCC]3' | | SEQ ID NO:6 |
| 7-base core: 5'[GTCTTC][CATGCAT][GTTGTCC]3' | | SEQ ID NO:6 |
| 2681-1 | [MP(racemic)]-(PS/DE)$_5$-[MP(racemic)] | |
| 2567-1 | [MP(racemic)]-(DE)$_5$-[MP(racemic)] | 45.6 |
| 2687-1 | [75% MP(R$_p$)]-(DE)$_5$-[75% MP(R$_p$)] | 52.8 |
| 3256-1 | [MP(R$_p$)/DE]-(PS)$_5$-[MP(R$_p$)/DE] | 60.1 |
| 3214-1 | [MP(R$_p$)/DE]-(PS/DE)$_5$-[MP(R$_p$)/DE] | 61.0 |
| 3169-1 | [MP(R$_p$)/DE]-(DE)$_5$-[MP(R$_p$)/DE] | 62.6 |
| 3257-1 | [MP(R$_p$)/DE]-(PS/DE)$_7$-[MP(R$_p$)/DE] | 60.9 |
| 3341-1 | [2'OMe{MP(R$_p$)/DE}]-(PS)$_7$-[2'OMe{MP(R$_p$)/DE}] | 65.8 |
| 3336-1 | [2'OMe{MP(R$_p$)/DE}]-(PS/DE)$_7$-[2'OMe{MP(R$_p$)/DE}] | 66.8 |
| | Sequence Type 2 | |
| 5-base core: 5'[GCTTGGCTA][TTGCT][TCCATCTTCC]3' | | |
| 7-base core: 5'[GCTTGGCTA][TTGCTTC][CATCTTCC]3' | | |
| 3234-2 | [MP(R$_p$)/DE]-(PS/DE)$_5$-[MP(R$_p$)/DE] | 62.0 |
| 3233-1 | [MP(R$_p$)/DE]-(DE)$_5$-[MP(R$_p$)/DE] | 63.6 |
| 3330-1 | [MP(R$_p$)/DE]-(PS/DE)$_7$-[MP(R$_p$)/DE] | 61.3 |
| 3339-1 | [2'OMe{MP(R$_p$)/DE}]-(PS/DE)$_7$-[2'OMe{MP(R$_p$)/DE}] | 68.8 |
| 3337-1 | [2'OMe{MP(R$_p$)/DE}]-(PS)$_7$-[2'OMe{MP(R$_p$)/DE}] | 70.3 |
| | Sequence Type 3 | |
| 5-base core: 5'[GGTATATC][CAGTG][ATCTUCUTCTC]3' | | |
| 3383-1 | [MP(racemic)12'OMeDE](PS)$_5$[MP(racemic)12'OMeDE] | 59.6 |
| 3382-1 | [2'OMe{MP(rac.)/DE}](PS)$_5$[2'OMe{MP(rac.)/DE}] | 64.4 |
| 3386-1 | [2'OMe{MP(R$_p$)/DE}](PS)$_5$[2'OMe{MP(R$_p$)/DE}] | 64.4 |

| I.D. # | Sequence | Description |
|---|---|---|
| 2498-1 SEQ ID NO:6 | 5'-GTCTTCCATGCATGTTGTCC-3' | All-DE |
| 2566-1 SEQ ID NO:6 | 5'-GTCTTCCATGCATGTTGTCC-3' | All-PS |
| 3130-1 SEQ ID NO:6 | 5'-GTCTTCCATGCATGTTGTCC-3' | MP($R_p$)/DE Alternating (Non-Chimeric) |
| 3169-1 SEQ ID NO:6 | 5'-GTCTTCCA(TGCAT)GTTGTCC-3' | [MP($R_p$)/DE][DE][MP($R_p$)/DE] |
| 3214-1 SEQ ID NO:6 | 5'-GTCTTCCA(TGCAT)GTTGTCC-3' | [MP($R_p$)/DE][PS/DE][MP($R_p$)/DE] |
| 3256-1 SEQ ID NO:6 | 5'-GTCTTCCA(TGCAT)GTTGTCC-3' | [MP($R_p$)/DE][PS][MP($R_p$)/DE] |

Each of these oligomers (10 μM) was annealed to its complementary synthetic RNA target (1 μM) in a buffer system containing 50 mM Tris-HCl (pH 8.0), 20 mM KCl, 9 mM $MgCl_2$, 1 mM β-mercaptoethanol, 250 μg/mL bovine serum albumin, and 25–100 units/mL of RNasin (Promega, Corp., Madison, Wis.). Radiolabeled RNA having $^{32}P$ at the 5'-terminus was prepared using [y-$^{32}P$]-ATP (New England Nuclear/DuPont, Boston, Mass.) and T4-polynucleotide kinase (Stratagene, Inc., San Diego, Calif.) according to standard procedures. Approximately 200,000 dpms of $^{32}P$-labeled RNA was included in each reaction as a radiotracer. These samples were annealed by heating to 65° C. and slowly cooling to 4° C. over a period of approximately 4–6 hours.

Stock solutions containing HeLa cell nuclear extract were prepared as follows. HeLa cell nuclear extract (Promega Corp., Madison, Wis., Catalog # E3521, 5 mg/mL protein) was diluted 250-fold in a buffer consisting of 20 mM HEPES (pH 8.0), 20% glycerol, 0.1 M KCl, 0.2 mM paramethylphenylsulfonyl fluoride (PMSF) and 0.5 mM dithiothreitol.

RNaseH cleavage reactions were initiated by adding diluted HeLa cell nuclear extract (5 μL) to each of the annealed oligomer samples (10 μL) and then the samples were incubated at 37° C. for either fifteen minutes or two hours. At the end of the specified incubation time, each cleavage reaction was terminated by addition of 1.5 μL of EDTA (125 mM, pH 8) and then quickly frozen on dry ice and stored at −20° C. When all of the cleavage reactions had been terminated they were removed from the freezer for analysis by polyacrylamide gel electrophoresis. Aliquots (5 μL) were withdrawn from each reaction and diluted with gel loading buffer (5 μL, 90% formamide/1×TBE buffer/0.1% bromphenol blue/0.1% xylene cyanole blue). The resulting samples were loaded onto a 15% polyacrylamide/7 M urea gel (20 cm×30 cm×0.5 mm thick) prepared in 1×TBE buffer (pH 8.2). The gel was electrophoresed at 1200 volts for 1.5 hours. Bands on the gel corresponding to full length and cleaved RNA products were detected by phosphorimager analysis using a Bio-Rad Model GS-250 Molecular Imager (Bio-Rad Laboratories, Hercules, Calif.). The amount of cleavage that occurred in each reaction was determined by comparing the phosphorimager counts for the full length band to the total counts per lane. The results are summarized below:

| Oligomer I.D. # | RNaseH Cleavage after 2 Hrs. at 37° C. |
|---|---|
| 2498-1 | 24.4% |
| 2566-1 | 10.5% |
| 3130-1 | None detected |
| 3169-1 | 52.0% |
| 3214-1 | 38.0% |
| 3256-1 | 18.7% |

The length of each cleavage fragment was estimated from the electrophoretic mobility of its associated radioactive band. From this analysis, it was determined that cleavage occurs selectively in the middle of heteroduplexes derived from the chimeric oligomers. More numerous cleavage products were observed with the all-phosphodiester (DE) and all-phosphorothioate (PS) oligomers, as expected. This data shows that the replacement of PS for DE linkages results in a reduction in the rate of RNaseH-mediated cleavage. There was no cleavage observed in the sample containing an alternating MP($R_p$)/DE backbone.

Example 37

Stability of Various Chimeric Oligomers to Nuclease Digestion in the Presence of S1-Endonuclease The following oligomers were tested for nuclease stability in the presence of S1-endonuclease.

| I.D. # | Sequence | Description |
|---|---|---|
| 2567-1 | 5'-GTCTTCCA(TGCAT)GTTGTCC-3' | [MP][DE][MP] |
| 2681-1 | 5'-GTCTTCCA(TGCAT)GTTGTCC-3' | [MP][PS/DE][MP] |
| 3169-1 SEQ ID NO:6 | 5'-GTCTTCCA(TGCAT)GTTGTCC-3' | [MP($R_p$)/DE][DE][MP($R_p$)/DE] |

| I.D. # |  | Sequence | Description |
|---|---|---|---|
| 3214-1 | SEQ ID NO:6 | 5'-GTCTTCCA(TGCAT)GTTGTCC-3' | [MP(R$_p$)/DE][PS/DE][MP(R$_p$)/DE] |
| 3256-1 | SEQ ID NO:6 | 5'-GTCTTCCA(TGCAT)GTTGTCC-3' | [MP(R$_p$)/DE][PS][MP(R$_p$)/DE] |

Figure 1B:
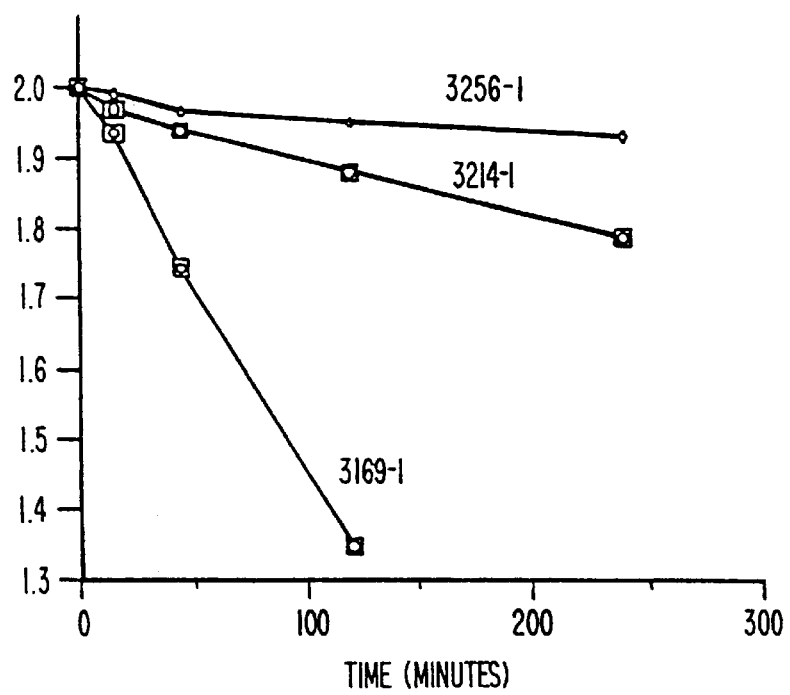

S1-endonuclease was purchased from Promega Corp. (Catalog # E576B, Madison, Wis.). Aliquots of each chimeric oligomer (0.05–0.075 OD$_{260}$ units) were individually added to polypropylene microcentrifuge tubes containing S1-endonuclease (0.5 units/mL) in 30 mM sodium acetate (pH 5.0), 50 mM NaCl, 1.0 mM zinc acetate and 5% glycerol; total reaction volume=10 μL. These tubes were incubated at 37° C. for specified time periods, quickly frozen in dry ice and then stored in a freezer at −20° C. The samples were then analyzed by reversed-phase HPLC using a Beckman System Gold chromatography system equipped with a Model 126 Solvent Module and a Model 168 Diode Array Detector. Column=Vydac Protein C4 (catalog #214TP54, 4.9 mm i.d.×250 mm long). Buffer A=50 mM triethylammonium acetate (pH 7)/1% acetonitrile; Buffer B=50 mM triethylammonium acetate (pH 7)/50% acetonitrile. The elution profile was 5–35% Buffer B (2.5–12.5 min.); 35–50% Buffer B (12.5–22.5 min.); 50–100% Buffer B (22.5–27.5 min.); flow rate=1.5 mL/min. The samples were diluted with water (50 μL) and injected onto the column using a 100 μL sample loop. Peaks corresponding to full length oligomer and its degradation products were detected by monitoring at 260 nm. The amount of degradation occurring in each reaction was determined by measuring the reduction in peak area for the full-length oligomer (identified by comparison to an external control and/or by coinjecting undigested oligomer as an internal control). The data is shown in tabular format below, and in graphic format in FIG. 1.

| Oligomer I.D. # | Half-Life for Degradation* |
|---|---|
| 2567-1 | 1.7 Hrs. |
| 2681-1 | 12.2 Hrs. |
| 3169-1 | 0.9 Hrs. |
| 3214-1 | 5.0 Hrs. |
| 3256-1 | 12.5 Hrs. |

*Determined as the point where 50% full length oligomer has been digested based on a least-squares fit of the data.

This data shows that the replacement of phosphorothioate (PS) bonds for phosphodiester (DE) bonds imparts a resistance to nuclease degradation catalyzed by S1-endonuclease.

Example 38

Figure 2A:
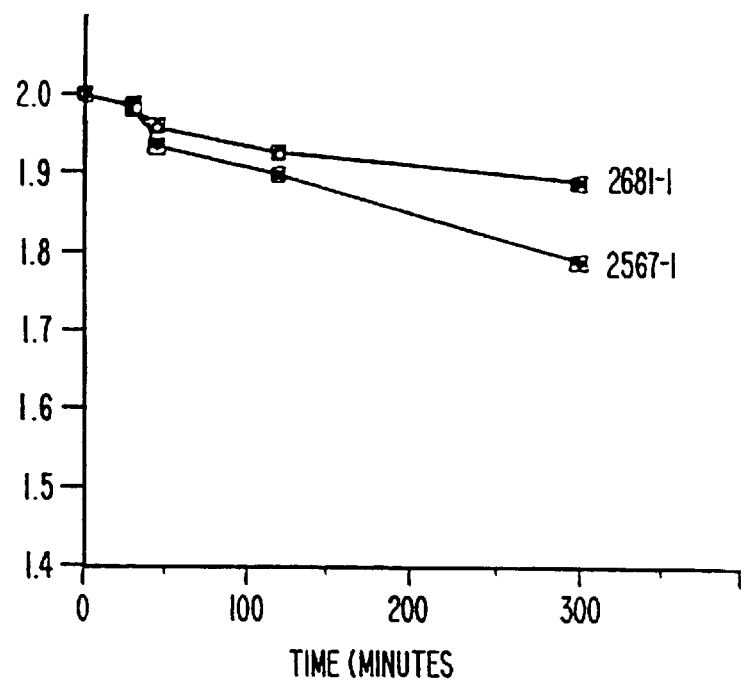
Figure 2B:
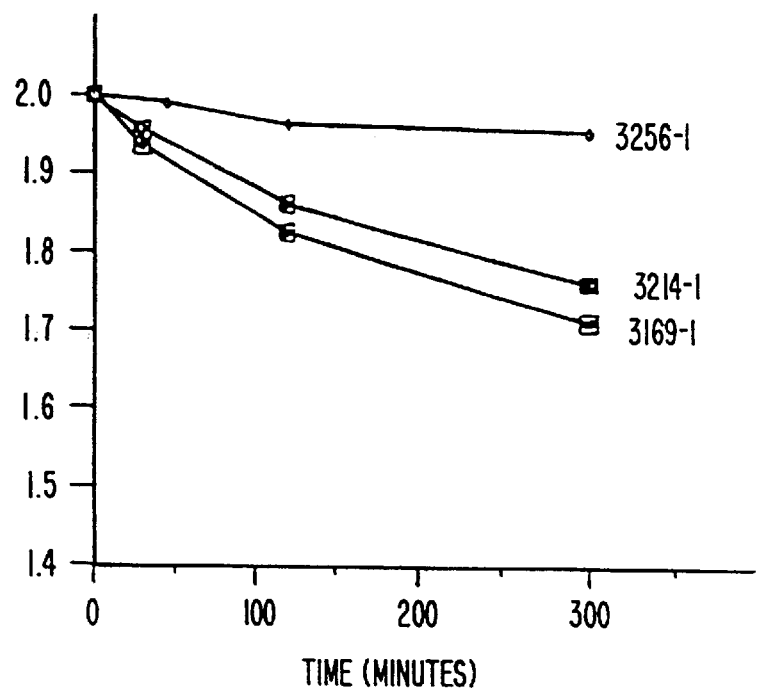

Stability of Various Chimeric Oligomers to Nuclease Digestion in the Presence of 10% Fetal Calf Serum Multiple samples of each chimeric oligomer were prepared in 1.5 mL polypropylene microcentrifuge tubes on ice. Each sample contained oligomer (0.1 OD$_{260}$ unit), 10% fetal calf serum (FCS, Gemini Bioproducts, Calabasas, Calif.), 20 mM HEPES (pH 8.0), 0.2% paramethylsulfonyl fluoride (PMSF), 175 mM KCl, 0.1 mM dithiothreitol, 0.1 mM EDTA, 2 mM MgCl$_2$ and 4% glycerol—total volume=100 μL. The samples were incubated at 37° C. for specified time periods and then diluted with 0.4% NP-40/acetonitrile (35 μL), quickly frozen on dry ice and stored at −20° C. Samples were then individually thawed, diluted with water (635 μL) and analyzed immediately by reversed-phase HPLC according to the method given in the preceding example (except that a 2 mL sample loop was used to load the samples onto the column). Results are shown in tabular format below, and in graphical format in FIG. 2.

| Oligomer I.D. # | Half-Life for Degradation* |
|---|---|
| 2567-1 | 5.8 Hrs. |
| 2681-1 | 8.1 Hrs. |
| 3169-1 | 3.4 Hrs. |
| 3214-1 | 4.3 Hrs. |
| 3256-1 | 16.2 Hrs. |

*Determined as the point where 50% full length oligomer has been digested based on a least-squares fit of the first three time points in each data set.

This example indicates a similar enhancement in stability to nuclease degradation when PS linkages are used in place of DE linkages.

Example 39

Activity of [MP][DE][MP] Oligomer 2567-1 and [MP(R$_p$)/DE]-[DE]-[MP(R$_p$)/DE] oligomer 3169-1 on Cell-Free Translation of Taraet mRNA A target mRNA having complementarity to these oligomers at the initiation codon region was prepared by standard cloning techniques with reverse-transcription catalyzed by T7 polymerase (Promega MEGAscript kit for uncapped RNA), according to the manufacturer's protocol. Control CAT mRNA was obtained from GIBCO as a control for specificity.

Target mRNA and control CAT mRNA were translated in a cell-free translation assay in rabbit reticulocyte lysates (Promega), in the presence of $^{35}$[S]-Cys (NEN/DuPont) following the manufacturer's directions. Oligos 2567-1 and 3169-1 were added to individual translation reactions at 0, 0.2, or 1.0 M, final concentrations. RNAse-H (Promega Corp.) was added to all the translation reactions at 0.04 units/ul. Each condition was run in triplicate. Translation reactions were incubated at 37° C. for 1 hour. At the end of the translation reactions, proteins were denatured with Laemmli Sample Buffer (Novex) and the amounts of target proteins synthesized in each case were evaluated after immunoprecipitation with an hyperimmune antibody serum followed by gel fractionation of the protein products (10–20% gradient SDS-PAGE gels, Novex) and phospho-image analysis. The amount of control CAT protein synthesized in each case was evaluated after gel fractionation of one aliquot of the denatured translation reaction (10–20% gradient SDS-PAGE gels, Novex) and phospho-image analysis.

Figure 3:
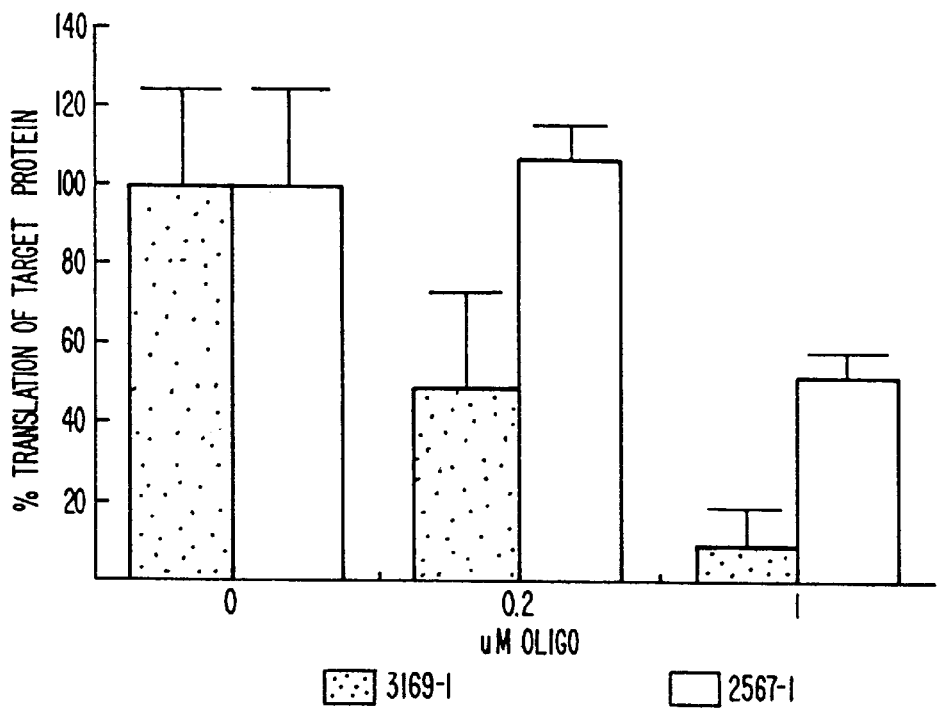
FIGS. 3 and 4 are bar graphs showing dose-response activity of a chirally-selected compound of the present invention, versus a non-chirally-selected compound, in inhibiting target (FIG. 3) and non-target (FIG. 4) protein synthesis.
Figure 4:
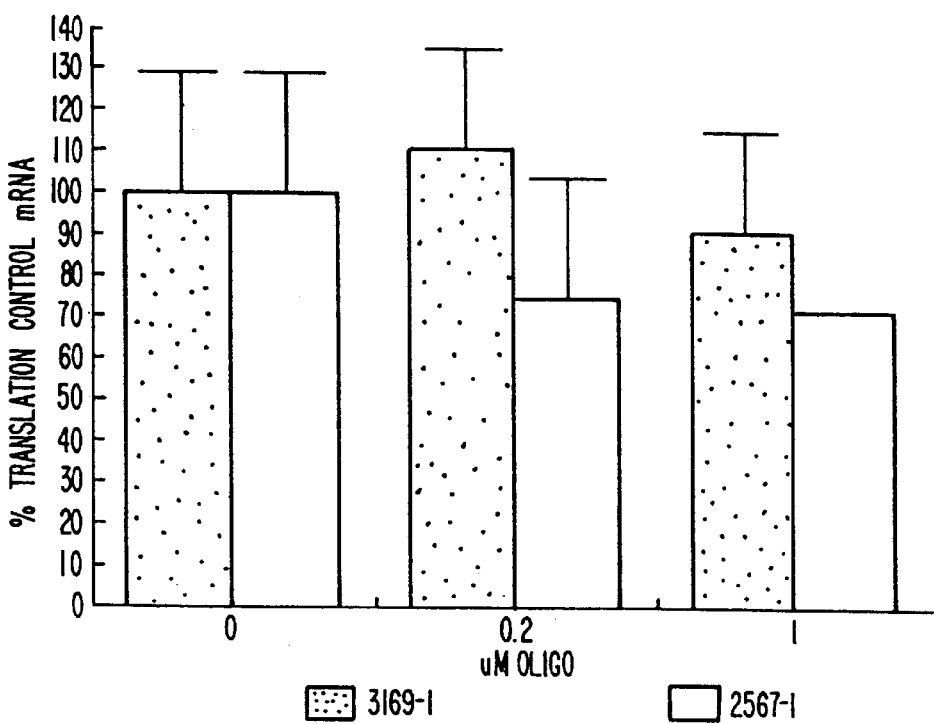

As shown in FIGS. 3 and 4, oligomer 3169-1 produced approximately 50% and 90% inhibition of target mRNA translation when present at 0.2 or 1 μM, respectively. Oligomer 2567-1 produced approximately 0% and 50% inhibition of target mRNA translation when present at 0.2 or 1 μM, respectively. Both oligos produced little inhibition of control CAT mRNA translation, indicating good specificity.

This result indicates that replacement of racemic MP ends by chirally-selected MP($R_p$)/DE linkage segments significantly increases the ability of an oligomer to block cell-free translation of the target mRNA.

Example 40

Cleavage of Target mRNA, in the Presence of RNAseH, of [MP][DE][MP] Oligomer 2567-1 and [MP($R_p$)/DE]-[DE]-[MP($R_p$)/DE] Oligomer 3169-1

A target mRNA having complementarity to these oligomers at the initiation codon region was prepared by standard cloning techniques with transcription using a T7 polymerase cell-free assay (Promega MEGAscript kit for uncapped RNA), according to the manufacturer's protocol. The resulting mRNA transcript is approximately 340 nt in length.

The ability to cleave this target mRNA, in the presence of RNAseH and either of oligomers 2567-1 {[MP]-[DE]-[MP]} and 3169-1 {[MP($R_p$)/DE]-[DE]-[MP($R_p$)/DE]} was determined as follows.

Cell-free transcribed mRNA (100 nM) was incubated at 37° C., in a cell-free translation buffer (containing 3.5 mM $MgCl_2$, 25 mM KCl, 70 mM NaCl and 20 mM potassium acetate), in the presence of 0.04 units/μl of RNAseH (Promega) and either of oligomers 2567-1 or 3169-1 at 0, 0.01, 0.1, 1, or 10 μM. After 30 minutes, the RNA was extracted, denatured and run in a denaturing gel. After the run, the RNA was stained with ethidium bromide and its integrity was determined by visual observation of the RNA bands present in the gel.

As shown in the table below, a good dose-response effect was obtained for both oligomers at the concentrations tested. Oligomer 3169-1 was more active than oligomers 2567-1 (3169-1, at 1 μM, cut ~98% of the target mRNA present in the reaction, while oligomer 2567-1, at the same concentration, cut ~50% of the target mRNA present in the reaction). Both oligomers showed good specificity, cleaving the target mRNA in one position.

| Cleavage of target mRNA, in the presence of RNAseH, of [MP][DE][MP] oligomer 2567-1 and [MP($R_p$)/DE]-[DE]-[MP($R_p$)/DE] oligomer 3169-1 | | | | | | | | |
|---|---|---|---|---|---|---|---|---|
| Oligomer | 2567-1 | | | | 3169-1 | | | |
| Backbone | [MP]-[DE]-[MP] | | | | [MP($R_p$)/DE][DE][MP($R_p$)/DE] | | | |
| Oligomer concentration (μM) | 0.01 | 0.1 | 1 | 10 | 0.01 | 0.1 | 1 | 10 |
| % of target mRNA cleavage* | 2 | 15 | 50 | 80 | 5 | 40 | 98 | 100 |

(*)Estimated values obtained by visual inspection of the gel

Example 41

Inhibition of Protein Synthesis in a Cell Culture With Chimeric Antisense Oligomers Targeted to a Non-Eukaryotic Reporter Gene, Chloramphenicol Transferase The following example shows the ability of chimeric antisense oligomers to selectively inhibit protein synthesis in a eukaryotic cell culture system. COS-7 cells were transiently transfected with plasmids encoding either a target reporter gene or a control non-target reporter gene. These cells were then treated with various chimeric antisense or control oligomers and then assayed for the expression of the reporter genes.

Plasmids

The following plasmids were used in this example.

pG1035: Splicer CAT, inserted into a pRc/CMV vector pG1036: Wild-type CAT, inserted into a pRc/CMV vector pG1040: UCAT, inserted into a pRc/CMV vector pGL2: Luciferase expressing plasmid (Promega)

pSVβ: β-galactosidase expressing plasmid (Clonetech)

A description of plasmids pG1035, pG1036 and pG1040 follows.

1. pG1035 (SplicerCAT) and pG1036 (wild-type CAT) and the sequences of the synthetic splice sites:

A. Sequence of the wild type CAT gene used to create plasmid pG1036:

```
                                    +409 +410                      SEQ ID NO:4
                                      |   |
             GCC UAU UUC CCU AUU UCC CUA AAG GGU UUA UUG AGA AUA
```

B. Full sequence of the intron inserted within the CAT coding sequence to create SplicerCAT and plasmid pG1035:

```
                          +409 1                    SEQ ID NO:15
                           | ˆ|
  ... UAU UUC CCU AUU UCC CUA AAG gug agu gac uaa cua agu 39
                              |
  cga cug cag acu agu cau ug(a) uug agu gua aca aga ccg gau 87 +410
                                  | ˆ|
  auc uuc gaa ccu cuc ucu cuc cag GGU UUA UUG AGA ...
```

The region of the CAT gene into which the intron was inserted is shown in sequence A above. Wild type CAT DNA (Pharmacia) was inserted into pRc/CMV (Invitrogen) to create plasmid pG1036. The sequence is shown as the mRNA. Bases 409 and 410 are labeled for comparison to pG1035. A synthetic intron, shown as sequence B above, was inserted into the CAT DNA to create plasmid pG1035. Mature mRNA sequences are shown uppercase, intronic sequences are lower case. The canonical guanosine of the splice donor is labeled +409, which corresponds to base 409 of the CAT open reading frame. The first base of the intron is labeled 1. The canonical branchpoint adenosine is base 39 and the canonical intronic splice acceptor guanosine is base 87 of the intron. Base 410 marks the resumption of the CAT open reading frame. The sequences against which the oligomers are targeted are underlined. The consensus splice site bases are given in bold face italics (Smith et al. 1989; Green 1986).

The clone pG1035 was created using synthetic DNA PCR primers to create a Hind III-Spe I 5' fragment containing the first ⅔ of the open reading frame and half of the synthetic intron and an Spe I-Not I fragment containing the second half of the intron and the last ⅓ of the open reading frame. These were combined with Hind III-Not I cut pRc/CMV in a 3-way ligation to yield the final plasmid. The artificial CAT gene containing the intron is named SplicerCAT. References applicable to the foregoing include Smith C W J, Patton J G, and Nadal-Ginard B, (1989), "Alternative splicing in the control of gene expression," Annual Reviews in Genetics 23: 527–77; Green, M R (1986), "Pre-mRNA splicing," Annual Reviews in Genetics 20: 671–708.

2. pG1040 (UCAT) 5' untranslated regions and amino terminus:

The sequences of wild type and pG1040 UCAT around the AUG start codon are shown. The target sites for the oligomers are named and underlined, and the numbers of the chimeric oligomers against each target site are shown beneath.

UCAT was made from wild-type CAT DNA (Pharmacia) using synthetic DNA PCR primers. The resulting fragment was cloned as a Hind III (5' end), Not I (3' end) fragment into the vector pRc/CMV (Invitrogen). The first adenosine of the open reading frame is designated +1. The amino acid changes between wild-type and pG1040 are conservative.

| 5'AUG oligomers (position −21 to +3): |
|---|
| 3258-1 SEQ ID NO:7, |
| 24mer, (MP(R$_p$)/DE)(PS/DE)(MP(R$_p$)/DE): |
| 5' cat ggt ag(c ttc c)tt agc tcc tgc 3' |
| 3260-1 SEQ ID NO:7, |
| 24mer, (MP(R$_p$)/DE)(PS)(MP(R$_p$)/DE): |
| 5' cat ggt ag(c ttc c)tt agc tcc tgc 3' |
| 3' AUG oligomers (position +4 tc +27) |
| 3261-1 SEQ ID NO:8, |
| 24mer, (MP(R$_p$)/DE)(PS/DE)(MP(R$_p$)/DE): |
| 5' ggt ata tc(c agt g)at ctt ctt ctc 3' |
| 3262-1 SEQ ID NO:8, |
| 24mer, (MP(R$_p$)/DE)(PS)(MP(R$_p$)/DE): |
| 5'ggt ata tc(c agt g)at ctt ctt ctc 3' |
| 3636-1 SEQ ID NO:8, |
| 24mer, (MP(R$_p$)/DE)(PS)(MP(R$_p$)/DE): |
| 5'ggt a(ta tcc) agt gat ctt ctt ctc 3' |
| 3638-1 SEQ ID NO:8, |
| 24mer, (MP(R$_p$)/DE)(PS)(MP(R$_p$)/DE): |
| 5'ggt ata tcc agt (gat ct)t ctt ctc 3' |
| 3637-1 SEQ ID NO:8, |
| 24mer, (MP(R$_p$)/DE)(PS)(MP(R$_p$)/DE): |
| 5'ggt ata tcc agt gat c(tt ctt) ctc 3' |

```
                          Wild-type CAT SEQ ID NO:16:
 5'                                +1                                                        3'
                                   Met Glu Lys Lys Ile Ser Gly Tyr Thr Thr
 uuu uca gaa gcu aag gaa gcu aaa aug gag aaa aaa auc acu gga uau acc acc
                                 pG1040, UCAT SEQ ID NO:17:
 5'                                +1                                                        3'
                                   Met Glu Lys Lys Ile Ser Gly Tyr Thr Thr
 agu gca gga gcu aag gaa gcu acc aug gag aag aag auc acu gga uau acc acc
                 5'AUG site                           3'AUG site
                 3258-1
                 3260-1
```

-continued 3640-1, 24mer, (MP(R$_p$)/DE)(PS)(MP(R$_p$)/DE)
5'ggt ata tc(a agt g)at ctt ctt ctc 3'
3639-1, 24mer, (MP(R$_p$)/DE)(PS)(MP(R$_p$)/DE):
5'ggt ata tc(g agt g)at ctt ctt ctc 3'
Splice donor oligomers:

3264-1 SEQ ID NO:18,
24mer, (MP(R$_p$)/DE)(PS)(MP(R$_p$)/DE):
5' cac tca cct t(ta ggg) aaa tag gcc 3'
3263-1 SEQ ID NO:18,
24mer, (MP(R$_p$)/DE)(PS/DE)(MP(R$_p$)/DE):
5' cac tca cct t(ta ggg) aaa tag gcc 3'
XV-5 SEQ ID NO:18,
24mer, all phosphorothioate:
5' cac tca cct tta ggg aaa tag gcc 3'
Splice branch point oligomers:

3269-1 SEQ ID NO:9,
24mer, (MP(R$_p$)/DE)(PS/DE)(MP(R$_p$)/DE):
5' cac tca at(c aat g)ac tag tct gca 3'
3270-1 SEQ ID NO:9,
(MP(R$_p$)/DE)(PS)(MP(R$_p$)/DE):
5' cac tca at(c aat g)ac tag tct gca 3'
XV-6 SEQ ID NO:9,
24mer, all phosphorothioate:
5' cac tca atc aat gac tag tct gca 3'
Splice acceptor site oligomers:

3265-1 SEQ ID NO:19,
24mer, (MP(R$_p$)/DE)(PS/DE)(MP(R$_p$)/DE):
5' ccc tga ga(g aga g)ag aga ggt tcg 3'
3266-1 SEQ ID NO:19,
24mer, (MP(R$_p$)/DE)(PS)(MP(R$_p$)/DE):
5' ccc tga ga(g aga g)ag aga ggt tcg 3'
3387-1 SEQ ID NO:19,
24mer, [2'OMe(MP(R$_p$)/DE)](PS)[2'OMe(MP(R$_p$)/DE)]:
5' ccc tga ga(g aga gag) aga ggt tcg 3'
XV-7 SEQ ID NO:19,
24mer, all phosphorothioate:
5' ccc tga gag aga gag aga ggt tcg 3'

Cell Preparation and Treatment

COS 7 cells were plated at $1.5 \times 10^5$ cells/well in a 12 well plate format on the day before trans-fections began. All cultures were maintained at 37° C. On the next day, the transfection mixes were prepared. For each well of a 12 well plate, 1.0 μM oligomer was combined with 1 μg pGL2 or pSVβ+1 μg of the target CAT plasmid in 0.5 ml of Optimem (Gibco/BRL) and 18.75 μg Transfectam (for chimeric oligomers, Promega) or Lipofectamine (for all PS oligomers, Promega) also in 0.5 ml of Optimem. These quantities gave a 6.9 or 4.5 or 2.0 to 1 cationic lipid to oligomer plus DNA ratio, respectively, in one milliliter total. pGL2 and pSVβ served as transfection and oligomer specificity controls.

The culture medium was aspirated off and the cells were rinsed twice in one ml Optimem (Gibco/BRL) per well, and then one ml of tranfection mix was added to each well. The cells were cultured in the transfection mix for 16 hours. The mix was removed and replaced with one ml of complete culture medium (DMEM plus 10% fetal bovine serum and 1/100 dilution of penicillin/streptomycin stock, all from Gibco/BRL) and the cells were incubated another 5 hours.

Cell lysates were prepared by rinsing twice in PBS and then treated with 0.5 ml of 1×Reporter Lysis Buffer (Promega). The released and lysed cells were pipetted into 1.5 ml tubes and frozen in $CO_2$/EtOH once and thawed. The crude lysate was then centrifuged 10 minutes to pellet cell debris, and the supernatant was recovered and assayed directly or frozen at −20° C.

The cell lysates were then assayed for CAT, and luciferase or β-galactose activity, and the total protein concentration was determined as described below.

Chloramphenicol Acetyltransferase (CAT) Assay Protocol

This assay was performed generally as follows. First, the following reaction mixture was prepared for each sample:

65 ml 0.25M Tris, pH8/0.5% BSA,

4 μl $^{14}$C-Chloramphenicol, 50 nCi/μl (Dupont), and

5 μl 5 mg/ml n-Butyryl Coenzyme A (Pharmacia)

A CAT standard curve was prepared by serially diluting CAT stock (Promage) 1:1000, 1:10,000 and 1:90,000 in 0.25M Tris, pH8/0.5% BSA. The original stock CAT was at 7000 Units/ml. CAT lysate was then added in a labeled tube with Tris/BSA buffer for final volume of 50 ml.

74 ml of reaction mixture was then added to each tube, which was then incubated for, typically, approximately 1 hour in a 37° C. oven. The reaction was terminated by adding 500 μl Pristane/Mixed Xylenes (2:1) (Sigma) to each tube. The tubes were then vortexed for 2 minutes and spun for 5 minutes. 400 ml of the upper phase was transferred to a scintillation vial with 5 ml Scintiverse (Fisher). The sample was then counted in a Packard scintillation counter.

Luciferase Assay Protocol

This assay was performed generally as follows according to standard procedures. 20 μl of lysate was combined with 100 μl of luciferase assay reagent (Promega) and counted in a scintillation counter (Packard) within 20 seconds (as recommended by Promega).

β-Galactosidase Assay Protocol

This assay was performed generally as follows. A β-gal standard curve was prepared by serially diluting 1:1,000 and 1:9,000 in 0.25M Tris-HCl, pH8.0/0.5% BSA. Stock β-gal was 1,000 Units/ml (Promega). Thus, for the 1:1,000 dilution, 1 μl stock β-gal enzyme was diluted in 1000 μl Tris/BSA buffer, and for the 1:9,000 dilution, 100 μl of the 1:1,000 dilution was further diluted in 1000 μl Tris/BSA buffer.

75 μl of lysate per well (untreated microtiter plate, Corning) was then added. 75 μl 2×β-gal Reaction Buffer (Promega) was added to each tube. Incubation proceeded for, typically, approximately 1–1.5 hours in a 37° C. oven. Plates were read at $A_{405}$ (405 nm) on a microplate reader (Molecular Devices).

Protein Assay Protocol

Samples were prepared in an untreated microtiter plate (Corning). A series of protein standards were prepared in duplicate as follows.

1. 6 μl 1×Reporter Lysis Buffer (Promega)
2. 6 μl 75 mg/ml BSA (Promega)
3. 6 μl 100 mg/ml BSA
4. 6 μl 250 mg/ml BSA
5. 6 μl 400 mg/ml BSA
6. 6 μl 500 mg/ml BSA
7. 6 μl 1000 mg/ml BSA
8. 6 μl 1500 mg/ml BSA Six μl of lysate per well was added, followed by 300 μl Coomassie Protein Assay Reagent (Pierce) per well. The individual sample plates were then read at $A_{570}$ on a microplate reader (Molecular Devices). CAT activity values were normalized to the protein content of the lysate and other parameters as given.

The results of these experiments were as follows.

Anti-Splice Site Oligomers Versus pG1035 and pG1036 (splicing inhibition by antisense oligomers):

| Oligomer chemistry | pG1035 = splicing | | | pG1036 = non-splicing | | |
| --- | --- | --- | --- | --- | --- | --- |
| | Donor | Branch | Acceptor | Donor | Branch | Acceptor |
| PS/DE center | 3263-1 65 ± 11% | 3269-1 72 ± 1% | 3265-1 90 ± 5% | 3263-1 0% | 3269-1 0% | 3265-1 0% |
| PS center | 3264-1 59 ± 2% | 3270-1 56 ± 7% | 3266-1 53 ± 2% | 3264-1 0% | 3270-1 0% | 3266-1 0% |
| All PS | XV-5 32 ± 1% | XV-6 23 ± 15% | XV-7 17 ± 6% | XV-5 35 ± 1% | XV-6 30 ± 4% | XV-7 20 ± 4% |
| PS center, 2'OMe ends | N.D. | N.D. | 3387-1 98 ± 2% | N.D. | N.D. | 3387-1 0% |

Oligomers were transfected into COS-7 cells and lysates were made and assayed as described previously. All oligomers were at 1.0 μM final in the culture medium. The results are given as percent PATENT 214/218 112 inhibition±std error. N.D.=not determined. All samples were performed in triplicate. In the case of the chimeric oligomers (PS/DE center and PS center) the expression of the non-splicing pG1036 CAT was slightly higher in oligomer treated versus untreated cells, so the expression of pG1035 was normalized to pG1036 expression. All results were normalized to total protein and luciferase counts.

The results show specific inhibition of CAT expression when the splice site sequences are targeted using the chimeric oligomers. In the case of all phosphorothioate oligomers, pG1036 expression was inhibited approximately as well as pG1035, revealing large non-specific effects on gene expression. In addition, the incorporation of 2'-O-methyl groups in the flanking terminal portions of the splice site acceptor oligomer 3387-1 and lengthening the PS center from five to seven continuous phosphorothioate backbone linkages increases the antisense activity against the splice acceptor site target significantly but does not increase non-specific activity against the control target.

Chimeric Oligomers Targeted Against the AUG of CAT Inhibit Expression:

Oligomers were transfected into COS-7 cells and lysates were made and assayed as described previously. All oligomers were at 1.0 μM final in the culture medium. The results are given as percent inhibition±std error. N.D.=not determined. All samples were performed in triplicate. In the case of the chimeric oligomers (PS/DE center and PS center) the expression of the non-splicing pG1036 CAT was slightly higher in oligomer treated versus untreated cells, so the expression of pG1035 was normalized to pG1036 expression. All results were normalized to total protein and luciferase counts. The control oligomer (3269-1) gave no inhibition, demonstrating that the inhibition observed for the chimeras that match the pG1040 mRNA was specific.

In conclusion, these results indicate the ability to down-regulate CAT activity using chimeric oligomers introduced into cultured COS-7 cells via cationic lipids.

The targets have been AUG sites (present in both the pre-mRNA and mature mRNA) and intronic sites (present only in pre-mRNA in the nucleus of any cell). The chimeric oligomers with both PS/DE and PS centers have proven to be more specific than all-PS oligomers and control chimeras. Both target-specific and oligomer-specific controls were included, demonstrating that the results are based on sequence-specific antisense effects.

Example 42

Specificity Determination

Singly and multiply mismatched, complementary gene targets and oligomers allow cross-over experiments to estimate oligomer discrimination of perfect match targets from imperfect non-specific targets. The present example shows the preparation of CAT mRNA targets having 0- or 4-base mismatches with respect to the oligomers used in Example 41, as well as the effect of various mismatches on the specificity and activity of oligomers of the invention.

| | 5'AUG Target | | 3'AUG Target | | Control No Target | No oligomer |
| --- | --- | --- | --- | --- | --- | --- |
| Oligomer | 3258-1 | 3260-1 | 3261-1 | 3262-1 | 3269-1 | None |
| Chemistry | PS/DE center | PS center | PS/DE center | PS center | PS/DE center | No treatment |
| % Inhibition | 43 ± 19% | 72 ± 28% | 96 ± 7% | 97 ± 4% | 4 ± 14% | 0 ± 15% |

Oligomers were transfected into COS-7 cells and lysates made and assayed as described previously. All oligomers were at 1.0 μM final in the culture medium. Oligomer 3269-1 was a control that does not have a target site in pG1040, because the CAT gene does not contain a splice site. Results are expressed as % inhibition±error. Each oligomer was tested in triplicate.

Chimeric oligomers targeted against the 5' AUG site (3258-1, 3260-1) were effective at blocking expression of the CAT mRNA (43–72% inhibition, respectively). Chimeric oligomers targeted against the 3' AUG site (3261-1, 3262-1) were even more effective, giving 96 and 97%

```
           pG1040 (UCAT) and pG1042 (UCAT 4 mm) 5' untranslated
                regions and amino termini and oligomers:

Wild-type CAT SEQ ID NO:16:

5'                            +1                                         3'
                               Met Glu Lys Lys Ile Ser Gly Tyr Thr Thr
uuu uca gga gcu aag gaa gcu aaa aug gag aaa aaa auc acu gga uau acc acc pG1040, UCAT SEQ ID NO:17:
5'                            +1                                         3'
                               Met  Glu Lys Lys Ile Ser Gly Tyr Thr Thr
agu gca gga gcu aag gaa gcu acc aug  gag aag aag auc acu gga uau acc acc
3' (cgt cct cga ttc ctt cga tgg tac) (ctc ttc ttc tag tga cct ata tgg) 5'
           XV-1 SEQ ID NO:7                   XV-2 SEQ ID NO:8 pG1042, UCAT 4 mismatch SEQ ID NO:20
5'                            +1                                         3'
      *    *   **              *   *        *   *
                               Met  Asp Arg Lys Ile Thr Gly Tyr Thr Thr
agu gca aga guu gcg gaa gcu acc aug  gac agg aag auu acg gga uau acc acc
3' (cgt tct caa cgc ctt cga tgg tac) (ctg tcc ttc taa tgc cct ata tgg)
           XV-3                                  XV-4
```

Mismatches between pG1040 (UCAT) and pG1042 (UCAT) 4 mm are marked with asterisks (*). All other bases in the mRNAs produced by these plasmids are identical. The sequence of the wild-type CAT gene is shown for comparison. The first adenosine of the open reading frame is designated +1. The oligomer target sites are underlined.

Plasmids pG1040 and pG1042 were created using synthetic DNA PCR primers to amplify precisely mutated DNA fragments. The fragments were then cloned as Hind III (5' end), Not I (3' end) fragments into the vector pRc/CMV (Invitrogen) and positive clones were identified.

It will be noted that, for a given oligomer against either of these target genes, a control target is provided having a precisely defined degree of mismatch. This allows testing of one oligomer against a perfect match and precisely-defined mismatch targets, as exemplified by the following:

In this case, the oligomer XV-2 is a perfect match to pG1040, but has four mismatches to pG1042. The relative effects of this one oligomer against two target mRNAs that are identical except in the four known mismatch bases can thus be determined.

In addition, mismatches in the target gene can be precisely controlled by the sequence of the PCR primers used in the amplification procedure, and a defined sequence of precise mismatches can be created such as a series in the region just 5' of the AUG codon. This is shown in the following example:

```
           pG1040, UCAT SEQ ID NO:17:

5'                            +1                                         3'
agu gca gga gcu aag gaa gcu acc aug gag aag aag auc acu gga uau acc acc
                                    ||| ||| ||| ||| ||| ||| ||| |||
                                   (ctc ttc ttc tag tga cct ata tgg)
                                         XV-2 SEQ ID NO:2 pG1042, UCAT 4 mismatch SEQ ID NO:20:

agu gca aga guu gcg gaa gcu acc aug gac agg aag auu acg gga uau acc acc
                                    ||* |*| ||| ||* ||* ||| ||| |||
                                   (ctc ttc ttc tag tga cct ata tgg)
                                         XV-2 SEQ ID NO:2
0

55

5'                     +1                                         3'
                                          Met Glu Lys Lys Ile Ser Gly Tyr Thr Thr
                  agu gca gga gcu aag gaa gcu acc aug gag aag aag auc acu gga uau acc acc SEQ ID NO:17
                       3' cct cga ttc ctt cga tgg tac 5' SEQ ID NO:26

1 mismatch:
                  agu gca gga gcu aag gaa gcu Ccc aug gag aag aag auc acu gga uau acc acc SEQ ID NO:21
```

-continued
```
    3' cct cga ttc ctt cga Tgg tac 5' SEQ ID NO:26

2 mismatches:
agu gca gga gcu aag gaa Acu Ccc aug gag aag aag auc acu gga uau acc acc SEQ ID NO:22
    3' cct cga ttc ctt Cga Tgg tac 5' SEQ ID NO:26

3 mismatches:
agu gca gga gcu aag Uaa Acu Ccc aug gag aag aag auc acu gga uau acc acc SEQ ID NO:23
    3' cct cga ttc Ctt Cga Tgg tac 5' SEQ ID NO:26

4 mismatches:
agu gca gga gcu Gag Uaa Acu Ccc aug gag aag aag auc acu gga uau acc acc SEQ ID NO:24
    3' cct cga Ttc Ctt Cga Tgg tac 5' SEQ ID NO:26

5 mismatches:
agu gca gga Ccu Gag Uaa Acu Ccc aug gag aag aag auc acu gga uau acc acc SEQ ID NO:25
    3' cct Cga Ttc Ctt Cga Tgg tac 5' SEQ ID NO:26
```

Here, the target sequence within the mRNA to be studied extends from −18 to +3. Mismatches in mutant mRNAs relative to the top sequence are shown in bold upper case. The oligomer sequence in this example, a 21 mer, is shown beneath each mRNA and is invariant. Mismatches in the oligomer to each subsequent mRNA are shown in upper case.

Using this method of increasing the number of precisely known mismatches in otherwise identical targets, one can accurately determine the specificity of various oligomer chemistries (e.g. phosphorothioates versus chimeras) and modes of action (e.g. steric blockers versus RNaseH cleavers).

Tests were undertaken to study the effects on activity and specificity caused by variations in the location of the charged-backbone RNasH-activating region within a chimeric oligonucleoside, and by various mismatches incorporated into the base sequence of an oligonucleoside and/or in the target mRNA. The chimeric compounds listed below (see also Example 41) were assayed for antisense activity against both the pG1040 (UCAT) target and the pG1042 (UCAT) 4-base mismatch control. The oligomer sequences were as follows.

The phosphorothioate linkages in these chimeric oligomers are immediately 5' of the underlined bases. It will be seen that the position of the phosphorothioate core is sequentially shifted in position with respect to the target mRNA.

Antisense activity was assayed against both pG1041 (UCAT) and pG1042 (UCAT) using procedures as generally described in Example 41, except that 0.5 μM oligomer was used. It was demonstrated that mismatches in the phosphorothioate core and the position of the core in chimeric oligomers greatly affected antisense activity. The following table sets forth the percentage of gene expression (±error) measured for each of the tested oligomers.

```
    pG1040 (UCAT) target mRNA and antisense oligomers:

+1  +4                      +27
        |   |                        |
        Met Glu Lys Lys Ile Ser Gly Tyr Thr ... ...
mRNA ... aug gag aag aag auc acu gga uau acc ... ...

3637-1   3' ctc ttc ttc tag tga cct ata tgg 5' SEQ ID NO:8

3638-1   3' ctc ttc ttc tag tga cct ata tgg 5' SEQ ID NO:8

3262-5   3' ctc ttc ttc tag tga cct ata tgg 5' SEQ ID NO:8

3636-1   3' ctc ttc ttc tag tga cct ata tgg 5' SEQ ID NO:8 x
3639-1   3' ctc ttc ttc tag tgg cct ata tgg 5' x
3640-1   3' ctc ttc ttc tag tga act ata tgg 5'

XV-2     3' ctc ttc ttc tag tga cct ata tgg 5' SEQ ID NO:8
```

|        | Oligomer number |          |         |         |         |          |
| ------ | --------------- | -------- | ------- | ------- | ------- | -------- |
| Target | 3637-1          | 3638-1   | 3262-5  | 3636-1  | 3639-1  | 3640-1   |
| pG1040 | 79 ± 5%         | 37 ± 3%  | 35 ± 7% | 70 ± 3% | 98 ± 5% | 103 ± 5% |
| pG1042 | 89 ± 3%         | 102 ± 2% | 88 ± 4% | 120 ± 8%| 93 ± 2% | 115 ± 3% |

The results show the effect of moving the RNAseH-activating phosphorothioate core within the oligomer. The position of the phosphorothioate core and/or the base composition of the phosphorothioate core has a large effect on antisense activity, as seen by comparing 3637-1, 3638-1, 3262-5 and 3636-1. A more central position within the chimera is most active, but some activity is detected even when the core is near the ends of the chimera.

A single base mismatch (denoted by an "x" above the sequences shown above) within the RNaseH phosphorothioate core sequence of the chimeric oligomers eliminates antisense activity in this eukaryotic cell culture assay, as seen by comparing 3639-1 and 3640-1 with 3262-5. In a separate experiment using the same assay system, the all-phosphorothioate 24 mer XV-2 gave 90% inhibition of pG1040 (UCAT) expression and approximately 50% inhibition against pG1042 (UCAT) even though there were four mismatches in the case of the latter target. This indicates that all-phosphorothioate oligomers are far less specific than chimeric oligomers containing short regions of phosphorothioate linkages, inasmuch as even a single mismatch between the chimeric oligomers 3639 and 3640 and the pG1040 target abolished activity, whereas four mismatches in the case of XV-2 and pG1042 reduced activity by less than 50%.

Example 43

Increased RNaseH Cleavage Rate with Chimeras Containing Chirally Enriched Oligonucleoside Methylphosphonate End-blocks The present example demonstrates that chimeric oligomers with enhanced binding affinity promote RNaseH cleavage of RNA target strands at a faster rate than lower affinity oligomers having the same base sequence. Chimeric oligonucleosides containing either racemic or chirally pure ($R_p$) methylphosphonates were examined for their ability to activate RNaseH.

The following chimeric oligomers were used in this example: 1

```
Sequence = 3'-[CCTGTTG][TACGT][ACCTTCTG]-5' SEQ ID NO:6

2681-1    [MP]        [PS/DE]     [MP]

3214-1    [MP(Rp)/DE] [PS/DE]     [MP(Rp)/DE]
```

Each of these chimeric oligomers was synthesized according to the method described in Example 30. A complementary synthetic RNA target was prepared according to the method given in Example 28. This oligomer has the following sequence: 1

```
    5'-GGACAACAUGCAUGGAAGAC-3' SEQ ID NO:27
```

A $^{32}$P-label was coupled to the 5'-end of this oligomer using [γ-$^{32}$P]-ATP and T4 polynucleotide kinase according to a procedure commonly known in the art.

RNaseH from bacterial E. coli was purchased from Promega Corp. (Madison, Wis.). Buffer A, used for the RNaseH reactions contained 20 mM KCl, 9 mM $MgCl_2$, 1 mM 2-mercaptoethanol, 250 μg/ml of BSA (Promega Corp.) and 100 u/ml of RNasin (Promega Corp.).

A mixture of 5'-$^{32}$P-labelled RNA target (approximately 80,000 dpms, 5×10$^{-10}$ M) was mixed with 1 molar equivalent of either chimeric oligomer in reaction Buffer A (total volume=98 microliters). This mixture was incubated at 37° C. for 1 hour. Next, RNaseH (1.1 microliters, 30 units/mL, final concentration=2×10$^{-9}$ M) was added and the resulting mixture was incubated at 37° C. Aliquots (15 microliters) were removed at specified time intervals, diluted with EDTA (0.5 M, 3 microliters) frozen on dry ice and then stored at −20° C. The products of RNA cleavage were analyzed by gel electrophoresis using a 15% polyacrylamide/7 M urea gel (20 cm×30 cm×0.5 mm i.d.) equilibrated in 1×TBE buffer (pH 8.2). The gel was electrophoresed at 1200 volts for approximately three hours. Bands on the wet gel were visualized by phosphorimager analysis using a Bio-Rad Model GS-250 Molecular Imager (Calabasas, Calif.).

Figure 5:
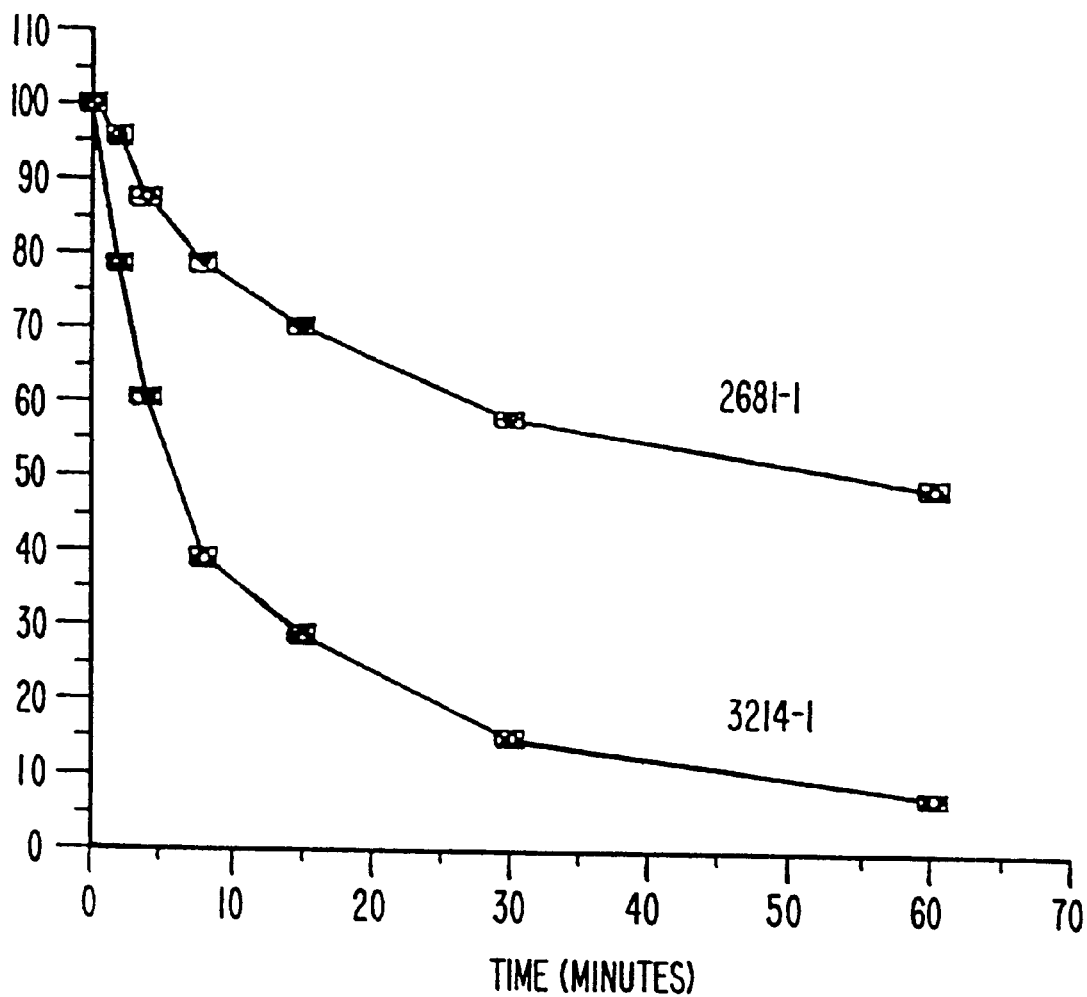
FIG. 5 is a graph showing RNaseH activity of a chirally-selected compound of the present invention, versus a non-chirally-selected compound, over time.
Figure 6A:
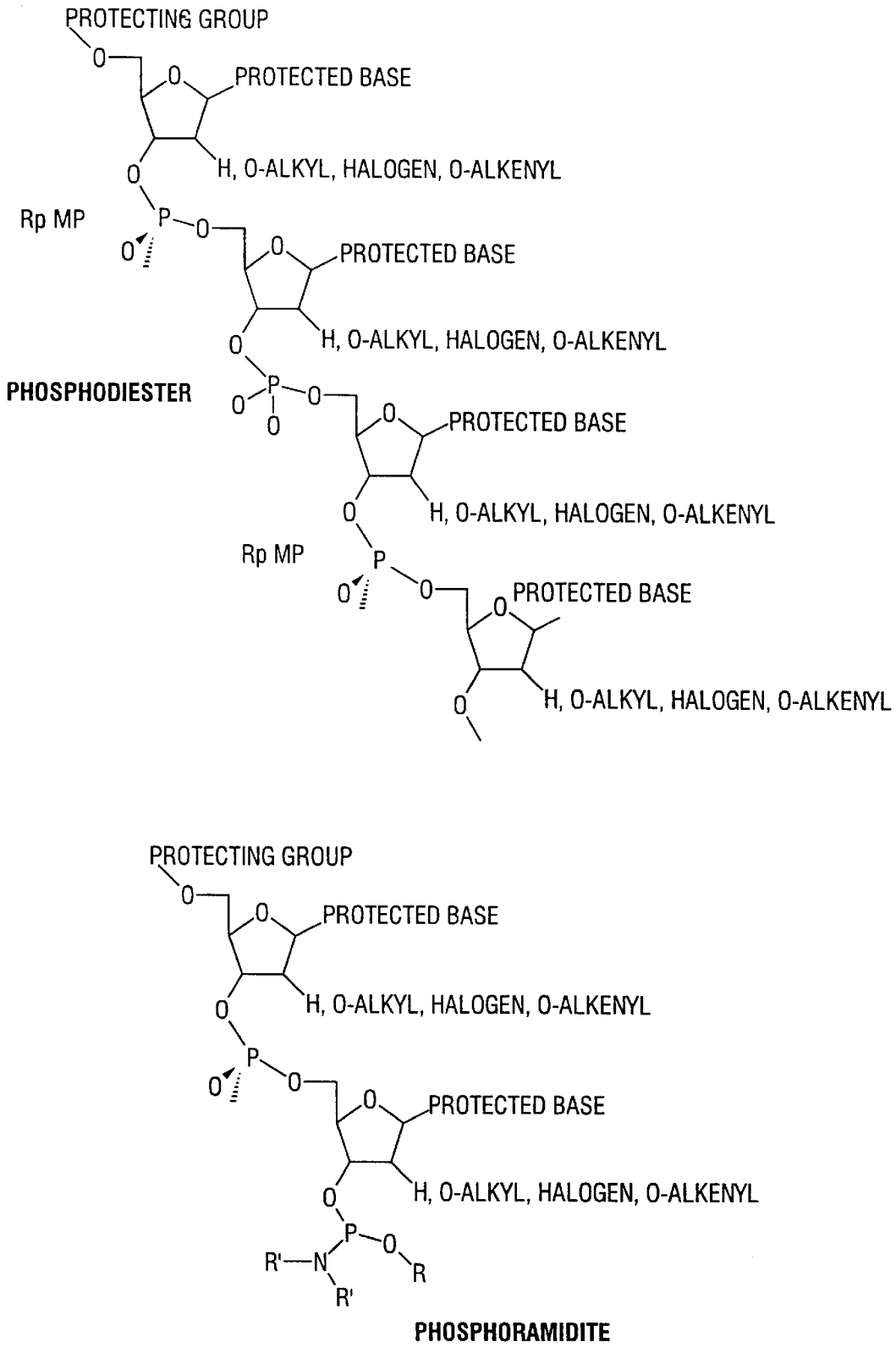
FIGS. 6–10 depict sythons and intermediates useful in constructing compounds of the present invention.
Figure 6B:
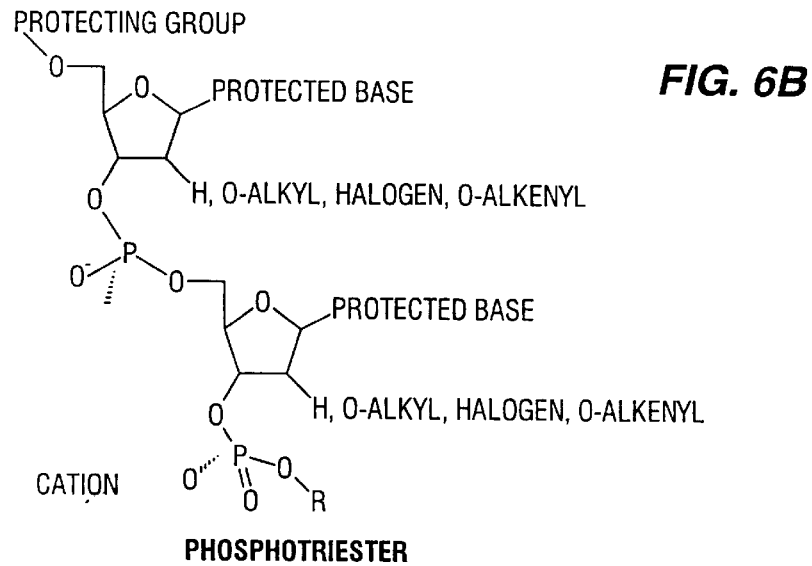
Figure 6B:
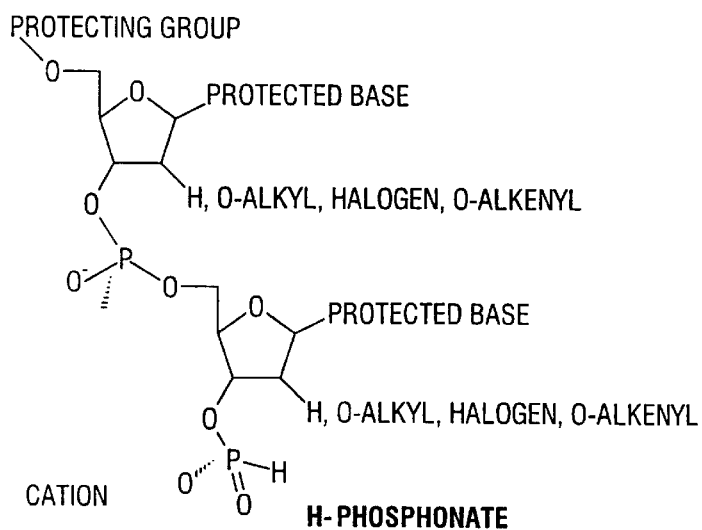
Figure 6B:
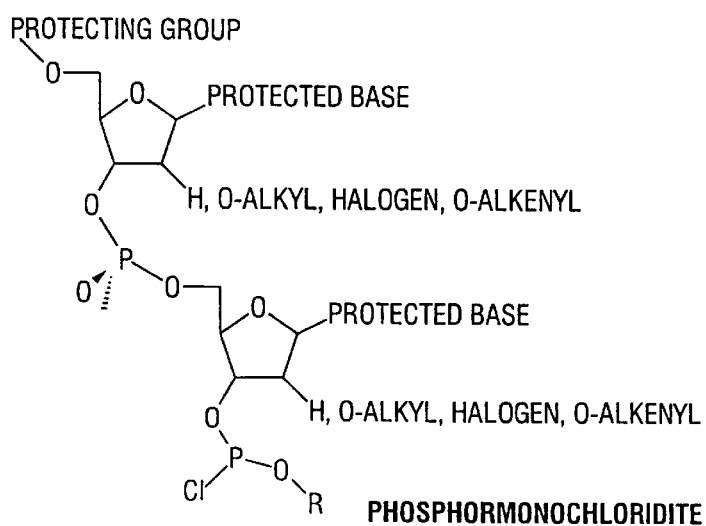
Figure 7:
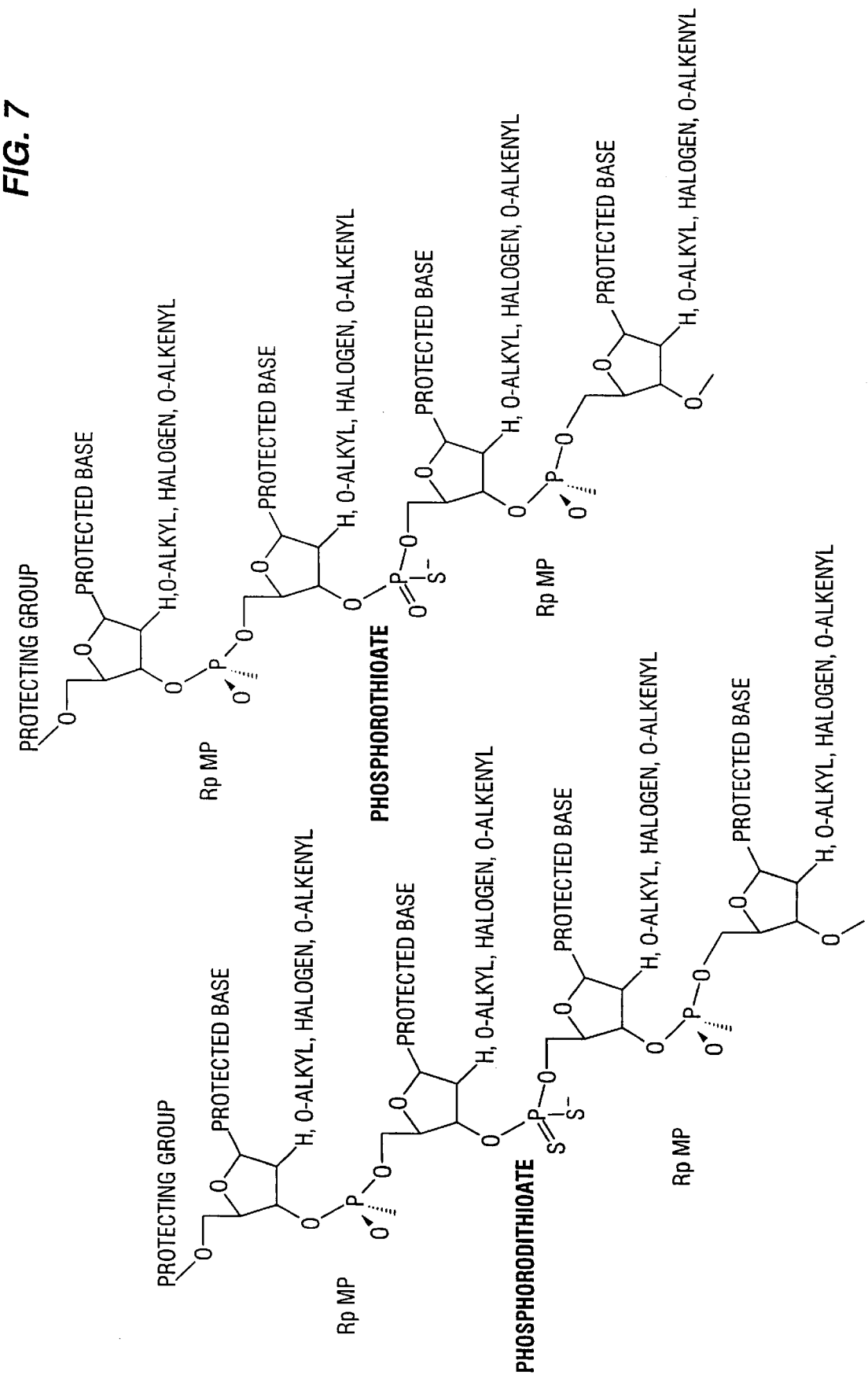
Figure 8:
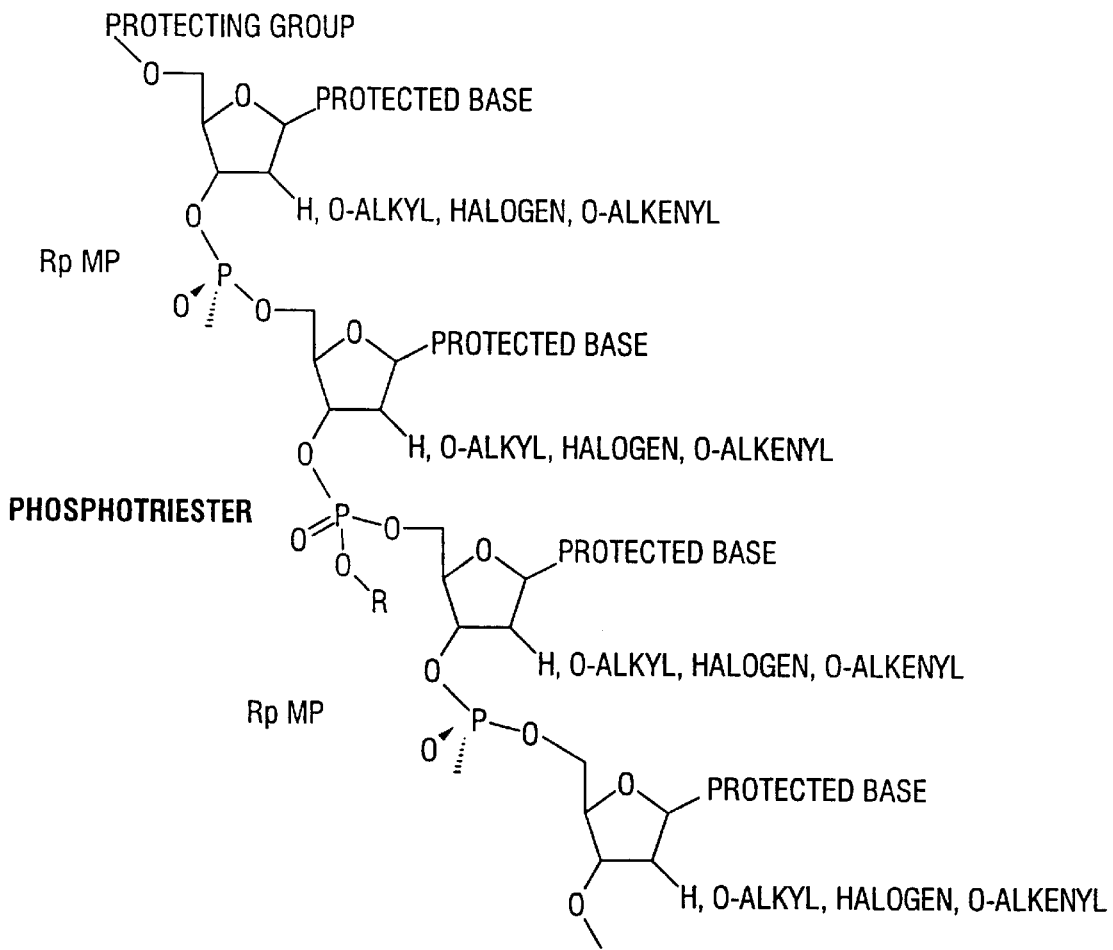
Figure 9A:
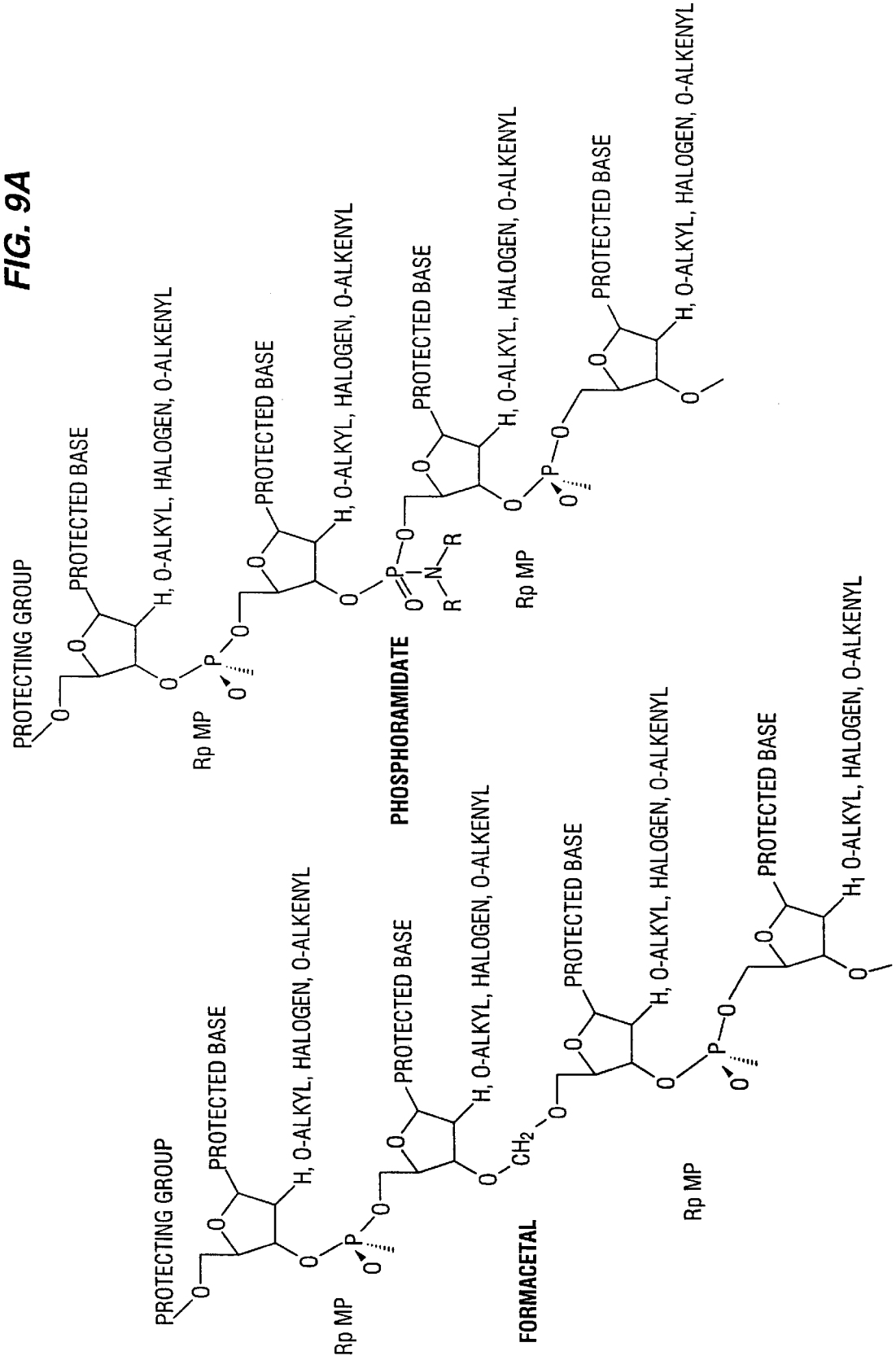
Figure 9B:
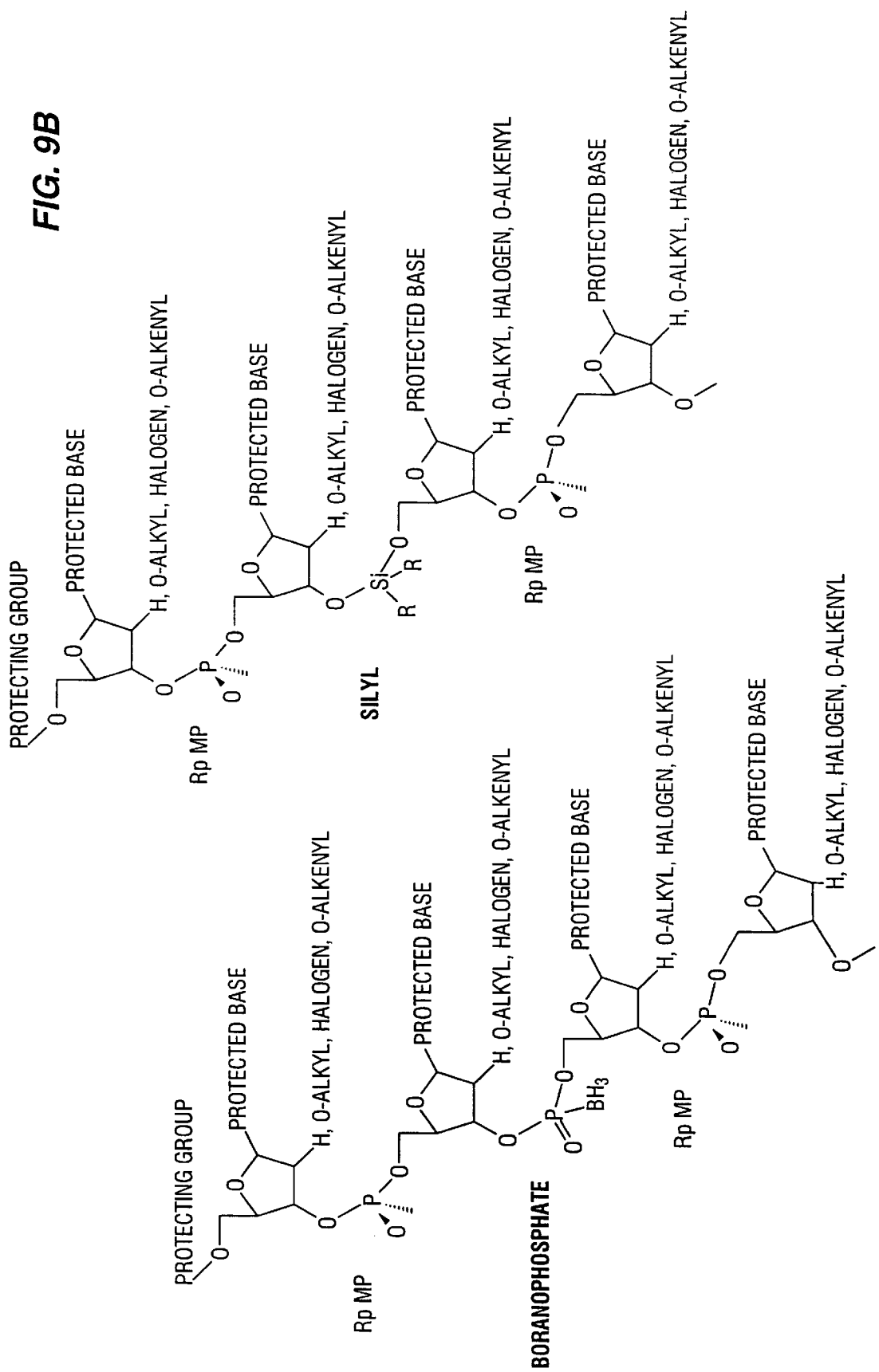
Figure 10:
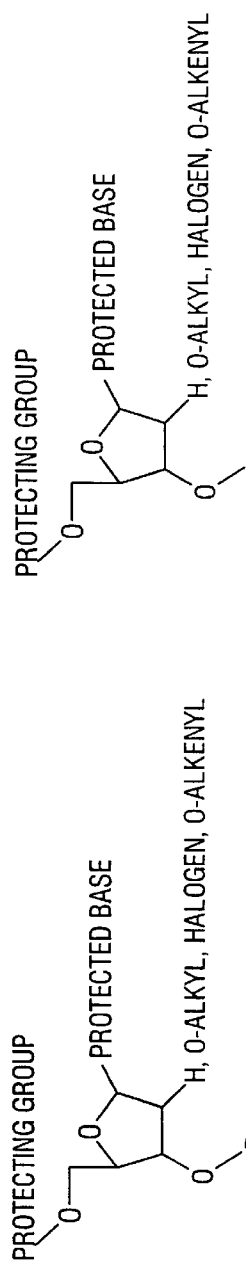
Figure 10:
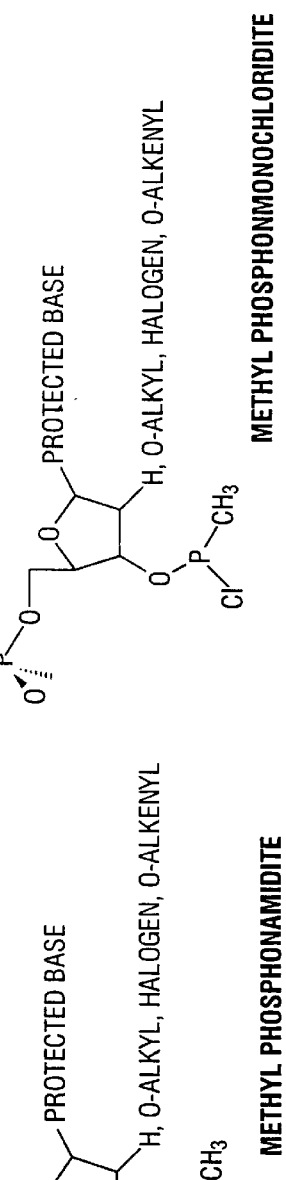
Figure 10:
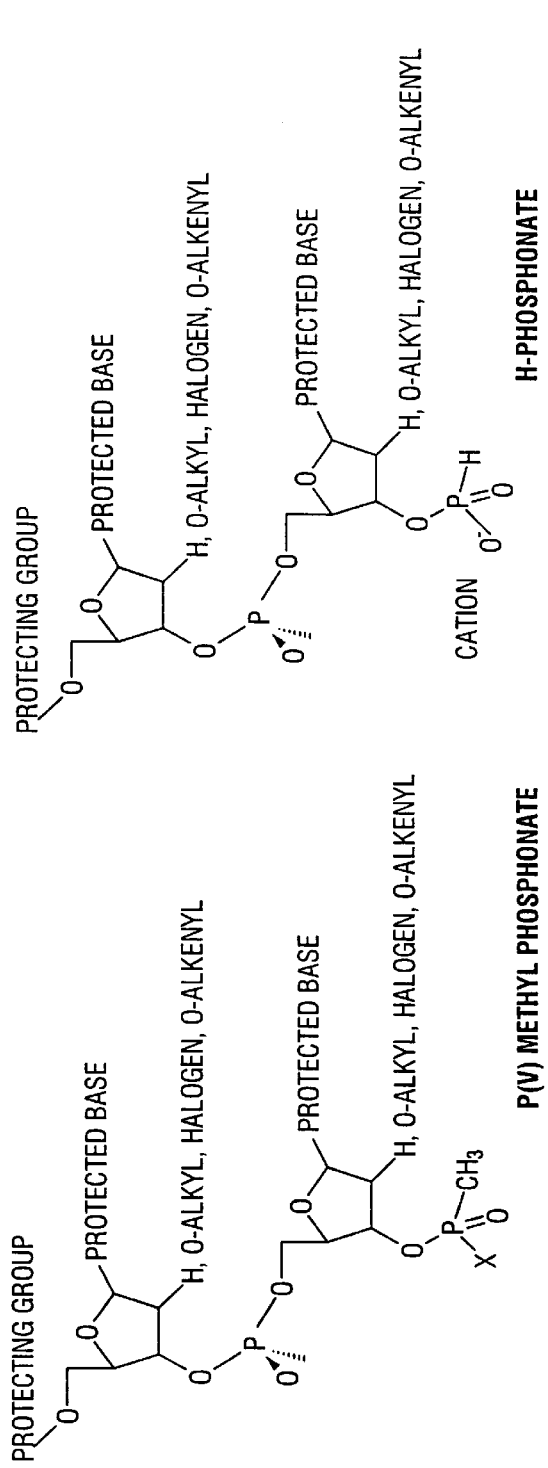

Site-specific RNaseH-mediated cleavage was observed with both chimeric oligomers. The lengths of the fragments were estimated according to their electrophoretic mobility. According to this analysis, it was determined that cleavage was limited to the center of the RNA target sequence. That is, cleavage was limited to the position of the RNA strand complementary to the negatively charged segment of each chimeric oligomer. A difference in the rate of RNaseH mediated cleavage was detected for the two different chimeric oligomers as shown in FIG. 5.

It is seen that the rate of RNA hydrolysis in the presence of chimeric oligomer 3124-1 (containing alternating MP($R_p$)/DE backbone segments at the 3'- and 5'-ends) is about 10 times faster than that for the other chimeric oligomer 2681-1 (containing racemic MP backbone segments).

Example 44

Effect of 2'-Sugar Substitution Location on Chimeric Oligomer Cleavage Activity

The effect of the location of 2'-sugar substituents relative to the RNaseH-activating region of the present oligomers was studied by measuring the cleavage activity of differently-substituted chimeric oligomers against a target RNA sequence. A synthetic 20 mer RNA molecule, designated 3593, containing an AUG sequence near the targeted cleavage site was prepared having the following sequence:

1

```
3593 (target RNA): 5' AG AGA GAG AUG CAG AGA GAG 3'
```

Chimeric 20mer RNaseH-activating oligonucleosides 3463, 3465 and 3466 were synthesized using appropriate dimer synthon methods as generally described above. These compounds included a central RNaseH-activating region comprising five consecutive phosphorothioate-linked deoxyribonucleosides (shown in parentheses below) flanked by non-RNaseH-activating regions linked by alternating MP($R_p$)/DE linkages. Selected nucleoside sugars in the flanking regions of chimeras 3463 and 3465 contained 2'-O-methyl substitutions, indicated by the underlined capitalized nucleoside abbreviation letters below (the target 3593 sequence is also depicted to show target complementarity):

```
3593: 5' AG AGA GA G AUG C AG AGA GAG 3' (target
RNA)

3563: 3' uc UcU cU(c tac g)UcU cUc 5'

3465: 3' uc UCU Cu(c tac g)uc UCU CUC 5'

3466: 3' uc ucu cu(c tac g)uc ucu cuc 5'
```

As with other chimeric oligomer compounds disclosed herein, the charged (here, phosphorothioate) linkages associated with the RNaseH-activating region are situated 5' to each of the nucleosides shown in parentheses. Thus, compounds 3463, 3465 and 3466 above each include a stretch of five consecutive, central phosphorothioate ({PS}) linkages, flanked on either side by a chirally-selected $R_p$-methylphosphonate ({MP($R_p$)}) linkage, as follows (shown 3' to 5'):

```
. . . c{DE}u{MP(R_p)}(c{PS}t{PS}a{PS}c{PS}g){PS}u{MP(R_p)}c{DE}u . . .
```

The underlined phosphorothioate linkage shown above [in the segment . . . u{MP($R_p$)}(c{PS}t . . . ] can be incorporated into the compounds using dimer synthon methods as described, for example, in Example 13 above. The remaining non-RNaseH-activating portions of the chimeric compounds include alternating MP($R_p$)/DE linkage segments incorporated, for example, by successive addition of appropriate dimers following the support-bound "uc" dinucleotide sequence at the 3'-terminus of the compounds (see, e.g., Examples 8, 9 and 17A above). Thus, 2'-sugar substitutions shown above for compounds 3463 and 3465 can be achieved by successively incorporating suitable 2'OMe U{MP($R_p$)}c{DE} or 2'OMeU{MP($R_p$)}2'OMeC{DE} dimers into the respective oligomers.

To assess the RNaseH cleavage activity of the foregoing chimeric oligomers, 320 μl of a mixture of 5'-$^{32}$P-labelled RNA target compound 3593 (160 dpm) and the selected test oligomer (1:1 molar ratio; concentrations 0.5 nM) was incubated in Buffer A at 37° C. for one hour to achieve complementary complex formation and equilibration. (Buffer A: 20 mM KCl, 9 mM MgCl$_2$, 1 mM 2-mercaptoethanol, 250 μg/ml BSA [Promega], 100 u/ml RNasin [Promega].) A 20 μl aliquot was removed as a time zero sample and 3.3 μl of a 2 nM solution of bacterial (*E. coli*) RNaseH (Promega) in Buffer A was added (final concentration of enzyme in solution was 0.022 nM). The reaction mixture was kept at 37° C. Twenty microliter aliquots were removed from the mixture at appropriate time intervals and the reaction was stopped by adding 2 μl of 0.5 M sodium EDTA solution and then freezing on dry ice. The products of RNA cleavage were analyzed in 15% PAGE (20 cm×30 cm×0.5 mm) containing 7 M urea and 1×TBE buffer (pH 8.1). Gels were run at 1200 V for 2 hours. Quantitative kinetic data were obtained by integration of the volumes of the bands by means of Phosphor-image analysis.

Figure 11:
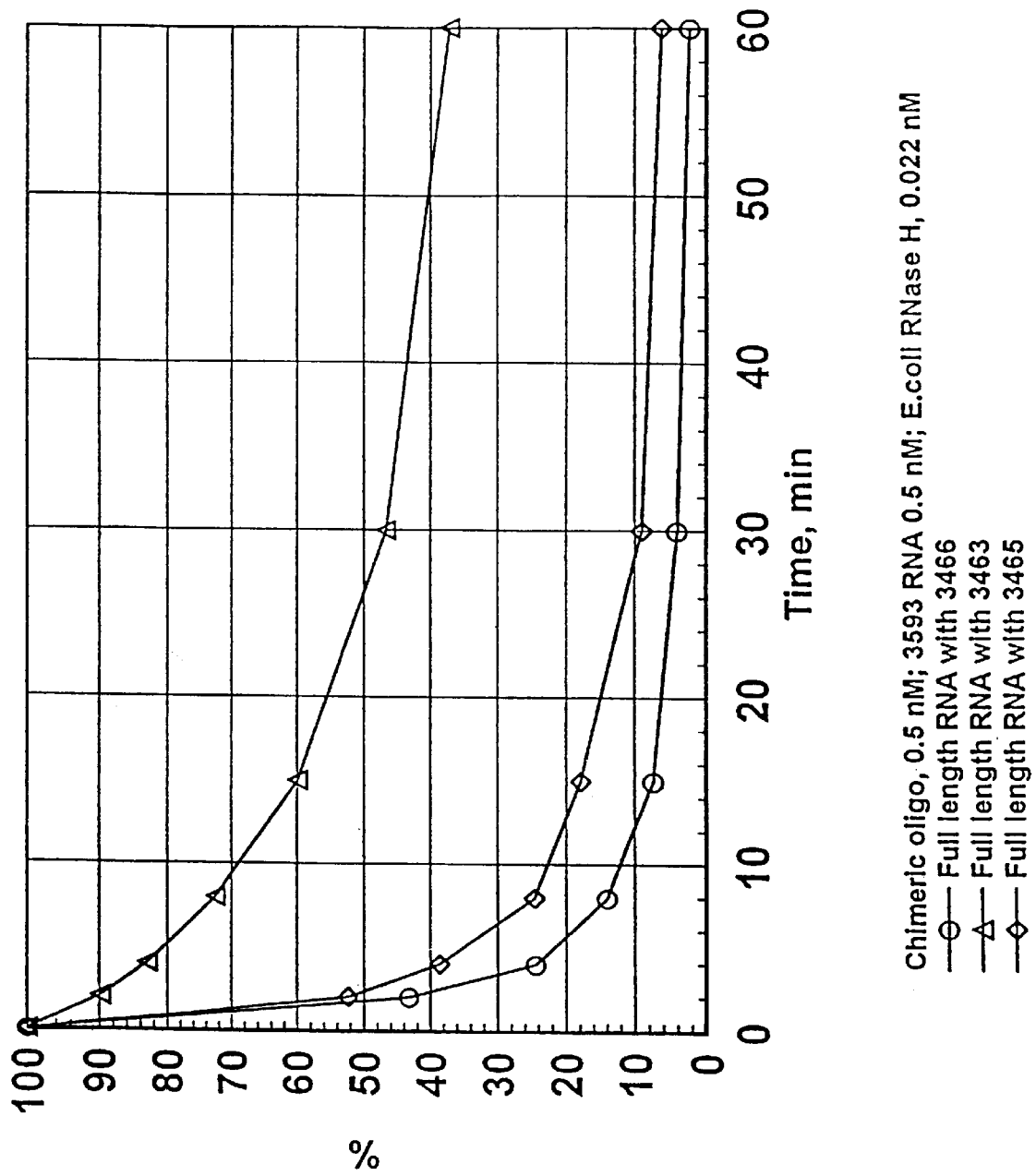
FIG. 11 is a graph showing kinetic data relating to RNA cleavage by various 2'-sugar-substituted and unsubstituted compounds of the invention.

The kinetic curves for this example are shown in FIG. 11. A significant decrease (about 10-fold) in the overall rate of RNA cleavage was found when 2'-O-methyl nucleoside units were positioned next to the central phosphorothioate RNaseH-activating region (compound 3463, triangle data points) as compared to the chimeric compound containing all 2'-H nucleosides (compound 3466, circles). The initial number of cleavage products was reduced for compound 3463 as compared to compound 3466 (2 instead of 3). When a 2'-H nucleoside instead of a 2'-O-methyl nucleoside was incorporated on the border of the alternating methylphosphonate/phosphodiester 5'-end-block and phosphorothioate regions (compound 3465, diamonds), no significant decrease in cleavage rate was found, and the number of cleavage products also did not change as compared to that obtained with compound 3463.

This example demonstrates that the presence of a non-hydroxy 2'-sugar substituent adjacent to the RNaseH cleavage site has a significant diminutive effect on RNaseH cleavage activity and that even a single 2'-O-methyl substituent may be responsible for the reduction in cleavage activity. In contrast, the use of a 2'-substitution that is removed from the RNaseH-activating region by one or two nucleosides has a negligible effect on RNaseH binding and/or cleavage activation.

Example 45

Activity of Chimeric Oligonucleoside Compounds Against HPV Targets

This example describes experiments using various chimeric oligonucleosides of the invention targeted against human papilloma virus (HPV) gene sequences.

A. Preparation of Plasmid Expressing a Polycistronic E6/E7 mRNA

An expression vector having an insert coding for HPV11 E6/E7 was prepared using the expression vector pRc/CMV (Invitrogen). The plasmid pRC/CMV was linearized with Hind III. The recessed 3' ends were filled with the 5'–3' polymerase activity of T$_4$ DNA polymerase. A full length clone of HPV-11 cloned at the BamHI Site in pBR322 was digested with the restriction enzymes Bst II and Hinf I. The 873 base pair fragment containing the E6 and E7 open reading frames was purified on agarose gel. The restriction ends of this fragment were modified by filling in the recessed 3'-ends with T$_4$ DNA polymerase.

The vector and insert were ligated with T$_4$ DNA ligase and transformed into DH5α *E. Coli*. Recombinants were screened for appropriate insert and orientation as well as E6/E7 transcription and translation activity.

This plasmid (pRc/CMVII-E6/E7) was used in the cell free translation system described below.

B. Preparation of Plasmid Having an E2 Insert

An expression vector having an HPV-11 E2 insert was prepared using pRc/CMV (Invitrogen). The plasmid was linearized with Hind III, followed by treatment with calf thymus alkaline phosphatase. To isolate the E2 open reading frame, a full length clone of HPV-11, cloned at the Bam HI site in pBR322, was digested with the restriction enzymes XmmI and SspI. The recessed 3' ends were filled in with the 5'–3' polymerase activity of the Klenow fragment of DNA polymerase I. Hind III linkers were then added. The 1309 base pair fragment containing the complete E2 ORF was agarose gel purified. The modified vector and E2 insert were ligated with $T_4$ DNA ligase and transformed into DH5α *E. Coli*. Recombinants were screened for appropriate insert, transcription and translation.

This plasmid (pRc/CMVII-E2) was used in the cell-free translation system described below.

C. Preparation of Plasmid Having Monocistronic E7 Insert

An expression vector having an HPV-11 E7 insert was prepared using pcDNA-1 (Invitrogen). The plasmid pcDNA was digested with Bam HI and with Xba I. A fragment containing the complete open reading frame of HPV-11 (from −30 through the termination codon) flanked by Bam HI and Xba I restriction sites was prepared by PCR using standard protocols. The digested vector and fragment were ligated with $T_4$ DNA ligase and transformed into MC 1061/P3 cells. Recombinants were screened for appropriate insert, transcription and translation.

This plasmid (pcDNA E7) was used in the cell-free translation system and in the transient expression assay described below.

D. Demonstration of Activity of Antisense Chimeric Oligomers Targeted to HPV-11 E7 in Cell Free Translation Extracts Mono-cistronic (100 nM) HPV-11 E7 or polycistronic (50 nM) HPV-11 E6/E7 RNA was co-translated with chloramphenicol acetyl transferase (CAT) RNA (2 to 10 nM) in cell-free rabbit reticulocyte extracts (Promega). The contents of each assay system was as follows.

| COMPONENT | FINAL CONCENTRATION |
|---|---|
| In vitro transcribed un-capped RNA | (As noted above) |
| $^{35}$S-cysteine | 0.8 mCi/mL |
| Amino acids mixture, cysteine deficient | 20μ each |
| Rabbit reticulocyte lysate | 72° by volume |
| RNAsin (Promega) | 0.5 units/μL |
| Oligomer | 1 to 10 μM |

Cell free translation was performed at 37° C. for 60 minutes and was stopped by addition of SDS gel loading buffer and incubation at 95° for 3 minutes. Translation of E7 was evaluated after immunoprecipitation with αE7 goat antiserum and protein A sepharose, followed by SDS-PAGE and phosphoimage analysis. This protocol was also used in the cell-free translations referred to below.

E. Demonstration of Activity of Antisense Oligomers in a Cell-Free RNAseH Cleavage Assay In vitro transcribed, uncapped mono-cistronic RNA was prepared by transcribing plasmid pcDNA11E7 with RNA polymerase (Ambion MegaScript). The E7 RNA was incubated at a concentration of 100 nM in the presence of 0.04 units 1 μL *E. Coli.* RNAseH (Promega), 3.5 mM $MgCl_2$, 25 mM KCl, 70 mM NaCl and 20 mM potassium acetate at 37° C. for 30 minutes. Reactions were stopped by addition of formamide gel loading buffer followed by heating to 100° C. for 5 minutes.

Samples were analyzed by 4% Urea-PAGE analysis, followed by staining with ethidium bromide. Percentages of cleavage of E7 mRNA, in the presence of RNAseH, of methylphosphonate chimeric oligomers 2657-1, 3169-1, 3214-1, 3257-1, 3241-1 and 3236-1 are shown in the table below. Good dose response effects were obtained for all the oligomers at the concentrations tested. The order of potency was 3169-1≈3257-1>3214-1≈2657-1>3236-1>3241-1. All oligomers showed good specificity, cleaving E7 mRNA in one position.

| | | Oligomer concentration (μM) | | | |
|---|---|---|---|---|---|
| Oligomer | Backbone | 0.01 | 0.1 | 1 | 10 |
| 3169-1 | [MP($R_p$)/DE]-[DE]$_5$-[MP($R_p$)/DE] | 7 | 45 | 85 | 100 |
| 3214-1 | [MP($R_p$)/DE]-[PS/DE]$_5$-[MP($R_p$)/DE] | 2 | 20 | 50 | 80 |
| 3257-1 | [MP($R_p$)/DE]-[PS/DE]$_7$-[MP($R_p$)/DE] | 4 | 40 | 75 | 100 |
| 3341-1 | 2'OMe[MP($R_p$)/DE]-[PS]$_7$-2'OMe[MP($R_p$)/DE] | 5 | 40 | 60 | 60 |
| 3336-1 | 2'OMe[MP($R_p$)/DE]-[PS/DE]$_7$-2'OMe[MP($R_p$)/DE] | 5 | 50 | 60 | 65 |

Results are percentage of cleavage of E7 mRNA. Estimated values were obtained by visual inspection of the gel.

F. Demonstration of Activity of Antisense Oligomers in Transiently Transfected COS-7 Cells COS-7 cells were seeded at $1\times10^5$ cells/well in 24 well plates and then cultured overnight in cell culture media (90% DMEM, 10% fetal bovine serum and 50 I.U./ml penicillin, 50 mg/ml streptomycin and 0.25 μg/ml amphotericin B). After 24 hours the cells were approximately 80 to 90% confluent. A transfection cocktail of 2.5 μg/mL pcDNA 1 E7, 50 μg/mL Transfectam (Promega) and varying concentrations of oligomer was prepared and incubated for 15 minutes at room temperature after a 2 second vortex mix.

Cells were washed on the plates two times, 1 ml/well with Optimem (Gibco-BRL). Then 0.5 mL transfection cocktail per well was applied to duplicate wells. The plates were incubated for 4 hours in 5% $CO_2$ at 37° C. After incubation cells were washed two times, 1 mL/well with cell culture media and cultured overnight. Then cells were washed twice, 1 mL/well with cysteine deficient DMEM and then incubated for 309 minutes in cysteine deficient DMEM under cell culture conditions. Cells were labelled by incubation with 250 μCi of $^{35}$S-cysteine/well in 500 μL cysteine deficient DMEM without serum for 5 hours. The cells were then washed twice, 1 mL/well with 1×phosphate buffered saline and then lysed with 100 μL SDS sample buffer (50 mM Tris-Cl [pH 6.8], 100 nM dithiothreitol, 2% sodium dodecyl sulfate, 0.1% bromophenol blue, 10% glycerol). Wells were washed with 100 μL RIPA buffer (10 mM Tris-Cl [pH 7.4], 150 mM NaCl, 1% Triton X-100, 0.1% sodium dodecyl sulfate, 0.5% sodium deoxycholate) and combined with sample buffer lysate.

E7 synthesis was evaluated by immunoprecipitation of E7 protein with goat anti-HPV-11 E7 serum and protein A sepharose beads (Sigma). Immunoprecipitated E7 protein was quantitated by SDS-PAGE and phosphoimage analysis. Total protein synthesis was evaluated by SDS-PAGE and phosphoimage analysis of a fraction of the transfected cell lysate before immunoprecipitation.

Representative experiments were performed as follows. E7 expression plasmid pcDNA11E7 (5 μg/ml) and different amounts of antisense oligonucleotide were transfected into COS-7 cells in the presence of Transfectam™ (Promega). Cells were incubated with transfection mixture for 4 hours, allowed to recover in media plus serum overnight, and labeled with $^{35}$S-cysteine for 5 hours before harvesting. Cells were lysed and E7 protein synthesis was evaluated by immunoprecipitation with αE7 serum followed by SDS-PAGE gel fractionation of protein products and phosphoimage analysis. Total protein synthesis was analyzed by SDS-PAGE separation of an aliquot of the cell extract, autoradiography and phosphoimage quantitation of all the proteins present in each lane. The following table summarizes the IC50 and IC90 values obtained with chimeric oligomers 3169-1, 3214-1, 3256-1, 3257-1 and 3336-1.

G. Demonstration of Oligomer Activity by Microinjection in VERO Cells (i) Micro injection Oligomers were microinjected together with E2 (pRc/CMV 11-E2) or E7 (pcDNAE7) expression plasmids at 50 μg/μl into the cytoplasm of VERO cells according to the following procedure. On the day preceding injection, VERO cells (approximately $2 \times 10^5$ cells/ml) were plated on coverslips. Plasmid DNA was diluted in PBS to a concentration of 20 ng/μl (E7) or 50 ng/μl (E2) in an Eppendorf tube. The tubes containing plasmid DNA were centrifuged for 15 minutes at 1,400 rpm. The tubes were set on ice prior to microinjection. A 2 μL aliquot of plasmid DNA solution was loaded onto a fem to top. The tip was set with the coverslip at 45°. The pressure on the microinjector was set at 80 and the injection was performed. The coverslips were incubated at 37° C. overnight after insertion. At 16 hours post-injection, cells were fixed and immunostained with goat anti-E7 polyclonal antibody, as explained below.

(ii) Indirect Fluorescence Immunoassay

Prior to use in this assay, goat anti-HPV-11 E7 or HPV-11 E2 serum was preabsorbed with VERO cells as follows. Confluent VERO cells from two T-150 flasks were scraped and then washed twice with PBS. 200 μl serum was then added to the cell pellet and mixed at 40° C. overnight. The

| POTENCY OF CLIGOMERS TARGETED TO HPV-11 E7 IN A CELL BASED ASSAY | | | |
|---|---|---|---|
| | | Cell-based assay | |
| Oligomer | Backbone | IC50 | IC90 |
| 3169-2 | [MP(R$_p$)/DE]-[DE]-[MP(R$_p$)/DE] | >2 μM | >>10 μM |
| 3214-1 | [MP(R$_p$)/DE]-[DE/PS]-[MP(R$_p$)/DE] | 0.2 μM | 1 μM |
| 3256-1 | [MP(R$_p$)/DE]-[PS]-[MP(R$_p$)/DE] | 0.12 μM | 1 μM |
| 3257-1 | [MP(R$_p$)/DE]-[DEIPS]-[MP(R$_p$)/DE] | 0.06 μM | <0.3 μM |
| 3336-1 | 2'OMe[MP(R$_p$)/DE]-[DE/PS]-2'OMe[MP(R$_p$)/DE] | 0.4 μM | ~2 μM |

It is clear from this example that chimeric oligonucleotides 3214-1, 3257-1 and 3256-1, which contain all phosphorothioate ([PS]) or alternating phosphorothioate/phosphodiester ([PS/DE]) linkage in the middle and chiral methylphorothioate/methylphosphonate dimers linked by phosphodiester linkages ([MP(R$_p$)/DE]) as end-blocks, are potent inhibitors of transient expression of HPV E7 protein in COS-7 cells.

Chimeric oligonucleotides with phosphodiester linkages in the middle, such as 3169-1, were not potent in the cell-based assay, although they proved to be very potent in the cell-free assay. This difference may be due to the intracellular instability of the phosphodiester linkage. Finally, oligonucleotides containing 2'OMe modification in the sugar of the nucleosides present at the ends (see 3336-1) were less potent than the corresponding chimeras with [MP(R$_p$)/DE] ends.

mixture was centrifuged and the supernatant was removed to a new tube. The preabsorbed serum was stored in 50% glycerol at −20° C.

Expression level of E2 or E7 was assessed using a fluorescent antibody assay. Coverslips were fixed in 10% formaldehyde in PBS for 20 minutes at room temperature and then washed twice with PBS, followed by incubation with goat anti-HPV-11 E7 or HPV-11 E2 protein serum preabsorbed as set forth above at a 1:1000 dilution in PBS for two hours at room temperature. The coverslips were then washed with PBS three times, five minutes per wash, and incubated with FITC-conjugated Donkey Anti-Goat IgGAb (Jackson, ImmunoResearch, Cat #705-095-147) at 1:200 dilution in PBS. The coverslips were then washed with PBS three times, air-dried, and mounted with 50% glycerol on slide glass. Examination was done under UV lights. Results are presented in the following tables.

POTENCY OF OLIGOMERS TARGETED TO HPV-11 E7

| | | | Cell-free assay | | | |
|---|---|---|---|---|---|---|
| Oligomer | Backbone | Tm | IC50 | IC90 | CAT Inhibition | Vero cells Microinjection |
| 2687-1 | [75% MP($R_p$)][DE][75% MP($R_p$)] | 52.8 | ~0.04 μM | 1 μM | 20%, 5 μM | N-3 + (0.5 μM) |
| 3169-1 | [MP($R_p$)/DE][DE]$_5$[MP($R_p$)/DE] | 62.6 | ~0.04 μM | 0.8 μM | 20%, 5 μM | C-3 + (2 μM) |
| 3214-1 | [MP($R_p$)/DE][DE/PS]$_5$[MP($R_p$)/DE] | 61.0 | ~0.2 μM | 4 μM | No inh., 10 μM; 25%, 5 μM | C-3 + (1 μM) |
| 3257-1 | [MP($R_p$)/DE][DE/PS]$_7$[MP($R_p$)/DE] | 60.9 | ~0.06 μM | 0.6 μM | 50%, 2 μM | C-3 + (0.5 μM) |
| 3256-1 | [MP($R_p$)/DE][PS]$_5$[MP($R_p$)/DE] | 60.1 | ~0.25 μM | 5 μM | No inh., 5 μM | C-3 + (0.5 μM) |
| 3336-1 | 2'OMe[MP($R_p$)/DE][PS]$_7$-2'OMe[MP($R_p$)/DE] | 66.8 | | | | N/D |
| 3341-1 | 2'OMe[MP($R_p$)/DE][PS]$_7$-2'OMe[MP($R_p$)/DE] | 65.8 | 2 μM | >>10 μM | | N/D |

POTENCY OF OLIGOMERS TARGETED TO HPV-11 E2 TN MICROINJECTION TO VERO CELLS
Microinjection Summary

| E2 OLIGOMERS | | | Oligo Concentration of Microinjection Solution | | | | | | | |
|---|---|---|---|---|---|---|---|---|---|---|
| | | | Nuclear Injection | | | | Cytoplasmic Injection | | | |
| Oligomer | Target | Backbone | 4+ | 3+ | 2+ | 1+ | 0 | 4+ | 3+ | 2+ | 1+ | 0 |
| 3233 | 11/E2,AUG/-4 | [MP($R_p$)/DE]-[DE]$_5$[MP($R_p$)/DE] | | | | | | 2 μM | 1 μM | 0.5 μM | | |
| 3234 | 11/E2,AUG/-4 | [MP($R_p$)/DE]-[PS/DE]$_5$[MP($R_p$)/DE] | | | | | | 1 μM | 0.5 μM | | | |
| 3170 | 11/E2,AUG/-12 | [MP($R_p$)/DE]-[DE]$_5$[MP($R_p$)/DE] | | | | | | 2 μM | 1 μM | 0.5 μM | | |
| 3123-1 | 11/E2,AUG/-12 | MP($R_p$)/DE | | | | | | | | | 10 μM | 2 μM |
| 3124-1 | 11/E2,AUG/-5 | MP($R_p$)/DE | | | | | | | 2 μM and 10 μM | | | |

NOTE: 3170-1 has the structure 3'-TCCTGCT(CCTTC)TACCTTCG-5' [MP($R_p$/DE][DE][MP($R_p$)/DE]

H. Demonstration of Activity of Antisense Oligomers Targeted to E2 in Cell-Free Translation Extracts E2 RNA was prepared by transcribing plasmid pRc/CMV-11E2 with T7 RNA polymerase using an Ambion MegaScript kit, following the manufacturer's directions.

In vitro transcribed E2 mRNA was cell-free translated in rabbit reticulocyte lysates (Promega). The final concentrations of each component of the assay system was as follows:

| | |
|---|---|
| In vitro transcribed uncapped RNA: | 50 nM |
| $^{35}$S-Methionine: | 1.3 μCi/μl |
| Potassium Acetate: | 20 mM |
| Amino acid mixtures, methionine deficient: | 50 μM |
| Rabbit Reticulocyte Lysate: | 33% vol/vol |
| RNAsin: | None or 0.5 units/μl |

Cell-free translation was performed at 37° C. for one hour and was stopped by addition of SDS gel loading buffer and incubation at 95° C. for 3 minutes. Translation of E2 was evaluated after separation of the translation mix by SDS-PAGE analysis, followed by phosphoimage analysis. To determine the effect of oligomers targeted to the translation initiation codon of E2, in vitro transcribed E2 mRNA was translated in the presence of 0.02 or 0.04 units/μl of RNAseH, and using oligonucleotide concentrations ranging from 0.01 to 10 μM. CAT mRNA was co-translated, or translated in independent translation reactions as control.

As shown in the following table, measurements of E2 cell-free translation inhibition and of specificity with respect to CAT control mRNA were obtained with the oligomers 3170, 3233 and 3234. Parallel studies showed that these end-blocked chimeric oligomers were more specific than all-phosphodiester oligomers.

POTENCY OF OLIGOMERS TARGETED TO HPV-11 E2 IN CELL FREE ASSAY

| | | | Cell-free assay | | |
|---|---|---|---|---|---|
| Oligomer | Target | Backbone | IC50 | IC90 | CAT-IC50 |
| 3170-1 | AUG-12 | [MP($R_p$)/DE][DE]$_5$[MP($R_p$)/DE] | ~0.06 μM | ~1 μM | 20% (5 μM) |
| 3233-1 | AUG-4 | [MP($R_p$)/DE][DE]$_5$[MP($R_p$)/DE] | ~0.1 μM | ~1 μM | 20% (5 μM) |

-continued

POTENCY OF OLIGOMERS TARGETED TO HPV-11 E2 IN CELL FREE ASSAY

|  |  |  | Cell-free assay | | |
|---|---|---|---|---|---|
| Oligomer | Target | Backbone | IC50 | IC90 | CAT-IC50 |
| 3234-1 | AUG-4 | [MP($R_p$)/DE][DE/PS]$_5$[MP($R_p$)/DE] | ~0.1 μM | ~1 μM | 15% (10 μM) |

I. Demonstration of Activity of Antisense Oligomers Targeted to E6 in Cell-Free Translation Extracts Polycistronic E6/E7 mRNA was prepared by transcribing the plasmid pRc/CMV11-E6/E7 with T7 RNA polymerase using an Ambion MegaScript kit, following the manufacturer's directions. In vitro transcribed E6/E7 mRNA (50 nM) was cell-free translated in rabbit reticulocyte lysates (Promega) as described in part D above. Cell-free translation was performed at 37° C. for one hour and was stopped by addition of SDS gel loading buffer and incubation at 95° C. for 3 minutes. Translation of E6 was evaluated after separation of the translation mix by SDS-PAGE analysis, followed by phosphoimage analysis.

To determine the effect of oligomers targeted to the translation initiation codon of E6, in vitro transcribed E6/E7 mRNA was translated in the presence or absence of the oligonucleotides shown below. Translations were performed in the presence of 0.02 or 0.04 units/μl of RNAse H, and using oligomer concentrations ranging from 0.01 to 10 μM. CAT mRNa was co-translated as control. As shown in the table below, the best results were obtained with oligomer 3215-1, a 20 mer chimeric methylphosphonate oligomer targeted to AUG-10.

Example 46

Preparation of a 2'-O-Me, GG (5'O-DMT, 3'O-βCE, $N^2$IBU) MP($R_p$) Dimer Via 5'methylphosphonamidite Monomer Into a 500 ml RBF was placed 30.5 g (0.05 M) of 2'-OMe, G(3'O-tBDPS,5'-OH, $N^2$IBU) which was rendered anhydrous with 1×100 ml pyridine and 2×100 ml acetonitrile (ACN). The resulting dry foam was released from the rotoevaporator with argon and treated with 300 ml anhydrous ACN, 10.5 ml triethylamine (0.075 M, 1.5 eq.). The flask was stoppered with a rubber septa and treated (dropwise) with 10.9 ml chloro, methyl-N,N-diisopropylaminophosphine (0.06 M, 1.2 eq.). The reaction was allowed to stir overnight at room temperature.

The next morning, the reaction was found to contain no starting material, as determined by HPLC (Beckman Gold, RP, Waters C18 bondapak; λ254 nm, 20 min. program 50/50 ACN/0.1 M TEAA to 100% ACN.). The reaction mix was concentrated then purified on 225 g silica in 3:1 ethyl acetate/heptane containing 2% TEA. Product was pooled and concentrated to obtain 25 g (67%) of solid foam that was 86% pure by HPLC. This product was taken up in ACN to

|  |  |  | Cell-free assay | | |
|---|---|---|---|---|---|
| Oligomer | Target | Backbone | IC50 | IC90 | CAT inhibition |
| 3255-1 | AUG-10 | [MP($R_p$)/DE][DE][MP($R_p$)/DE] | 1 μM | 5 μM | No inh. (10 μM) |
| 3215-1 | AUG-10 | [MP($R_p$)/DE][PS/DE][MP($R_p$)/DE] | 0.3 μM | 2 μM | no inh. (10 μM) |

Compounds 3255 and 3215 are as follows:
3255-1: 3'-CTGCTCC(GTAAT)ACCTTTCA-5'
3215-1: 3'-CTGCTCC(GTAAT)ACCTTTCA-5'

Following are a set of examples relating to certain chemistry useful in the synthesis of chirally pure 2'-O-Me dimers. The preparation of two dimers are discussed in Examples 46 and 47 to further illustrate the utility of the P(III) coupling chemistry through either a 5' or 3' phosphoramidite monomer. These two examples also demonstrate the ability to oxidize (with retention) internucleoside methylphosphoramidite linkages using either cumene hydroperoxide or camphorsulfonyl oxaziridine to yield the desired methylphosphonate linkage. Although either or both reagents may be used, our preference is to use camphorsulfonyl oxaziridine because it does not have the hazards associated with cumene hydroperoxide. Example 48 describes the synthesis of a 2'-O-Me-guanosine 5'-OH, and is a general scheme applicable to the preparation of other 5'-OH nucleosides. Example 49 describes the phosphitylation of a 2'-O-Me UC dimer with β-cyanoethyl ("CE") phosphoramidite.

give a 10% solution of the desired amidite, which was stored over molecular sieves.

Into a 500 ml flamed dried RBF with argon balloon overhead, was transferred via an addition funnel with glass wool, 100 ml (10 g, 0.013 M, 1.25 eq.) of stock solution of 2'O-Me G(5'-amidite, 3'-tBDPS, $N^2$IBU) along with 71.1 ml (7.1 g, 0.011 M, 1.0 eq.) of stock solution of 2'O-Me, G(5'DMT,3'OH,$N^2$IBU). The reaction mixture was then treated all at once with 30.9 ml (25% by weight sol. in ACN, 5.0 eq.) of ethylthio-tetrazole (ETT) and stirred at room temperature for 5 minutes, after which time cumene hydroperoxide (2.1 ml, tech., 80%) was added all at once. The reaction was quenched 5 minutes later with 20 ml saturated sodium bisulfite. The reaction mixture was analyzed by HPLC and determined to be 86% dimer with a ratio of 1.2/1.0 ($S_p/R_p$). The reaction mixture was then placed on a roto-evaporator and the ACN was removed. The resulting concentrate was then taken up in 150 ml dichloromethane (DCM), and washed using 2×75 ml sat. NaHCO$_3$ and 1×75 ml water. The aqueous washes were combined and then extracted with 1×75 ml DCM and combined with the original organic phase and dried over NaSO$_4$, filtered and concentrated to a light amber solid foam.

The solid foam, 12.6 g (0.0094 M, 1.0 eq.) of 2'-O-Me, GG(5'DMT, 3'tBDPS, N$^2$-iBu) MP(R$_p$/S$_p$) product was taken up in 120 ml of THF and treated all at once with 14.2 ml TBAF (1 M in THF, 0.014 M, 1.5 eq.) and allowed to stand at room temperature overnight. The next morning desilylation was determined to be complete by HPLC with a purity of 84% (44% S$_p$ and 40% R$_p$). A small amount of silica gel was added to the reaction mixture and after stirring for 10 min. the reaction mix was passed through a glass sintered funnel containing a small bed of silica gel. The product was eluted off the bed with 500 ml 10% methanol in DCM. The filtrate was concentrated, taken up in DCM and washed using 2×75 ml sat. NaHCO$_3$ and 1×75 ml brine. The organic layer was dried over MgSO$_4$, filtered and concentrated to a thick oil, which weighed 14 g but had a strong cumene hydroperoxide odor.

The oil was taken up in ACN to give a 23% by weight solution and purified on a 2 inch preparative HPLC column (Beckman Gold, RP, Kromasil C18, 10 u, λ295 nm, 60 ml/min., isocratic 45% ACN and 55% H20). Three separate runs were made and the pure R$_p$ fractions were pooled and concentrated to yield 3.3 g of 100% pure GG(3'-OH) MP(R$_p$) dimer.

Example 47

Preparation of 2'-O-Me, CU(5'-DMT, 3'-OH, N$^4$IBU) MP(R$_p$) Dimer Via a 3'-methylphophonamidite Monomer 50 g (0.082 M, 1.0 eq.) of the 2'-O-Me, DMT protected cytidine was rendered anhydrous with 3×100 ml pyridine and 1×100 ml ACN co-evaporations. The flask was released with argon and to it was added a stir bar, 500 ml ACN, 22.7 ml TEA (0.163 M, 2 eq.) and a septa with an argon ballon overhead. The solution was treated dropwise with 19.2 ml (0.11 M, 1.3 eq.) of Cl-MAP via a 20 ml plastic syringe and stirred overnight at room temperature. The reaction was checked the next morning on HPLC and starting material was gone. The reaction mixture was concentrated and purified on 300 g silica gel with 50/50, EtOAc/Heptane, with 2% TEA. Four liters of the eluent was passed through the column and all U.V. positive material was pooled and concentrated to a solid foam (52 g, 95% purity (HPLC), 84% recovery). The product was taken up in ACN to give a 10% solution by weight of the desired 3'-methylphosphonamidite and to this solution was added molecular sieves.

After sitting over molecular sieves for one night, 100 ml (10 g, 0.013 M, 1.25 eq.) of this stock solution was added to a flame dried 500 ml RBF along with 51 ml of a stock solution of U, 5'OH (5.1 g, 0.01 M, 1.0 eq.). The ETT (67 ml, 10% solution in ACN over molecular sieves, 6.7 g, 0.052 M, 5.0 eq.) was added all at once via an addition funnel and the reaction was stirred for 5 minutes at room temperature. The phosphite intermediate was then oxidized with 36 ml camphorsulfonyl oxaziridine (CSO) solution (10% in ACN over molecular sieves) for 5 minutes. The reaction mixture was checked by HPLC and found to contain 79% dimer with a ratio of 1.2/1.0 (S$_p$/R$_p$). The reaction mix was concentrated to a solid foam, taken up in 150 ml DCM and worked up as described above in Example 46. The resulting solid foam was 89% dimer by HPLC and was desilylated (see below) without further purification.

The solid foam, 2'-O-Me, CU(5'-ODMT, 3'-OtBDPS, N$^4$IBU), MP (S$_p$/R$_p$) dimer, was taken up in 100 ml THF then treated all at once with 12.3 ml tetrabutyl ammonium fluoride (1 M in THF, 0.012 M, 1.5 eq.). The reaction was checked 1 hr. later by HPLC and determined to be complete by the disappearance of starting material. The reaction mix was concentrated and purified on silica gel (10:1) with 3:1 EtOAc:DCM with 10% methanol. The purified dimer (8 g, 1.5/1.0, S$_p$/R$_p$) was then purified by preparative HPLC, which following two separate runs produced 3.3 g of pure R$_p$ dimer, 3'-OH.

Example 48

Preparation of 2'-OMe, G(5'-OH, 3'-OtBDPS, N$^2$IBU) Via the DMT Protected 3'-OH 25 g of DMT protected 2'-O-Me guanosine was rendered anhydrous with 3×100 ml DMF co-evaporations. The solid foam was released from the roto-evaporator via argon and dissolved in 250 ml anhydrous DMF. The solution was then treated with 15.3 g t-butyldiphenylsilyl chloride (0.056 M, 1.5 eq.) and 10.1 g imidazole (0.15 M, 4.0 eq.), then stirred manually until the solution was homogeneous and allowed to let stand overnight at room temperature. The reaction was checked by HPLC the next morning and found to contain no starting material. The reaction mix was then poured into 300 ml ice water while manually stirring. The solids were collected in a Buchner funnel and rinsed with cold water and then dissolved in 250 ml DCM and washed using 3×200 ml sat. NaHCO$_3$, 1×100 ml water. The combined aqueous phases were extracted with 2×100 ml DCM. The organic phases were combined and dried over NaSO$_4$, filtered and concentrated to a solid foam, obtaining 35 g of newly silylated product (slightly more than the theoretical yield).

The solid foam, 2'-O-Me, G(5'-ODMT, 3'-OtBDPS, N$^2$IBU) was dissolved in 150 ml DCM and with magnetic stirring was treated all at once with 260 ml benzene sulfonic acid (0.1 M solution in 75/25 DCM/MeOH, 0.026 M, 0.67 eq.). Reaction proceeded for 10 minutes after which time a TLC in 5% MeOH in DCM revealed that complete desilylation had occurred. The reaction was immediately quenched with 20 ml TEA at which time the solution changed from a deep clear amber color to a light clear yellow color. The solution was concentrated to a thick oil and then loaded onto 250 g silica gel equilibrated in 0.5% MeOH in DCM. The free trityl was removed with the same eluent and the product was then removed with 6% MeOH in DCM. The fractions containing product were pooled and concentrated to obtain 21.8 g (98.5% pure by HPLC, 91% yield overall) of the titled compound.

Example 49

Preparation of 2'-O-Me UC(5'-ODMT, N$^4$IBU)-3'CE Phosphoramidite Via UC, 3'-OH 980 mg 2'-O-Me UC (5'DMT, 3'OH, N$^4$IBU) MP(R$_p$) dimer was rendered anhydrous with 3×10 ml ACN co-evaporations. The resulting dry foam was then taken up in 10 ml anhydrous ACN and to it was added 325 µl TEA (2.32 mmol, 2.25 eq.), followed by dropwise addition (via a 1 ml glass syringe) of 460 µl 2'-cyanoethyl-N,N-diisopropyl chlorophosphoramidite (2.06 mmol, 2.0 eq.). The reaction was allowed to stir overnight, after which time a TLC and HPLC showed the reaction to be complete. The reaction mix was concentrated and loaded onto a 1.5×20 cm column containing 30 g of silica equilibrated in 3:1:1, EtOAc: DCM:ACN, with 1% TEA. The product was eluted in the same and the fractions with pure product were pooled and concentrated to yield 600 mg of pure amidite.

Example 50

Effect of Position of an RNA-Chimera Base Mismatch on Cleavage Rate

The present example demonstrates the influence of the position of a base mismatch in an RNA-chimeric oligonucleoside duplex on the rate of RNaseH cleavage of the target RNA. Both E. coli and mammalian HeLa RNaseH enzymes were studied. Two separate studies were done using two different sets of RNA-chimeric oligonucleoside duplexes ("Set 1" and "Set 2").

a. Set 1 Study

Two chimeric oligomers (3256 and 3510) were prepared having base sequences differing from one another in one position. In these sequences, the nucleosides in parentheses contain phosphorothioate linkages on their 5'-side:

3256:
3'-C C T G T T G (T A C G T) A C C T T C T G-5'
(SEQ ID NO:6)

3510:
3'-C C T G T T G (T A T G T)A C C T T C T G-5'
(SEQ ID NO: __)
    [Mp(R$_p$)/DE]   [PS]   [Mp(R$_p$)/DE]

The following RNAs were prepared to study the effect on cleavage rate of mismatches at various duplex positions (the position of the mismatch with chimeric sequence 3256 is bolded and underlined, and the numbering of the internucleotide linkages appears in subscript):

2577 (perfect match with 3256; one mismatch with 3510):
5'-G G A C A$_5$A C A U G$_{10}$ C A U G G$_{15}$ A A G A C-3'
(SEQ ID NO:27)

3656 (one mismatch with 3256):
5'-G G A C A$_5$ A C U U G$_{10}$ C A U G G$_{15}$ A A G A C-3'
(SEQ ID NO: __)

3657 (one mismatch with 3256):
5'-G G A C A$_5$ A C A C G$_{10}$ C A U G G$_{15}$ A A G A C-3'
(SEQ ID NO: __)

3545 (one mismatch with 3256):
5'-G G A C A$_5$ A C A G G$_{10}$ C A U G G$_{15}$ A A G A C-3'
(SEQ D NO: __)

3316 (perfect match with 3510; one mismatch with 3256):
5'-G G A C A$_5$ A C A U A C A U G G$_{15}$ A A G A C-3'
(SEQ ID NO: __)

3548 (one mismatch with 3256):
5'-G G A C A$_5$ A C A U G$_{10}$ A A U G G$_{15}$ A A G A C-3'
(SEQ ID NO: __)

3547 (one mismatch with 3256):
5'-G G A C A$_5$ A C A U G$_{10}$ U A U G G$_{15}$ A A G A C-3'
(SEQ ID NO: __)

3991 (one mismatch with 3256):
5'-G G A C A$_5$ A C A U G$_{10}$ G A U G G$_{15}$ A A G A C-3'
(SEQ ID NO: __)

3646 (one mismatch with 3256):
5'-G G A C A$_5$ A C A U G$_{10}$ C G U G G$_{15}$ A A G A C-3'
(SEQ ID NO: __)

3658 (one mismatch with 3256):
5'-G G A C A$_5$ A C A U G$_{10}$ C U U G G$_{15}$ A A G A C-3'
(SEQ ID NO: __)

3659 (one mismatch with 3256):
5'-G G A C A$_5$ A C A U G$_{10}$ C A C G G$_{15}$ A A G A C-3'
(SEQ ID NO: __)

Each of the above chimeric oligonucleosides was prepared generally according to the method described in Example 30. The complementary (perfect matched and single mismatched) RNA target sequences were prepared generally according to the method given in Example 28.

A $^{32}$P-label was coupled to the 5'-end of these RNA oligomers using [γ-$^{32}$P]-ATP and T4 polynucleotide kinase according to standard procedures (Sambrook, Fritsch & Maniatis, "Molecular Cloning—A Laboratory Manual [2nd ed.]" Book 2, pp. 11.31–11.39 [Cold Spring Harbor Laboratory Press, 1989]).

RNaseH from bacterial E. coli was purchased from Promega Corp. (Madison, Wis.). The source of mammalian RNaseH was a HeLa nuclear extract purchased from Promega Corp. (Madison, Wis.). Buffer A, used for RNaseH reactions, contained 20 mM KCl, 9 mM MgCl$_2$, 1 mM 2-mercaptoethanol, 250 µg/ml BSA (Promega Corp.) and 100 u/ml RNasin (Promega Corp.). E. coli RNaseH was prepared as a 2 nM stock solution in Buffer A and concentrated HeLa nuclear extract was diluted 10 times with Buffer A. Both diluted RNaseH stock solutions were kept not more than 1 day at 0° C. and were warmed to 37° C. for 30 minutes before use.

A mixture of 5'-$^{32}$P-labeled RNA oligomer (approximately 80,000–100,000 dpm, 5×10$^{-10}$ M) was mixed with a mole equivalent of the appropriate chimeric oligomer in Buffer A (total volume 98 µl). This mixture was incubated at 37° C. for 1 hour. Next, an RNaseH solution (1.1 µl) was added and the resulting mixture incubated at 37° C. Aliquots (15 µl) were removed at specified times, diluted with EDTA (0.5 M, 2 µl) then frozen on dry ice and kept at −78° C. The products of RNA cleavage were analyzed by gel electrophoresis using a 15% polyacrylamide/7 M urea gel (20×30 cm×0.5 mm i.d.) equilibrated in 1×TBE buffer (pH 8.1). The gel was electrophoresed at 1200 volts for 2–3 hours. Bands on the wet gel were visualized by phosphorimage analysis using a Bio-Rad Model GS-250 Molecular Imager (Calabasas, Calif.).

Site-specific RNaseH mediated cleavage was observed for both perfect matched complexes and for most single mismatched complexes studied (see tables below). The length of the fragments (and, consequently, the positions of RNA cleavage) were determined according to their electrophoretic mobilities. Using this analysis, it was shown that in all cases the cleavage was limited to phosphodiester bonds near or within the RNA central region (CR) complementary to the negatively charged phosphorothioate segment of the chimeric oligomer.

In this series of experiments, the E. coli RNaseH cleavage occurred near the 3'-end of the CR of RNA at positions of phosphodiester bonds 12, 13 and 14, while the HeLa RNaseH cleavage pattern was shifted by 2 base pairs toward the inside of the CR block in the direction of the 5'-end of the RNA (phosphodiester bonds 10, 11 and 12, see the following table). For the perfectly matched complexes, the preferred sites of cleavage were RNA phosphodiester bond 13 for the E. coli enzyme and phosphodiester bond 11 for the HeLa enzyme. The sites of RNA cleavage were almost identical in all complexes studied; however, the initial rates of cleavage at specific sites and the overall cleavage rate changed drastically depending upon the position of the mismatch.

In complexes containing a mismatch near the preferred RNA cleavage site (as defined by the perfect matched complex), the overall cleavage rate of RNA typically decreased dramatically (10–100 times) as compared to that for the perfect matched complex. This differential cleavage rate was most pronounced when the mismatch was positioned at the first or second base pair immediately 5' to the preferred (perfect matched) phosphodiester cleavage site in the RNA. Similar decreases in cleavage rate were observed for mismatches in other positions. In the case of the mammalian HeLa enzyme, a mismatch at the first base pair immediately 5' to the preferred RNA cleavage site (i.e., at RNA nucleotide position 11) led to a particularly significant differential effect in the cleavage rate. This effect was observed with every base mismatch combination tested. In addition to the high mismatch effect observed in the first and second base pairs on the 5'-side of the preferred RNA cleavage site, a mismatch at the first base pair immediately 3' to the preferred RNA cleavage site for the mammalian enzyme (i.e., at RNA nucleotide position 12) led to significant (~10-fold) reduction in the HeLa cleavage rate for one mismatch tested (rG-dT, see complex 3646-3256) and to no effect with a different mismatch at this position (rU-dT, see complex 3658-3256). Decrease, if any, of the rate of RNA cleavage due to mismatches in other positions was typically less significant (1–3 times).

The materials, chemicals and RNaseH assay procedure employed for Set 2 were essentially the same as described in Example 50(a).

Site-specific RNaseH mediated cleavage was observed for the perfect matched complex and for both single mismatched complexes studied (see table below). The length of the fragments (and, consequently, the positions of RNA cleavage) were determined according to their electrophoretic mobilities. In agreement with Example 50(a), it was shown that in all cases the cleavage was limited to phosphodiester bonds near or within the RNA central region (CR) complementary to the negatively charged phosphorothioate segment of the chimeric oligomer.

Set 1: Initial RNA Cleavage Sites and Rates for *E. coli* and HeLa RNaseH Cleavage

| RNA # | Oligomer # | Mismatch type | position* | *E. coli* site** | rate*** | HeLa site | rate |
|---|---|---|---|---|---|---|---|
| 2577 | 3256 | perfect | — | 13 > 12 >> 14 | f | 11 >10 >12 | f |
| 3316 | 3510 | perfect | — | 13 > 12 >> 14 | f | 11~12 >10 | f |
| 3656 | 3256 | rU-dT | 8 | 13 > 12 >> 14 | f | 11 > 12 > 10 | f |
| 3657 | 3256 | rC-dA | 9 | 13 > 12 >> 14 | f | 11 > 12 > 10 | f |
| 3545 | 3256 | rG-dA | 9 | 13 > 12 >> 14 | f | 11 > 12 > 10 | m |
| 3316 | 3256 | rA-dC | 10 | 13 > 12 >> 14 | f | 12 > 11 > 10 | s |
| 2577 | 3510 | rG-dT | 10 | 13~12 >> 14 | f | 12~13~14 | vs |
| 3548 | 3256 | rA-dG | 11 | 13 >> 14 >> 12 | m | 11 > 10~12 | vs |
| 3547 | 3256 | rU-dG | 11 | 13 >> 14 >> 12 | m | 10 > 11 > 12 | vs |
| 3991 | 3256 | rG-dG | 11 | 13 >> 14 >> 12 | m | 10~11~12 | vs |
| 3646 | 3256 | rG-dT | 12 | 12 >> 13 >> 14 | s | 10 >> 11 > 12 | s |
| 3658 | 3256 | rU-dT | 12 | 12~13~14 | vs | 12 >> 11 > 10 | f |
| 3659 | 3256 | rC-dA | 13 | 12 >> 13 >> 14 | s | 11~10> 12 | f |

*Nucleotide position of mismatched base pair (as numbered from the 5'-end of the RNA).
**Positions of the most cleavable phosphodiester bonds of RNA (as numbered from the 5'-end of the RNA; thus, there are 19 total phosphodiester bonds in these 20-mer RNA targets).
***Relative overall RNA cleavage rates: fast (f):moderate (m):slow (s):very slow (vs) ~ 100:30:10:2.

b. Set 2 Study

Using techniques described above, three different chimeric oligomer sequences (3262, 3639 and 3640) were prepared as follows (the nucleosides in parentheses contain phosphorothioate linkages on their 5'-side, and the position of the mismatch with RNA sequence 3468 [described below] is bolded and underlined):

In this series of experiments, the *E. coli*. RNaseH cleavage occurred near the 3'-end of the CR of the target RNA at positions of phosphodiester bonds 16, 17, and 18, while the HeLa RNaseH cleavage pattern was shifted by 2 base pairs in the 5'-direction toward the inside of the CR block (phosphodiester bonds 14, 15 and 16, see the following table). For the perfect matched complex the most preferable

```
3262 (perfect match with 3468):
3'-C T C T T C T T C T A (G T G A C) C T A T A T G G-5'  (SEQ ID NO: 8)

3639:
3'-C T C T T C T T C T A (G T G G C) C T A T A T G G-5'  (SEQ ID NO: __)

3640:
3'-C T C T T C T T C T A (G T G A A) C T A T A T G G-5'  (SEQ ID NO: __)

[Mp(Rp)/DE]            [PS]         [Mp(Rp)/DE]
```

The following RNA was prepared using techniques described above to study the effect on cleavage rate of mismatches at two different duplex positions:

positions of cleavage were phosphodiester bonds 17 and 16 for *E. coli* and HeLa enzymes respectively. Again, the sites of RNA cleavage were almost identical in all complexes

```
3468 RNA:
5'-G A G A A₅G A A G A₁₀U C A C U₁₅G G A U A₂₀ U A C C-3'   (SEQ ID NO: __)
``` studied, however the initial rates of cleavage changed drastically depending upon the presence and position of the mismatch. While a moderate decrease in overall RNA cleavage rate was found using E. coli enzyme (see, for example, complex 3468–3640, containing a mismatch situated at the second base pair to the 5'-side of the most preferable RNA cleavage site), for HeLa enzyme using the same complex the overall RNA cleavage rate decreased dramatically (~50 times) as compared to the perfect matched complex. The results with the HeLa enzyme also confirmed the finding, noted in Example 50(a) above in respect to Set 1, that a mismatch positioned at the base pair immediately 5' to the preferred (perfect matched) RNA cleavage site leads to a particularly significant differential cleavage rate (approx. 50-fold reduction).

Set 2: Initial RNA Cleavage Sites and Rates for *E. coli* and HeLa RNaseH Cleavage

| RNA # | Oligomer # | Mismatch type | position* | E. coli site** | rate*** | HeLa site | rate |
|---|---|---|---|---|---|---|---|
| 3468 | 3262 | perfect | — | 17 > 18 > 16 | f | 16 >15 >14 | f |
| 3468 | 3639 | rU-dG | 15 | 18 > 17 > 16 | m | n.d. | n.d. |
| 3468 | 3640 | rG-dA | 16 | 18 > 16 >> 17 | m | 14 > 15 > 16 | vs |

*Nucleotide position of mismatched base pair (as numbered from the 5'-end of the RNA).
**Positions of the most cleavable phosphodiester bonds of RNA (as numbered from the 5'-end of RNA; there are 23 total DE bonds in the 24-mer 3468 RNA target).
***Relative overall RNA cleavage rates: fast (f):moderate (m):slow (s):very slow (vs) ~ 100:30:10:2.

Pharmaceutical compositions utilizing the compounds of the present invention, and methods of formulating the same, are known in the art, and appropriate composition and formulation techniques are further described in U.S. patent application Ser. Nos. 08/154,013 and 08/154,014. Likewise, applicable methods of using the present compounds and compositions, for example in mammalian disease treatment, are disclosed in those applications, which are incorporated herein by reference.

While the foregoing examples and description set forth the preferred embodiments and various ways of accomplishing the present invention, they are not intended to be limiting as to the scope of the invention, which is as set forth in the following claims. Moreover, it will be recognized in view of the foregoing disclosure that the invention embraces alternative embodiments and structures that are the lawful equivalents of those described herein.

What is claimed is:

1. An oligonucleoside compound for effecting RNaseH-mediated cleavage of a target ribonucleic acid sequence, comprising an RNaseH-activating region and a non-RNaseH-activating region, wherein
the RNaseH-activating region comprises a segment of at least three consecutive 2'-unsubstituted nucleosides linked by charged internucleoside linkage structures,
the non-RNaseH-activating region comprises a segment of at least two linked nucleosides, at least one linkage in said non-RNaseH-activating region being chirally-selected,
and wherein the base sequence of the oligonucleoside compound is complementary to a target region of the target ribonucleic acid sequence.

2. The oligonucleoside compound of claim 1 wherein said RHaseH-activating region comprises between five and about nine consecutive linked nucleosides.

3. The oligonucleoside compound of claim 2 wherein the charged linkage structures in said RNaseH-activating region are selected from the group consisting of phosphodiester linkages, phosphorodithioate linkages and phosphorothioate linkages.

4. The oligonucleoside compound of claim 3 wherein said RNaseH-activating region comprises a plurality of phosphorothioate linkages.

5. The oligonucleoside compound of claim 2 wherein said chirally selected linkage in the non-RNase-activating region comprises at least four linked nucleosides, and further comprises a plurality of $R_p$-selected linkage structures.

6. The oligonucleoside compound of claim 5 wherein the segment of chirally-selected linkage structures in said non-RNaseH-activating region comprises a mixed chiral linkage sequence including at least two different linkage structures, at least one of which is asymmetric.

7. The oligonucleoside compound of claim 6 wherein said different linkage structures in the mixed chiral linkage sequence are selected from the group consisting of:

$R_p$-methylphosphonate and phosphodiester linkages;

$R_p$-methylphosphonate and racemic methylphosphonate linkages;

$R_p$-methylphosphonate and phosphorothioate linkages;

$R_p$-methylphosphonate and phosphorodithioate linkages; and $R_p$-methylphosphonate and alkylphosphonothioate linkages.

8. The oligonucleoside compound of claim 6 wherein said different linkage structures in the mixed chiral linkage sequence are selected from the group consisting of

```
            MP(R)/DE
            2'OMeMP(R)/2'OMeDE
            MP(R)/2OMeMP
            MP(R) enriched
            2'OMeMP(R) enriched
            MP(R)/PS
            2'OMeMP(R)/2'OMePS
            MP(R)/PS2
            2'OMeMP(R)/2'OMePS2
            2'OMeMP/2'OMeDE
            MP/2'OMeDE
            MP(R)/PAm
            2'OMeMP(R)/2'OMePAm
            2'OMeMP/2'OMePAm
            MP/2'OMePAm
            MP(R)/TE
            2'OMeMP(R)/2'OMeTE
            2'OMeMP/2'OMeTE
            MP/2'OMeTE
            MP(R)/MPS
            2'OMeMP(R)/2'OMeMPS
            2'OMeMP/2'OMeMPS
            MP/2'OMeMPS
            MP(R)/PF
            2'OMeMP(R)/2'OMePF
            2'OMeMP/2 OMePF
            MP/2'OMePF
            MP(R)/PBH₃
            2'OMeMP(R)/2'OMePBH₃
            2'OMeMP/2'OMePBH₃
            MP/2'OMePBH₃
            MP(R)/RSi
            2'OMeMP(R)/2'OMeRSi
            2'OMeMP/2'OMeRSi
            MP/2'OMeRSi
            MP(R)/CH₂
            2'OMeMP(R)/2'OMeCH₂
            2'OMeMP/2'OMeCH₂
            and MP/2'OMeCH₂,
``` or from the foregoing mixed linkage structure combinations wherein at least one MP or MP(R) linkage structure therein is replaced, respectively, with an MPS or MPS(R) linkage structure, an AAP or AAP(R) linkage structure, or an AAPS or AAPS(R) linkage structure.

9. The oligonucleoside compound of claim 6 wherein one or both of the nucleosides linked by said different linkage structures in the mixed chiral linkage sequence are 2'-substituted nucleosides.

10. The oligonucleoside compound of claim 9 wherein said 2'-substituents are selected from the group consisting of alkoxy, allyloxy and halo substituents.

11. The oligonucleoside compound of claim 1 wherein said RNaseH-activating region is at one terminal portion of the compound and said non-RNaseH-activating region is at the other terminal portion of the compound.

12. The oligonucleoside compound of claim 1 comprising a second non-RNaseH-activating region, and wherein said RNaseH-activating region is flanked in the compound by the first and second non-RNaseH-activating regions.

13. The oligonucleoside compound of claim 1 wherein said target ribonucleic acid sequence is associated with a disease condition in a subject animal, and wherein the target ribonucleic acid sequence contains an RNA target base different from an RNA non-target base occurring in the corresponding position of a non-target ribonucleic acid sequence of the subject animal, the oligonucleoside compound further comprising a targeting oligonucleoside base positioned in the RNaseH-activating region of the compound, or at the first nucleoside outside the 5'-end of the RNaseH-activating region, such that the targeting oligonucleoside base is complementary to the RNA target base upon hybridization of the compound to the target ribonucleic acid sequence.

14. The oligonucleoside compound of claim 13 wherein said RNaseH-activating region contains from 3 to about 6 deoxynucleosides.

15. The oligonucleoside compound of claim 13 wherein said targeting oligonucleoside base is positioned at the first, second or third nucleoside from the 5'-end of the RNaseH-activating region.

16. The oligonucleoside compound of claim 13 wherein the charged linkage structures in said RNaseH-activating region are selected from the group consisting of phosphodiester linkages, phosphorodithioate linkages and phosphorothioate linkages.

17. The oligonucleoside compound of claim 16 wherein said RNaseH-activating region comprises a plurality of phosphorothioate linkages.

18. The oligonucleoside compound of claim 14 wherein said segment chirally selected linkage in the non-RNase-activating region comprises at least four linked nucleosides, and further comprises a plurality of $R_p$-selected linkage structures.

19. The oligonucleoside compound of claim 18 wherein the segment of chirally-selected linkage structures in said non-RNaseH-activating region comprises a mixed chiral linkage sequence including at least two different linkage structures, at least one of which is asymmetric.

20. The oligonucleoside compound of claim 19 wherein one or both of the nucleosides linked by said different linkage structures in the mixed chiral linkage sequence are 2'-substituted nucleosides.

21. The oligonucleoside compound of claim 20 wherein said 2'-substituents are selected from the group consisting of alkoxy, allyloxy and halo substituents.

22. The oligonucleoside compound of claim 13 wherein said RNaseH-activating region is at one terminal portion of the compound and said non-RNaseH-activating region is at the other terminal portion of the compound.

23. The oligonucleoside compound of claim 13 wherein a second non-RNaseH-activating region, and wherein said RNaseH-activating region is flanked in the compond by the first and second non-RNaseH-activating regions.

24. An oligonucleoside compound for effecting RNaseH-mediated cleavage of a target ribonucleic acid sequence, wherein said target ribonucleic acid sequence is associated with a disease condition in a subject animal, and wherein the target ribonucleic acid sequence contains an RNA target base different from an RNA non-target base occurring in the corresponding position of a non-target ribonucleic acid sequence of the subject animal, said oligonucleoside compound comprising a base sequence complementary to a target region of the target ribonucleic acid sequence containing said RNA target base, an RNaseH-activating region comprising a segment of from 3 to about 6 consecutive 2'-unsubstituted nucleosides linked by charged internucleoside linkage structures, including a targeting oligonucleoside base positioned at the first, second or third nucleoside from the 5'-end of the RNaseH-activating region, such that the targeting oligonucleoside base is complementary to the RNA target base upon hybridization of the compound to the target ribonucleic acid sequence, and a non-RNaseH-activating region comprising a segment of at least two linked nucleosides, at least one of the linkages in said non-RNaseH-activating region being chirally selected.

25. The oligonucleoside compound of claim 24 wherein the charged linkage structures in said RNaseH-activating region are selected from the group consisting of phosphodiester linkages, phosphorodithioate linkages and phosphorothioate linkages.

26. The oligonucleoside compound of claim 25 wherein said RNaseH-activating region comprises a plurality of phosphorothioate linkages.

27. The oligonucleoside compound of claim 24 wherein said segment of linked nucleosides in the non-RNase-activating region comprises at least four linked nucleosides.

28. The oligonucleoside compound of claim 27 wherein said segment of linked nucleosides in the non-RNase-activating region further comprises a plurality of $R_p$-selected linkage structures.

29. The oligonucleoside compound of claim 28 wherein the segment of chirally-selected linkage structures in said non-RNaseH-activating region comprises a mixed chiral linkage sequence including at least two different linkage structures, at least one of which is asymmetric.

30. The oligonucleoside compound of claim 29 wherein said different linkage structures in the mixed chiral linkage sequence are selected from the group consisting of:

$R_p$-methylphosphonate and phosphodiester linkages;

$R_p$-methylphosphonate and racemic methylphosphonate linkages;

$R_p$-methylphosphonate and phosphorothioate linkages;

$R_p$-methylphosphonate and phosphorodithioate linkages; and $R_p$-methylphosphonate and alkylphosphonothioate linkages.

31. The oligonucleoside compound of claim 29 wherein said different linkage structures in the mixed chiral linkage sequence are selected from the group consisting of MP(R)/DE
2'OMeMP(R)/2'OMeDE
MP(R)/2'OMeMP
MP(R) enriched
2'OMeMP (R) enriched
MP(R)/PS
2'OMeMP(R)/2'OMePS
MP(R)/PS2
2'OMeMP(R)/2'OMePS2
2'OMeMP/2'OMeDE
MP/2'OMeDE
MP(R)/PAm
2'OMeMP(R)/2'OMePAm
2'OMeMP/2'OMePAm
MP/2'OMePAm
MP(R)/TE
2'OMeMP(R)/2'OMeTE
2'OMeMP/2'OMeTE
MP/2'OMeTE
MP(R)/MPS -continued 2'OMeMP(R)/2'OMeMPS
2'OMeMP/2 OMeMPS
MP/2'OMeMPS
MP(R)/PF
2'OMeMP(R)/2'OMePF
2'OMeMP/2'OMePF
MP/2'OMePF
MP(R)/PBH$_3$
2'OMeMP(R)/2'OMePBH$_3$
2'OMeMP/2'OMePBH$_3$
MP/2'OMePBH$_3$
MP(R)/RSi
2'OMeMP(R)/2'OMeRSi
2'OMeMP/2'OMeRSi
MP/2'OMeRSi
MP(R)/CH$_2$
2'OMeMP(R)/2'OMeCH$_2$
2'OMeMP/2'OMeCH$_2$
and MP/2'OMeCH$_2$ or from the foregoing mixed linkage structure combinations wherein at least one MP or MP (R) linkage structure therein is replaced, respectively, with an MPS or MPS (R) linkage structure, an AAP or AAP (R) linkage structure, or an AAPS or AAPS (R) linkage structure.

32. The oligonucleoside compound of claim 24 wherein one or more of the nucleosides in said non-RNaseH-activating region are 2'-substituted nucleosides.

33. The oligonucleoside compound of claim 32 wherein one or more of the nucleosides in said non-RNaseH-activating region are 2'-substituted nucleosides.

34. The oligonucleoside compound of claim 32 wherein said 2'-substituents are selected from the group consisting of alkoxy, allyloxy and halo substituents.

35. The oligonucleoside compound of claim 26 wherein said RNaseH-activating region is at one terminal portion of the compound and said non-RNaseH-activating region is at the other terminal portion of the compound.

36. The oligonucleoside compound of claim 26 comprising a second non-RNaseH-activating region, and wherein said RNaseH-activating region is flanked in the compound by the first and second non-RNaseH-activating regions.

37. A pharmaceutical composition comprising an effective amount of an oligonucleoside compound of claim 13 and a pharmaceutically acceptable carrier.

38. A pharmaceutical composition comprising an effective amount of an oligonucleoside compound of claim 29 and a pharmaceutically acceptable carrier.

* * * * *

UNITED STATES PATENT AND TRADEMARK OFFICE
CERTIFICATE OF CORRECTION

PATENT NO.    : 6,060,456
DATED         : May 9, 2000
INVENTOR(S)   : Arnold, Jr. et al.

It is certified that error appears in the above-identified patent and that said Letters Patent is hereby corrected as shown below:

<u>Column 112,</u>
Line 17, "segment chirally selected linkage" should read -- chirally selected linkage segment --
Line 37, "...claim 13 wherein..." should read -- ...claim 13 comprising... --

Signed and Sealed this

Twenty-second Day of October, 2002

*Attest:*

*Attesting Officer*

JAMES E. ROGAN
*Director of the United States Patent and Trademark Office*

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (ii) MOLECULE TYPE: other nucleic acid (iii) HYPOTHETICAL: no (iv) ANTI-SENSE: yes (ix) FEATURE:
       (A) NAME/KEY: CT oligomers 2286-1, 2288-1, 2287-1,
          2781-1, 2782-1, 3253-1, 2768-1, 2793-1,
          2760-1, 2784-1, 2795-1, 2765-1, 2792-1
       (C) IDENTIFICATION METHOD: synthesis experiments
       (D) OTHER INFORMATION: complementary to synthetic RNA
          target (xi) SEQUENCE DESCRIPTION: SEQ ID NO:1:

CTCTCTCTCT CTCTA                                                  15

(2) INFORMATION FOR SEQ ID NO:2:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (ii) MOLECULE TYPE: other nucleic acid (iii) HYPOTHETICAL: no (iv) ANTI-SENSE: yes (ix) FEATURE:
       (A) NAME/KEY: CU oligomer
       (C) IDENTIFICATION METHOD: synthesis experiment (xi) SEQUENCE DESCRIPTION: SEQ ID NO:2:

CUCUCUCUCU CUCUA                                                  15

(2) INFORMATION FOR SEQ ID NO:3:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: other nucleic acid (iii) HYPOTHETICAL: no (iv) ANTI-SENSE: yes (ix) FEATURE:
       (A) NAME/KEY: oligomers 1634-1, 2570-1
       (C) IDENTIFICATION METHOD: synthesis experiments
       (D) OTHER INFORMATION: complementary to synthetic RNA
          target (xi) SEQUENCE DESCRIPTION: SEQ ID NO:3:

```
TAGCTTCCTT AGCTCCTGC                                                      19

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (ix) FEATURE:
        (A) NAME/KEY: oligomers 2624-1, 2571-1
        (C) IDENTIFICATION METHOD: synthesis experiments
        (D) OTHER INFORMATION: complementary to synthetic RNA
            target (xi) SEQUENCE DESCRIPTION: SEQ ID NO:4:

GTCTTCCATG CATGTTGTC                                                      19

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (ix) FEATURE:
        (A) NAME/KEY: GAG oligomer
        (C) IDENTIFICATION METHOD: synthesis experiment (xi) SEQUENCE DESCRIPTION: SEQ ID NO:5:

GAGGAGGAGG AGGAAGG                                                        17

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (ix) FEATURE:
        (A) NAME/KEY: oligomers 3130-1, 2566-1, 2567-1, 2687-1
            3169-1, 3214-1, 3257-1, 3256-1, 2681-1,
            2498-1, 3130-3
        (C) IDENTIFICATION METHOD: synthesis experiments
        (D) OTHER INFORMATION: cleave target mRNA and inhibit
            mRNA translation (xi) SEQUENCE DESCRIPTION: SEQ ID NO:6:

GTCTTCCATG CATGTTGTCC                                                     20
```

```
(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (ix) FEATURE:
        (A) NAME/KEY: oligomers 3258-1, 3260-1, XV-1
        (C) IDENTIFICATION METHOD: synthesis experiments
        (D) OTHER INFORMATION: inhibit target mRNA translation (xi) SEQUENCE DESCRIPTION: SEQ ID NO:7:

CATGGTAGCT TCCTTAGCTC CTGC                                              24

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (ix) FEATURE:
        (A) NAME/KEY: oligomers 3261-1, 3262-1, XV-2
        (C) IDENTIFICATION METHOD: synthesis experiments
        (D) OTHER INFORMATION: inhibit target mRNA translation (xi) SEQUENCE DESCRIPTION: SEQ ID NO:8:

GGTATATCCA GTGATCTTCT TCTC                                              24

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (ix) FEATURE:
        (A) NAME/KEY: oligomers 3269-1, 3270-1, XV-6
        (C) IDENTIFICATION METHOD: synthesis experiments
        (D) OTHER INFORMATION: inhibit target mRNA translation (xi) SEQUENCE DESCRIPTION: SEQ ID NO:9:

CACTCAATCA ATGACTAGTC TGCA                                              24

(2) INFORMATION FOR SEQ ID NO:10:

(i) SEQUENCE CHARACTERISTICS:
        (A) LENGTH: 15 base pairs
        (B) TYPE: nucleic acid
        (C) STRANDEDNESS: single
        (D) TOPOLOGY: linear
```

(ii) MOLECULE TYPE: other nucleic acid (iii) HYPOTHETICAL: no (iv) ANTI-SENSE: yes (ix) FEATURE:
            (A) NAME/KEY: oligomers 2323-1, 2253-1, 2252-1
            (C) IDENTIFICATION METHOD: synthesis experiments
            (D) OTHER INFORMATION: complementary to synthetic RNA
                target (xi) SEQUENCE DESCRIPTION: SEQ ID NO:10:

AGAGAGAGAG AGAGT                                                    15

(2) INFORMATION FOR SEQ ID NO:11:

(i) SEQUENCE CHARACTERISTICS:
           (A) LENGTH: 17 base pairs
           (B) TYPE: nucleic acid
           (C) STRANDEDNESS: single
           (D) TOPOLOGY: linear (ii) MOLECULE TYPE: other nucleic acid (iii) HYPOTHETICAL: no (iv) ANTI-SENSE: yes (ix) FEATURE:
            (A) NAME/KEY: GT oligomers 2517-1, 2516-1
            (C) IDENTIFICATION METHOD: synthesis experiments
            (D) OTHER INFORMATION: complementary to synthetic RNA
                target (xi) SEQUENCE DESCRIPTION: SEQ ID NO:11:

GTGTGTGTGT GTGTGTA                                                  17

(2) INFORMATION FOR SEQ ID NO:12:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: other nucleic acid (iii) HYPOTHETICAL: no (iv) ANTI-SENSE: yes (ix) FEATURE:
            (A) NAME/KEY: oligomers 2688-1, 2662-2
            (C) IDENTIFICATION METHOD: synthesis experiments
            (D) OTHER INFORMATION: complementary to synthetic RNA
                target (xi) SEQUENCE DESCRIPTION: SEQ ID NO:12:

ATGGTGTCTG TTTGAGGTT                                                19

(2) INFORMATION FOR SEQ ID NO:13:

(i) SEQUENCE CHARACTERISTICS:
           (A) LENGTH: 19 base pairs
           (B) TYPE: nucleic acid
           (C) STRANDEDNESS: single
           (D) TOPOLOGY: linear (ii) MOLECULE TYPE: other nucleic acid (iii) HYPOTHETICAL: no (iv) ANTI-SENSE: yes (ix) FEATURE:
              (A) NAME/KEY: oligomers 2625-1, 2574-1
              (C) IDENTIFICATION METHOD: synthesis experiments
              (D) OTHER INFORMATION: complementary to synthetic RNA
                   target (xi) SEQUENCE DESCRIPTION: SEQ ID NO:13:

GCTTCCATCT TCCTCGTCC                                                    19

(2) INFORMATION FOR SEQ ID NO:14:

(i) SEQUENCE CHARACTERISTICS:
              (A) LENGTH: 39 base pairs
              (B) TYPE: nucleic acid
              (C) STRANDEDNESS: single
              (D) TOPOLOGY: linear (ii) MOLECULE TYPE: mRNA (iii) HYPOTHETICAL: no (iv) ANTI-SENSE: no (ix) FEATURE:
              (A) NAME/KEY: wild-type CAT gene portion (as mRNA)
              (D) OTHER INFORMATION: pG1036 insert (as mRNA)

(xi) SEQUENCE DESCRIPTION: SEQ ID NO:14:

GCCUAUUUCC CUAUUUCCCU AAAGGGUUUA UUGAGAAUA                               39

(2) INFORMATION FOR SEQ ID NO:15:

(i) SEQUENCE CHARACTERISTICS:
              (A) LENGTH: 120 base pairs
              (B) TYPE: nucleic acid
              (C) STRANDEDNESS: single
              (D) TOPOLOGY: linear (ii) MOLECULE TYPE: mRNA (iii) HYPOTHETICAL: no (iv) ANTI-SENSE: no (ix) FEATURE:
              (A) NAME/KEY: CAT gene portion with intron (as mRNA)
              (D) OTHER INFORMATION: pG1035 insert (as mRNA)

(xi) SEQUENCE DESCRIPTION: SEQ ID NO:15:

UAUUUCCCUA UUUCCCUAAA GGUGAGUGAC UAACUAAGUC GACUGCAGAC UAGUCAUUGA         60

UUGAGUGUAA CAAGACCGGA UAUCUUCGAA CCUCUCUCUC UCUCUCAGGG UUUAUUGAGA        120

(2) INFORMATION FOR SEQ ID NO:16:

(i) SEQUENCE CHARACTERISTICS:
              (A) LENGTH: 54 base pairs
              (B) TYPE: nucleic acid
              (C) STRANDEDNESS: single
              (D) TOPOLOGY: linear (ii) MOLECULE TYPE: mRNA (iii) HYPOTHETICAL: no (iv) ANTI-SENSE: no (ix) FEATURE:
              (A) NAME/KEY: wild-type CAT gene portion (as mRNA)

(xi) SEQUENCE DESCRIPTION: SEQ ID NO:16:

UUUUCAGGAG CUAAGGAAGC UAAA AUG GAG AAA AAA AUC ACU GGA UAU ACC            51
                          Met Glu Lys Lys Ile Ser Gly Tyr Thr
                            1               5

ACC                                                                       54
Thr
 10

(2) INFORMATION FOR SEQ ID NO:17:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: mRNA (iii) HYPOTHETICAL: no (iv) ANTI-SENSE: no (ix) FEATURE:
            (A) NAME/KEY: pG1040 insert (as mRNA)

(xi) SEQUENCE DESCRIPTION: SEQ ID NO:17:

AGUGCAGGAG CUAAGGAAGC UACC AUG GAG AAG AAG AUC ACU GGA UAU ACC            51
                          Met Glu Lys Lys Ile Ser Gly Tyr Thr
                            1               5

ACC                                                                       54
Thr
 10

(2) INFORMATION FOR SEQ ID NO:18:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: no (iv) ANTI-SENSE: yes (ix) FEATURE:
            (A) NAME/KEY: oligomers 3264-1, XV-5
            (C) IDENTIFICATION METHOD: synthetic experiments
            (D) OTHER INFORMATION: inhibit target mRNA translation (xi) SEQUENCE DESCRIPTION: SEQ ID NO:18:

CACTCACCTT TAGGGAAATA GGCC                                                24

(2) INFORMATION FOR SEQ ID NO:19:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: no (iv) ANTI-SENSE: yes (ix) FEATURE:
            (A) NAME/KEY: oligomers 3265-1, 3266-1, XV-7

-continued

```
        (C) IDENTIFICATION METHOD: synthetic experiments
        (D) OTHER INFORMATION: inhibit target mRNA translation (xi) SEQUENCE DESCRIPTION: SEQ ID NO:19:

CCCTGAGAGA GAGAGAGAGG TTCG                                            24

(2) INFORMATION FOR SEQ ID NO:20:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: mRNA (iii) HYPOTHETICAL: no (iv) ANTI-SENSE: no (ix) FEATURE:
        (A) NAME/KEY: pG1042 mismatch insert (as mRNA)
        (D) OTHER INFORMATION: controlled mismatch oligomer
            screening (xi) SEQUENCE DESCRIPTION: SEQ ID NO:20:

AGUGCAAGAG UUGCGGAAGC UACC AUG GAC AGG AAG AUU ACG GGA UAU ACC        51
                          Met Asp Arg Lys Ile Thr Gly Tyr Thr
                           1               5
ACC                                                                   54
Thr
 10

(2) INFORMATION FOR SEQ ID NO:21:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: mRNA (iii) HYPOTHETICAL: yes (iv) ANTI-SENSE: no (ix) FEATURE:
        (A) NAME/KEY: mismatch insert (as mRNA)
        (D) OTHER INFORMATION: controlled mismatch oligomer
            screening (xi) SEQUENCE DESCRIPTION: SEQ ID NO:21:

AGUGCAGGAG CUAAGGAAGC UCCCAUGGAG AAGAAGAUCA CUGGAUAUAC CACC            54

(2) INFORMATION FOR SEQ ID NO:22:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: mRNA (iii) HYPOTHETICAL: yes (iv) ANTI-SENSE: no (ix) FEATURE:
        (A) NAME/KEY: mismatch insert (as mRNA)
        (D) OTHER INFORMATION: controlled mismatch oligomer
```

-continued screening (xi) SEQUENCE DESCRIPTION: SEQ ID NO:22:

AGUGCAGGAG CUAAGGAAAC UCCCAUGGAG AAGAAGAUCA CUGGAUAUAC CACC          54

(2) INFORMATION FOR SEQ ID NO:23:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: mRNA (iii) HYPOTHETICAL: yes (iv) ANTI-SENSE: no (ix) FEATURE:
        (A) NAME/KEY: mismatch insert (as mRNA)
        (D) OTHER INFORMATION: controlled mismatch oligomer
            screening (xi) SEQUENCE DESCRIPTION: SEQ ID NO:23:

AGUGCAGGAG CUAAGUAAAC UCCCAUGGAG AAGAAGAUCA CUGGAUAUAC CACC          54

(2) INFORMATION FOR SEQ ID NO:24:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: mRNA (iii) HYPOTHETICAL: yes (iv) ANTI-SENSE: no (ix) FEATURE:
        (A) NAME/KEY: mismatch insert (as mRNA)
        (D) OTHER INFORMATION: controlled mismatch oligomer
            screening (xi) SEQUENCE DESCRIPTION: SEQ ID NO:24:

AGUGCAGGAG CUGAGUAAAC UCCCAUGGAG AAGAAGAUCA CUGGAUAUAC CACC          54

(2) INFORMATION FOR SEQ ID NO:25:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: mRNA (iii) HYPOTHETICAL: yes (iv) ANTI-SENSE: no (ix) FEATURE:
        (A) NAME/KEY: mismatch insert (as mRNA)
        (D) OTHER INFORMATION: controlled mismatch oligomer
            screening (xi) SEQUENCE DESCRIPTION: SEQ ID NO:25:

AGUGCAGGAC CUGAGUAAAC UCCCAUGGAG AAGAAGAUCA CUGGAUAUAC CACC          54

(2) INFORMATION FOR SEQ ID NO:26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: yes (iv) ANTI-SENSE: yes (ix) FEATURE:
        (A) NAME/KEY: mismatch oligomer
        (D) OTHER INFORMATION: mismatch oligomer to target
            mRNA SEQ ID NOS: 21-25

(xi) SEQUENCE DESCRIPTION: SEQ ID NO:26:

CATGGTAGCT TCCTTAGCTC C                                                  21

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: no (ix) FEATURE:
        (A) NAME/KEY: RNA target oligomer
        (C) IDENTIFICATION METHOD: synthetic experiment
        (D) OTHER INFORMATION: target for oligomers 2681-1,
            3214-1

(xi) SEQUENCE DESCRIPTION: SEQ ID NO:27:

CAGAAGGUAC GUACAACAGG                                                    20